(12) United States Patent
Kitazawa et al.

(10) Patent No.: US 8,003,851 B2
(45) Date of Patent: Aug. 23, 2011

(54) PLANT PRODUCING HYALURONIC ACID

(75) Inventors: Hiroaki Kitazawa, Otsu (JP); Shigeo Shibatani, Otsu (JP); Atsushi Sogabe, Otsu (JP)

(73) Assignee: Toyo Boseki Kabushiki Kaisha, Osaka-shi (JP)

( * ) Notice: Subject to any disclaimer, the term of this patent is extended or adjusted under 35 U.S.C. 154(b) by 677 days.

(21) Appl. No.: 12/063,888

(22) PCT Filed: Aug. 10, 2006

(86) PCT No.: PCT/JP2006/315817
§ 371 (c)(1),
(2), (4) Date: Feb. 15, 2008

(87) PCT Pub. No.: WO2007/023682
PCT Pub. Date: Mar. 1, 2007

(65) Prior Publication Data
US 2009/0260108 A1    Oct. 15, 2009

(30) Foreign Application Priority Data

Aug. 25, 2005 (JP) .................................. 2005-244192
Feb. 21, 2006 (JP) .................................. 2006-043724

(51) Int. Cl.
*C12N 15/82* (2006.01)
*C12N 15/09* (2006.01)
*C12N 15/00* (2006.01)

(52) U.S. Cl. .................. 800/288; 800/278; 435/320.1; 435/468; 536/23.1; 536/23.2; 536/23.7

(58) Field of Classification Search .................. None
See application file for complete search history.

(56) References Cited

U.S. PATENT DOCUMENTS

| | | | |
|---|---|---|---|
| 7,547,819 B2 * | 6/2009 | Shibatani et al. | ............ 800/280 |
| 2003/0175902 A1 * | 9/2003 | Sloma et al. | ................... 435/84 |
| 2006/0168690 A1 | 7/2006 | Shibatani et al. | |

FOREIGN PATENT DOCUMENTS

| | | |
|---|---|---|
| EP | 1025211 B1 | 12/2004 |
| JP | 58-056692 A | 4/1983 |
| JP | 05-125103 A | 5/1993 |
| JP | 06-319579 A | 11/1994 |
| JP | 06-319580 A | 11/1994 |
| JP | 09-056394 A | 3/1997 |
| JP | 2001-521741 A | 11/2001 |
| WO | WO 99/23227 A2 | 5/1999 |
| WO | WO 2005/012529 A1 | 2/2005 |
| WO | WO 2007/039314 A2 | 4/2007 |
| WO | WO 2007/039316 A1 | 4/2007 |

OTHER PUBLICATIONS

Orlane, FDC Reports Rose Sheet, ISSN: 0279-1110 (Feb. 11, 1991).
Yamada et al., *Journal of Bioscience and Bioengineering*, 99(6): 521-528 (Jun. 1, 2005).
Widner et al., *Applied and Environmental Microbiology*, 71(7): 3747-3752 (Jul. 1, 2005).
Deangelis et al., *Science*, 278(5344): 1800-1803 (Dec. 5, 1997).
Graves et al., *Virology*, 257(1): 15-23 (1999).
Landstein et al., *Virology*, 250(2): 388-396 (1998).
Meyer et al., *J. Biol. Chem.*, 107(3): 629-634 (1934).
Petrides et al., *Biotech. & Bioeng.*, 48(5): 529-541 (1995).
Shibatani et al., "Research and Development of Plants that Produce Exogenous Carbohydrates," Toyobo Research Ctr. Co., Ltd. (Nov. 4, 2004).
Database DDBJ/EMBL/GenBank [online], Accession No. NM_113314 [retrieved on Nov. 12, 2010 from URL <http://www.ncbi.nlm.nih.gov/nuccore/18404036?sat=OLD04&satkey=6488194>].
Seitz et al., *The Plant Journal*, 21(6): 537-548 (2000).
DeAngelis, "Hyaluronan synthases: fascinating glycosyltransferases from vertebrates, bacterial pathogens, and algal viruses," *Cell. Mol. Life Sci.*, 56: 670-682 (1999).
Johansson et al., "Molecular cloning and characterization of a cDNA encoding poplar UDP-glucose dehydrogenase, a key gene of hemicelluloses/pectin formation," *Biochimica et Biophysica Acta*, 1576: 53-58 (2002).
Milewski, "Glucosamine-6-phosphate synthase—the multi-facets enzyme," *Biochimica et Biophysica Acta*, 1597: 173-192 (2002).

* cited by examiner

*Primary Examiner* — Brent T Page
(74) *Attorney, Agent, or Firm* — Leydig, Voit & Mayer, Ltd.

(57) ABSTRACT

It is intended to provide by improving a known method of producing hyaluronic acid in a plant, a plant or a cultured plant cells which can produce hyaluronic acid at a lower cost and a further higher yield than before, a method of preparing the same, an expression vector for transformation, a method of producing hyaluronic acid using the plant or the cultured plant cells and the like. The method of producing hyaluronic acid comprising obtaining hyaluronic acid by co-expressing a protein with hyaluronic acid synthase activity and an exogenous protein with sugar-nucleotide synthase activity in a plant cell or a plant is provided.

38 Claims, 6 Drawing Sheets

M: Molecular weight standards
1: AtGFAT (Before Reaction)
2: AtGFAT (After 24-hour Reaction)
3: cvGFAT-HI (Before Reaction)
4: cvGFAT-HI (After 24-hour Reaction)
5: DHFR (Before Reaction)
6: DHFR (After 24-hour Reaction)

PLANT PRODUCING HYALURONIC ACID

TECHNICAL FIELD

The present invention generally relates to a method of producing hyaluronic acid in plants, transgenic plant cells or transgenic plants having an ability to produce hyaluronic acid, and methods of producing these transgenic cells and transgenic plants.

BACKGROUND ART

Hyaluronic acid is a glycosaminoglycan (mucopolysaccharide) isolated from the vitreous body of a bovine eye ball by Meyer and Palmer in 1934 (Meyer, K. and Palmer, J. W. (1934) J. Biol. Chem., 107, 629-634). High-molecular-weight hyaluronic acid has been used for the treatment of osteoarthritis, a surgery aid for ophthalmology, adhesion prevention, acceleration of wound healing and the like. It has been also reported that low-molecular-weight hyaluronic acid has physiologically active effects. New uses for hyaluronic acid as a biomaterial or in a medical application are expected to be found.

Until now, hyaluronic acid has been produced by extraction from mammalian tissues or microbial fermentation. However, risk of contamination with, for example, transmissible spongiform encephalopathies (prions) or transmission of viruses to humans has been concerned in the extraction from the mammalian tissues. Mammalian cells are expensive to grow and maintain. They require expensive growth media and grow slowly. Meanwhile, microbial fermentations have problems such as the requirement for sugar-containing growth medium and expensive facilities. In *Escherichia coli*, there are problems in that proteins are not processed, inclusion body might be formed, proteins are degraded by proteases, and the like. (Petrides, D. et al., (1995) Biotecnol. Bioeng., 48, 529). When therapeutic substances are produced in microorganisms, the purification costs become extremely expensive in order to prevent endotoxin contamination.

On the contrary, plants are ideal systems for producing carbohydrate with low energy load, in which carbohydrates are photosynthetically produced from water and carbon dioxide. The invention disclosed in Patent Document 6 shows that hyaluronic acid can be produced by introducing a hyaluronic acid synthase gene into plants or plant cells.

Patent Document 1: Japanese Unexamined Patent Application No. 1993-125103
Patent Document 2: Japanese Unexamined Patent Publication No. 1983-056692
Patent Document 3: Japanese Unexamined Patent Application No. 1997-319579
Patent Document 4: Japanese Unexamined Patent Application No. 1994-319580
Patent Document 5: Japanese Unexamined Patent Application No. 1997-056394
Patent Document 6: WO 05/012529
Nonpatent Document 1: Meyer, K. and Palmer, J. W., J. Biol. Chem., 107: 629-634, 1934
Nonpatent Document 2: Petrides, D. et al., Biotecnol. Bioeng., 48: 529, 1995

DISCLOSURE OF THE INVENTION

Figure 1:
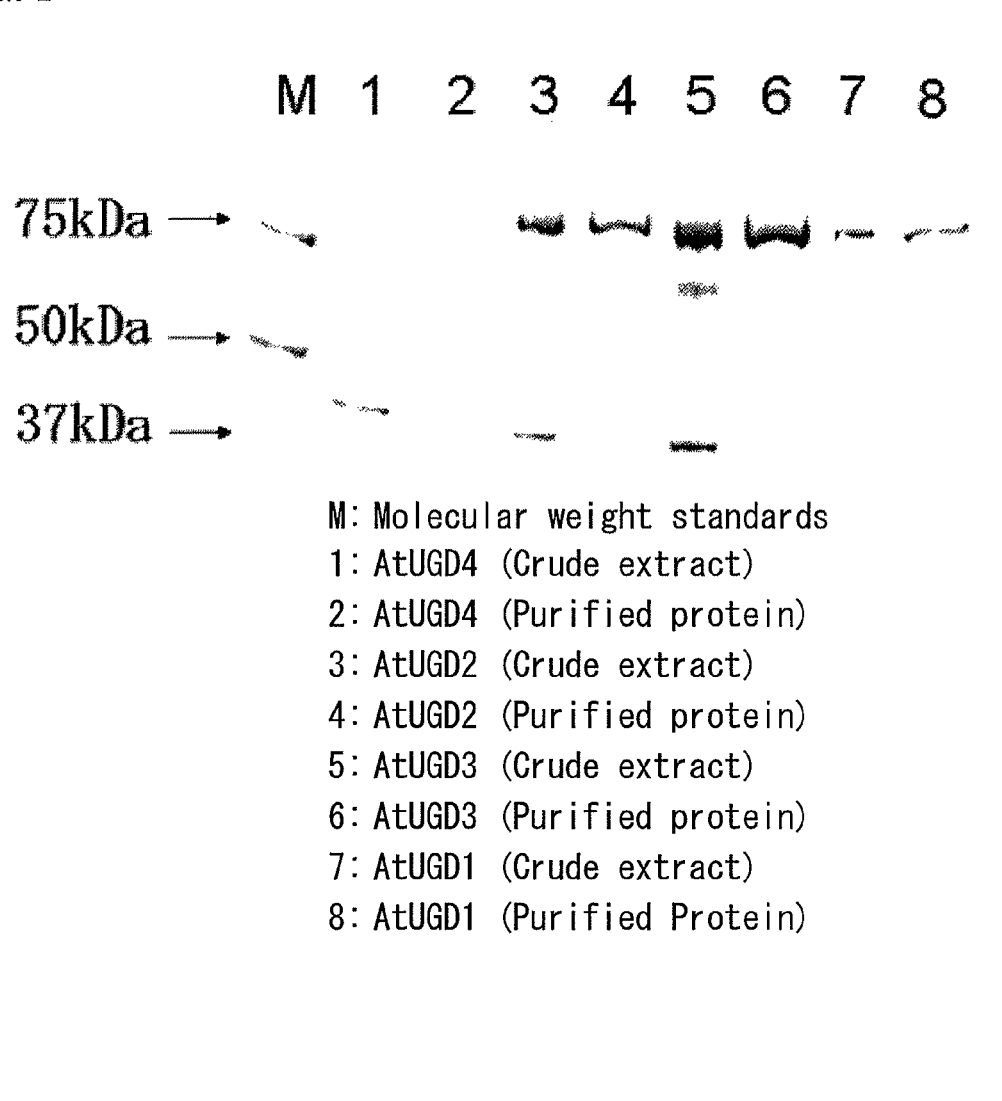
FIG. 1 shows SDS-PAGE analysis of AtUGD before and after purification.

Problems to be Solved by the Invention

The primary object of the present invention is to provide plants and plant cells that can produce hyaluronic acid more effectively by improving previously known methods of producing hyaluronic acid in plants, the methods of producing thereof, and the recombinant expression vectors therefor.

Means for Solving the Problems

As a result of extensive study to solve the above problems, the present inventor has found that hyaluronic acid is produced extensively in the plants by transforming plants and plant cells with genes that encode proteins having enzymatic activity of producing hyaluronic acid and genes that encode proteins having enzymatic activity of synthesizing sugar-nucleotides, and further extensively study has achieved the present invention.

That is, the present invention relates to the following items.
1. A method of producing hyaluronic acid, comprising co-expressing a protein with hyaluronic acid synthase activity and an exogenous protein with sugar-nucleotide synthase activity in a plant cell or a plant.
2. A method of producing hyaluronic acid, containing the steps of:
   (1) transforming a plant cell or a plant using a recombinant expression vector, the recombinant expression vector having DNA encoding a protein with hyaluronic acid synthase activity and DNA encoding a protein with sugar-nucleotide synthase activity under control of a promoter(s) capable of functioning in plants;
   (2) growing a transformant obtained by the transformation; and
   (3) isolating hyaluronic acid produced by the transformant.
3. The method of producing hyaluronic acid according to Item 2, wherein the promoter is an organ-specific or a tissue-specific promoter.
4. The method of producing hyaluronic acid according to Item 2 or 3, wherein the DNA encoding a protein with hyaluronic acid synthase activity is DNA of (a) or (b) below:
   (a) DNA consisting of a nucleotide sequence represented by SEQ ID NO: 1 or 3; or
   (b) DNA hybridizing to the nucleotide sequence complementary to DNA consisting of the nucleotide sequence of (a) under stringent conditions, and the DNA encoding a protein with hyaluronic acid synthase activity.
5. The method of producing hyaluronic acid according to any of Items 1 to 3, wherein the protein with hyaluronic acid synthase activity is a protein of (a) or (b) below:
   (a) a protein consisting of an amino acid sequence represented by SEQ ID NO: 2 or 4; or
   (b) a protein having the amino acid sequence of (a) with one or a few amino acids deleted, substituted or added, and the protein having hyaluronic acid synthase activity.

6. The method of producing hyaluronic acid according to any of Items 1 to 5, wherein the sugar nucleotide is uridin-5'-diphospho(UDP)-N-acetylglucosamine and/or UDP-glucuronic acid.

7. The method of producing hyaluronic acid according to any of Items 1 to 6, wherein the protein with sugar-nucleotide synthase activity is at least one protein selected from the group consisting of glutamine:fructose-6-phosphate amidotransferase, UDP-N-acetylglucosamine diphosphorylase, phosphoacetyl glucosamine mutase, glucosamine-6-phosphate N-acetyltransferase, glucosamine-1-phosphate N-acetyltransferase, phosphoglucomutase, N-acetylglucosamine kinase, hexokinase, N-acetylglucosamine acetylase, UDP-glucose dehydrogenase, UDP-glucose-1-phosphate uridyltransferase, inositol oxygenase, glucuronokinase and glucuronate-1-phosphate uridyl transferase.

8. The method of producing hyaluronic acid according to any of Items 1 to 6, wherein the protein with sugar-nucleotide synthase activity is at least one protein selected from the group consisting of UDP-N-acetylglucosamine diphosphorylase, phosphoacetyl glucosamine mutase, glucosamine-6-phosphate N-acetyltransferase, glucosamine-1-phosphate N-acetyltransferase, phosphoglucomutase, N-acetylglucosamine kinase, hexokinase, N-acetylglucosamine acetylase, UDP-glucose dehydrogenase, UDP-glucose-1-phosphate uridyltransferase, inositol oxygenase, glucuronokinase and glucuronate-1-phosphate uridyl transferase, and glutamine:fructose-6-phosphate amidotransferase.

9. The method of producing hyaluronic acid according to any of Items 1 to 6, wherein a protein with sugar-nucleotide synthase activity is glutamine:fructose-6-phosphate amidotransferase and/or UDP-glucose dehydrogenase.

10. The method of producing hyaluronic acid according to any of Items 2 to 9, wherein the DNA encoding a protein with sugar nucleotide synthase activity is DNA derived from chlorella virus and/or *Arabidopsis thaliana*.

11. The method of producing hyaluronic acid according to any of Items 2 to 10, wherein the DNA encoding a protein with sugar-nucleotide synthase activity is DNA of (a) or (b) below:
 (a) DNA consisting of a nucleotide sequence represented by SEQ ID NO: 5, 7 or 9; or
 (b) DNA hybridizing to the nucleotide sequence complementary to DNA consisting of the nucleotide sequence of (a) under stringent conditions, and said DNA encoding a protein with glutamine:fructose-6-phosphate amidotransferase activity.

12. The method of producing hyaluronic acid according to any of Items 1 to 10, wherein the protein with sugar-nucleotide synthase activity is a protein of (a) or (b) below:
 (a) a protein consisting of an amino acid sequence represented by SEQ ID NO: 6, 8 or 10; or
 (b) a protein consisting of the amino acid sequence of (a) with one or a few amino acids deleted, substituted or added, and the protein having glutamine:fructose-6-phosphate amidotransferase activity.

13. The method of producing hyaluronic acid according to any of Items 2 to 10, wherein the DNA encoding a protein with sugar-nucleotide synthase activity is DNA of (a) or (b) below:
 (a) DNA consisting of a nucleotide sequence represented by SEQ ID NO: 11, 13, 17, 19, or 21; or
 (b) DNA hybridizing to the nucleotide sequence complementary to DNA consisting of the nucleotide sequence of (a) under stringent conditions, and the DNA encoding a protein with UDP-glucose dehydrogenase activity.

14. The method of producing hyaluronic acid according to any of Items 1 to 10, wherein the protein with sugar-nucleotide synthase activity is a protein of (a) or (b) below:
 (a) a protein consisting of an amino acid sequence represented by SEQ ID NO: 12, 14, 16, 18, 20 or 22; or
 (b) a protein consisting of the amino acid sequence of (a) with one or a few amino acids deleted, substituted or added, and the protein having UDP-glucose dehydrogenase activity.

15. The method of producing hyaluronic acid according to any of Items 1 to 14, wherein the plant is selected from the group consisting of angiosperms, gymnosperms, pteridophytes and bryophytes.

16. The method of producing hyaluronic acid according to Item 3, wherein organs are selected from the group consisting of roots, stems, stem tubers, leave, floral organs, tuberous roots, seeds and shoot apices.

17. The method of producing hyaluronic acid according to Item 3, wherein one or more tissues are selected from the group consisting of epidermis, phloem, soft tissues, xylem and vascular bundles.

18. A transgenic plant cell or a transgenic plant having an ability to produce hyaluronic acid by co-expressing a protein with hyaluronic acid synthase activity and an exogenous protein with sugar-nucleotide synthase activity, or a progeny thereof, or an organ or a tissue thereof having the same nature as in the plant.

19. A transgenic plant cell or a transgenic plant having an ability of producing hyaluronic acid, being transformed with an recombinant expression vector containing DNA encoding a protein with hyaluronic acid synthase activity and DNA encoding a protein with sugar-nucleotide synthase activity under control of a promoter capable of functioning in plants; a progeny having the same nature thereof; or an organ or a tissue thereof.

20. The transgenic plant cell or the transgenic plant, the progeny having the same nature thereof, or the organ or the tissue thereof according to Item 19, wherein the promoter is an organ-specific or a tissue-specific promoter.

21. The transgenic plant cell or the transgenic plant, the progeny having the same nature thereof, or the organ or the tissue thereof according to Item 19 or 20, wherein the DNA encoding a protein with hyaluronic acid synthase activity is DNA of (a) or (b) below:
 (a) DNA consisting of a nucleotide sequence represented by SEQ ID NO: 1 or 3; or
 (b) DNA hybridizing to the nucleotide sequence complementary to DNA consisting of the nucleotide sequence of (a) under stringent conditions, and the DNA encoding a protein with hyaluronic acid synthase activity.

22. The transgenic plant cell or the transgenic plant according to any of Items 18 to 20, wherein the protein with hyaluronic acid synthase activity is a protein of (a) or (b) below:
 (a) a protein consisting of an amino acid sequence represented by SEQ ID NO: 2 or 4; or
 (b) a protein consisting of the amino acid sequence of (a) with one or a few amino acids deleted, substituted or added, and the protein having hyaluronic acid synthase activity.

23. The transgenic plant cell or the transgenic plant, the progeny having the same nature thereof, or the organ or the tissue thereof according to any of Items 18 to 22, wherein the sugar nucleotide is UDP-N-acetylglucosamine and/or UDP-glucuronic acid.

24. The transgenic plant cell or the transgenic plant according to any of Items 18 to 23, wherein the protein with sugar-nucleotide synthase activity is at least one protein selected from the group consisting of, glutamine:fructose-6-phosphate amidotransferase, UDP-N-acetylglucosamine diphosphorylase, phosphoacetyl glucosamine mutase, glucosamine-6-phosphate N-acetyltransferase, glucosamine-1-phosphate N-acetyltransferase, phosphoglucomutase, N-acetylglucosamine kinase, hexokinase, N-acetylglucosamine acetylase, UDP-glucose dehydrogenase, UDP-glucose-1-phosphate uridyltransferase, inositol oxygenase, glucuronokinase and glucuronate-1-phosphate uridyl transferase.

25. The transgenic plant cell or the transgenic plant, the progeny having the same nature thereof, or the organ or the tissue thereof according to any of Items 18 to 23, wherein the protein with sugar-nucleotide synthase activity is at least one protein selected from the group consisting of UDP-N-acetylglucosamine diphosphorylase, phosphoacetyl glucosamine mutase, glucosamine-6-phosphate N-acetyltransferase, glucosamine-1-phosphate N-acetyltransferase, phosphoglucomutase, N-acetylglucosamine kinase, hexokinase, N-acetylglucosamine acetylase, UDP-glucose dehydrogenase, UDP-glucose-1-phosphate uridyltransferase, inositol oxygenase, glucuronokinase and glucuronate-1-phosphate uridyl transferase, and glutamine:fructose-6-phosphate amidotransferase.

26. The transgenic plant cell or the transgenic plant, the progeny having the same nature thereof, or the organ or the tissue thereof according to any of Items 18 to 23, wherein the protein with sugar-nucleotide synthase activity is glutamine:fructose-6-phosphate amidotransferase and/or UDP-glucose dehydrogenase.

27. The transgenic plant cell or the transgenic plant, the progeny having the same nature thereof, or the organ or the tissue thereof according to any of Items 19 to 26, wherein DNA encoding a protein with sugar nucleotide synthase activity is derived from chlorella virus and/or *Arabidopsis thaliana*.

28. The transgenic plant cell or the transgenic plant; the progeny having the same nature thereof; or the organ or the tissue thereof according to any of Items 19 to 27, wherein DNA encoding a protein with sugar-nucleotide synthase activity is DNA of (a) or (b) below:
 (a) DNA consisting of a nucleotide sequence represented by SEQ ID NO: 5, 7 or 9; or
 (b) DNA hybridizing to the nucleotide sequence complementary to DNA consisting of the nucleotide sequence of (a) under stringent conditions, and the DNA encoding a protein with glutamine:fructose-6-phosphate amidotransferase activity.

29. The transgenic plant cell or the transgenic plant, the progeny having the same nature thereof, or the organ or the tissue thereof according to any of Items 18 to 27, wherein the protein with sugar-nucleotide synthase activity is a protein of (a) or (b) below:
 (a) a protein consisting of an amino acid sequence represented by SEQ ID NO: 6, 8 or 10; or
 (b) a protein consisting of the amino acid sequence of (a) with one or a few amino acids deleted, substituted or added, and the protein having glutamine:fructose-6-phosphate amidotransferase activity.

30. The transgenic plant cell or the transgenic plant, the progeny having the same nature thereof, or the organ or the tissue thereof according to any of Items 19 to 27, wherein the DNA encoding a protein with sugar-nucleotide synthase activity is DNA of (a) or (b) below:
 (a) DNA consisting of a nucleotide sequence represented by SEQ ID NO: 11, 13, 15, 17, 19, or 21; or
 (b) DNA hybridizing to DNA consisting of the base sequence complementary to the base sequence of (a) under stringent conditions, and the DNA encoding a protein with DP-glucose dehydrogenase activity.

31. The transgenic plant cell or the transgenic plant, the progeny having the same nature thereof, or the organ or the tissue thereof according to any of Items 18 to 27, wherein the protein with sugar-nucleotide synthase activity is a protein of (a) or (b) below:
 (a) a protein consisting of an amino acid sequence represented by SEQ ID NO: 12, 14, 16, 18, 20 or 22; or
 (b) a protein consisting of the amino acid sequence of (a) with one or a few amino acids deleted, substituted or added, and said protein with UDP-glucose dehydrogenase activity.

32. The transgenic plant cell or the transgenic plant, the progeny having the same nature thereof, or the organ or the tissue thereof according to any of Items 18 to 31, wherein the plant is any plant selected from the group consisting of gymnosperms, gymnosperms, pteridophytes and bryophytes.

33. The transgenic plant cell or the transgenic plant; the progeny having the same nature thereof; or the organ or the tissue thereof according to any of Items 18 to 31, wherein the organ is one or more organs selected from the group consisting of roots, stems, stem tubers, leaves, floral organs, tuberous roots, seeds and shoot apices.

34. The transgenic plant cell or the transgenic plant, the progeny having the same nature thereof, or the organ or the tissue thereof according to any of Items 18 to 31, wherein the tissue is one or more tissues selected from the group consisting of epidermis, phloem, soft tissues, xylem and vascular bundles.

35. Plant extract obtained from the transgenic plant cell or the transgenic plant, the progeny having the same nature thereof, or the organ or the tissue thereof according to any of Items 18 to 34.

36. The plant extract according to Item 35, wherein the plant extract contains hyaluronic acid.

37. A recombinant expression vector, comprising DNA encoding a protein with hyaluronic acid synthase activity and DNA encoding a protein with sugar-nucleotide synthase activity under control of a promoter capable of functioning in plants.

38. The recombinant expression vector according to Item 37, wherein the promoter is an organ-specific, or a tissue-specific promoter.

39. The recombinant expression vector according to Item 37 or 38, wherein the DNA encoding a protein with hyaluronic acid synthase activity is DNA of (a) or (b) below:
 (a) DNA consisting of a nucleotide sequence represented by SEQ ID NO: 1 or 3; or
 (b) DNA hybridizing to DNA consisting of the nucleotide sequence complementary to the nucleotide sequence of (a) under stringent conditions, and the DNA encoding a protein with hyaluronic acid activity.

40. The recombinant expression vector according to Item 37 or 38, wherein the protein with hyaluronic acid synthase activity is a protein of (a) or (b) below:
 (a) a protein consisting of an amino acid sequence represented by SEQ ID NO: 2 or 4; or
 (b) a protein consisting of the amino acid sequence of (a) with one or a few amino acids deleted, substituted or added, and the protein having hyaluronic acid synthase activity.

41. The recombinant expression vector according to any of Items 37 to 40, wherein the sugar nucleotide is UDP-N-acetylglucosamine and/or UDP-glucuronic acid.

42. The recombinant expression vector according to any of Items 37 to 41, wherein the protein with sugar-nucleotide synthase activity is at least one protein selected from the group consisting of glutamine:fructose-6-phosphate amidotransferase, UDP-N-acetylglucosamine diphosphorylase, phosphoacetyl glucosamine mutase, glucosamine-6-phosphate N-acetyltransferase, glucosamine-1-phosphate N-acetyltransferase, phosphoglucomutase, N-acetylglucosamine kinase, hexokinase, N-acetylglucosamine acetylase, UDP-glucose dehydrogenase, UDP-glucose-1-phosphate uridyltransferase, inositol oxygenase, glucuronokinase and glucuronate-1-phosphate uridyl transferase.

43. The recombinant expression vector according to any of Items 37 to 41, wherein the protein with sugar-nucleotide synthase activity is at least one protein selected from the group consisting of UDP-N-acetylglucosamine diphosphorylase, phosphoacetyl glucosamine mutase, glucosamine-6-phosphate N-acetyltransferase, glucosamine-1-phosphate N-acetyltransferase, phosphoglucomutase, N-acetylglucosamine kinase, hexokinase, N-acetylglucosamine acetylase, UDP-glucose dehydrogenase, UDP-glucose-1-phosphate uridyltransferase, inositol oxygenase, glucuronokinase and glucuronate-1-phosphate uridyl transferase, and glutamine:fructose-6-phosphate amidotransferase.

44. The recombinant expression vector according to any of Items 37 to 41, wherein the protein with sugar-nucleotide synthase activity is glutamine:fructose-6-phosphate amidotransferase and/or UDP-glucose dehydrogenase.

45. The recombinant expression vector according to any of Items 37 to 41, wherein the DNA encoding a protein with sugar nucleotide synthase activity is DNA derived from chlorella virus and/or Arabidopsis thaliana.

46. The recombinant expression vector according to any of Items 37 to 44, wherein the DNA encoding a protein with sugar nucleotide synthase activity is DNA of (a) or (b) below:
 (a) DNA consisting of a nucleotide sequence represented by SEQ ID NO: 5, 7 or 9; or
 (b) DNA hybridizing to DNA consisting of the nucleotide sequence complementary to the nucleotide sequence of (a) under stringent conditions, and said DNA encoding a protein with glutamine:fructose-6-phosphate amidotransferase activity.

47. The recombinant expression vector according to any of Items 37 to 44, wherein the protein with sugar-nucleotide synthase activity is a protein of (a) or (b) below:
 (a) a protein consisting an amino acid sequence represented by SEQ ID NO: 6, 8 or 10; or
 (b) a protein consisting of the amino acid sequence of (a) with one or a few amino acids deleted, substituted or added, and the protein having glutamine:fructose-6-phosphate amidotransferase activity.

48. The recombinant expression vector according to any of Items 37 to 44, wherein the DNA encoding a protein with sugar nucleotide synthase activity is DNA of (a) or (b) below:
 (a) DNA consisting of a nucleotide sequence represented by SEQ ID NO: 11, 13, 15, 17, 19, or 21; or
 (b) DNA hybridizing to DNA consisting of the nucleotide sequence complementary to the nucleotide sequence of (a) under stringent conditions, and said DNA encoding a protein with UDP-glucose dehydrogenase activity.

49. The recombinant expression vector according to any of Items 37 to 44, wherein the protein with sugar-nucleotide synthase activity is a protein of (a) or (b) below:
 (a) a protein consisting of an amino acid sequence represented by SEQ ID NO: 12, 14, 16, 18, 20 or 22; or
 (b) a protein consisting of the amino acid sequence of (a) with one or a few amino acids deleted, substituted or added, and said protein having UDP-glucose dehydrogenase activity.

50. A method of producing transgenic plant cell or the transgenic plant having an ability to produce hyaluronic acid, the method comprising transforming a plant cell or a plant using any vector according to Items 37 to 49.

51. A cosmetic composition containing hyaluronic acid as an active agent, wherein the hyaluronic acid is obtained by any of the methods of producing hyaluronic acid according to Items 1 to 17.

Effects of the Invention

According to the present invention, hyaluronic acid, which is not naturally produced in plants, is produced in plants. According to the present invention, a gene encoding a protein with hyaluronic acid synthase activity and a gene encoding a protein with sugar-nucleotide synthase activity are expressed in plants, so that hyaluronic acid is highly produced in plants. Plants or cultured plant cells capable of producing more hyaluronic acid than by conventional methods, a method thereof, and a recombinant expression vector thereof can be provided. Therefore, the present invention can provide plant-produced safe hyaluronic acid at low cost.

BEST MODE FOR CARRYING OUT THE INVENTION

A feature of the present invention is a method of producing hyaluronic acid, containing co-expressing a protein with hyaluronic acid synthase activity and an exogenous protein with sugar nucleotide synthase activity in plant cells or plants so as to obtain hyaluronic acid.

Another feature of the present invention is a method of producing hyaluronic acid containing:
 (1) transforming plant cells or plants using a recombinant expression vector that contains DNA encoding a protein with hyaluronic acid synthase activity and DNA encoding a protein with sugar-nucleotide synthase activity under the control of a promoter(s) capable of functioning in plants;
 (2) growing the transformant obtained by the transformation; and
 (3) isolating hyaluronic acid produced in the transformants.

Yet another feature of the present invention is cosmetic compositions that contain hyaluronic acid as an active agent, wherein the hyaluronic acid is obtained by the above method for producing hyaluronic acid.

Yet another feature of the present invention is a recombinant expression vector for producing hyaluronic acid, wherein the recombinant expression vector contains DNA encoding a protein with hyaluronic acid synthase activity and DNA encoding a protein with sugar-nucleotide synthase activity under the control of a promoter(s) capable of functioning in plants.

Some features of the present invention are transgenic plant cells or transgenic plants, the progenies having the same nature thereof, or the organs or the tissues thereof, wherein the transformants have obtained an ability to produce hyaluronic acid by co-expressing a protein with hyaluronic acid synthase activity and an exogenous protein with sugar-nucleotide synthase activity.

A feature of the present invention is transgenic plant cells or transgenic plants, the progenies having the same nature thereof, or the organs or the tissues thereof, wherein the transformants are transformed using a recombinant expression vector containing DNA encoding a protein with hyaluronic acid synthase activity and DNA encoding a protein with sugar-nucleotide synthase activity under the control of a promoter(s) capable of functioning in plants.

Another feature of the present invention is a method for producing transgenic plant cells or transgenic plants that have an ability to produce hyaluronic acid. The method includes transforming plant cells or plants using a recombinant expression vector that contains DNA encoding a protein with hyaluronic acid synthase activity and DNA encoding a protein with sugar-nucleotide synthase activity under the control of a promoter(s) capable of functioning in plants.

The following explains the present invention in detail.

Hyaluronic Acid Synthase

In the present invention, plant cells or plants are transformed using DNA encoding a protein with hyaluronic acid synthase activity and DNA encoding a protein with sugar-nucleotide synthase activity under the control of a promoter(s) capable of functioning in plants.

In the present invention, a protein with hyaluronic acid synthase activity synthesizes hyaluronic acid using UDP-glucuronic acid and UDP-N-acetylglucosamine as substrates. The hyaluronic acid has a polymer structure consisting of repeated units of glucuronic acid and N-acetylglucosamine.

In the present invention, a protein with hyaluronic acid synthase activity is, as long as the protein has the above mentioned nature, not particularly limited. Hyaluronic acid synthase (hereinafter be occasionally abbreviated as HAS) derived from animals, microorganisms, viruses and the like can be used. Particularly, hyaluronic acid synthase derived from vertebrates such as humans, mice, rabbits, chickens, cattle and *Xenopus laevis*, microorganisms such as *Streptococcus* and *Pasteurella*, viruses such as chlorella virus and the like can be used.

More specifically, examples of the protein with hyaluronic acid synthase activity are HAS (A98R) derived from chlorella virus PBCV-1; HAS1, HAS2 and HAS3 of the hyaluronic acid synthase (hHAS) derived from humans; HAS1, HAS2 and HAS3 of the mouse derived hyaluronic acid synthase (mHAS); HAS1, HAS2 and HAS3 of the chicken derived hyaluronic acid synthase (gHAS); HAS2 of the rat derived hyaluronic acid synthase (rHAS); HAS2 of the cattle derived hyaluronic acid synthase (bHAS); HAS1, HAS2 and HAS3 of the *Xenopus laevis* derived hyaluronic acid synthase (xHAS); the *Pasteurella multocida* derived hyaluronic acid synthase (pmHAS); the *Streptococcus pyogenes* derived hyaluronic acid synthase (spHAS); and the hyaluronic acid synthase (seHAS) gene derived from *Streptococcus equisimilis*. There are various types of hyaluronic acid synthase (HAS) genes such as HAS1, HAS2 and HAS3, however, the type is not particularly limited. Any of the above described HAS can be used, among which the chlorella virus derived HAS is preferable, chlorella virus derived HAS which are shown by a protein consisting of an amino acid sequence represented by SEQ ID NO: 2 or 4 is more preferable.

The protein consisting of an amino acid sequence represented by SEQ ID NO: 2 or 4 may be a protein having one or a few amino acids deleted, substituted or added, as long as hyaluronic acid synthase activity is not lost. For example, the amino acid sequence represented by SEQ ID NO: 2 or 4 may have a deletion of at least one amino acid, preferably 1 to 10 amino acids, more preferably 1 to 5 amino acids, an addition of at least one amino acid, preferably 1 to 10 amino acids, more preferably 1 to 5 amino acids, or a substitution of at least one amino acid, preferably 1 to 10 amino acids, more preferably 1 to 5 amino acids by other amino acids. However, mutations are not limited to the above. Such mutations include artificial mutations other than naturally occurring mutations. For example, it is reported that hyaluronic acid synthase derived from *Pasteurella multocida* has hyaluronic acid synthase activity even if about 270 amino acids in the putative membrane-bound domain and the putative transmembrane domain are deleted (Jing et al., 2000, Glycobiology, 10, 883-889). The number of mutated amino acids is not limited, as long as the hyaluronic acid synthase activity is not lost. HAS may be a protein consisting of a part of the amino acid sequence represented by SEQ ID NO: 2 or 4, having hyaluronic acid synthase activity.

Hyaluronic acid synthase activities are determined as follows. For the reaction, samples are incubated in 0.2 ml of 50 mM Tris-HCl buffer (pH7.0) containing 1 mM dithiothreitol, 20 mM magnesium chloride, 1 mM ethylene glycol bis (β-aminoethyl ether)-N,N,N,N-tetra-acetic acid, 15% glycerol, 0.5 mM uridine-5'-diphosphoglucuronic acid (hereinafter abbreviated as UDP-GlcA), 0.5 mM uridine-5'-diphospho-N-acetylglucosamine (hereinafter abbreviated as UDP-GlcNAc below), 0.1 μM UDP-[14C]GlcA, 0.24 μM UDP-[3H]GlcNAc, and 125 μg of glucuronic acid for 1 hour. After the incubation, the reaction is terminated by boiling for 10 minutes. The reaction mixture is divided into two, 0.5 units of hyaluronidase (Seikagaku Corporation) derived from *Streptococcus dysgalactiae* is added to one of the solutions, and then incubated at 30° C. for 4 hours. Then the reaction solution is boiled for 10 minutes to inactivate the hyaluronidase. The reaction mixture is fractionated per 0.5 ml using Superdex Peptide HR10/30 (produced by Amarsham Pharmacia Biotech Inc.) column chromatography (elute: 0.2M ammonium acetate). Each fraction is measured for radioactivity. As a result, hyaluronic acid activity can be determined from the sample reaction mixture based on the amounts of low-molecular-weight products digested by the hyaluronidase. Hyaluronic acid synthase activity can be also determined using the sandwich method, in which hyaluronic acid produced is measured using hyaluronic acid binding proteins.

According to the present invention, the DNA encoding a protein with hyaluronic acid synthase and is DNA encoding a protein that synthesizes hyaluronic acid from UDP-glucuronic acid and UDP-N-acetylglucosamine as substrates, wherein the hyaluronic acid has a polymer structure consisting of repeated units of glucuronic acid and N-acetylglucosamine.

According to the present invention, the DNA encoding a protein with hyaluronic acid synthase activity is, as long as the protein has the above mentioned properties, not particularly limited. Hyaluronic acid synthase (hereinafter occasionally abbreviated as HAS) genes derived from animals, microorganisms, virus and the like can be used. For example, the hyaluronic acid synthase gene derived from vertebrates such as humans, mice, rabbits, chickens, cattle and *Xenopus laevis*, microorganisms such as *Streptococcus* and *Pasteurella*, and viruses such as chlorella virus and the like, can be used.

More specifically, HAS (A98R) genes derived from chlorella virus strain PBCV-1; HAS1, HAS2 and HAS3 of the hyaluronic acid synthase (hHAS) gene derived from humans; HAS1, HAS2 and HAS3 of the mouse derived hyaluronic acid synthase (mHAS) gene; HAS1, HAS2 and HAS3 of the chicken derived hyaluronic acid synthase (gHAS) gene; HAS2 of the rat derived hyaluronic acid synthase (rHAS) gene; HAS2 of the cattle derived hyaluronic acid synthase (bHAS) gene; HAS1, HAS2 and HAS3 of the *Xenopus laevis* derived hyaluronic acid synthase (xHAS) gene; the *Pasteurella multocida* derived hyaluronic acid synthase (pm- HAS) gene; the *Streptococcus pyogenes* derived hyaluronic acid synthase (spHAS) gene; the hyaluronic acid synthase (seHAS) gene derived from *Streptococcus equisimilis* and the like are included. There are various types of hyaluronic acid synthase (HAS) genes such as HAS1, HAS2 and HAS3, however, the type is not particularly limited.

Any of the above described HAS can be used, among which the chlorella virus derived HAS gene is preferable, chlorella virus derived HAS genes which are shown by DNA consisting of a nucleotide sequence represented by SEQ ID NO: 1 or 3 are more preferable.

The DNA may be DNA that hybridizes with DNA consisting of the nucleotide sequence complementary to the nucleotide sequence represented by SEQ ID NO: 1 or 3 under stringent conditions, and encodes a protein with hyaluronic acid synthase activity.

The term "stringent conditions" above means conditions in which only a nucleotide sequence that encodes a polypeptide having hyaluronic acid synthase activity that is equivalent to that of hyaluronic acid synthase having a nucleotide sequence represented by SEQ ID NO: 1 or 3 forms a hybrid with the particular sequence (that is a specific hybrid), whereas a nucleotide sequence that encodes a polypeptide having non-equivalent activity does not form a hybrid with the particular sequence (that is a non-specific hybrid). Persons skilled in the art can easily choose such conditions by changing the temperatures of the hybridization reaction and washing, and the salt concentrations of hybridization reaction solutions and washing solutions, and the like. Specifically, one example of the stringent conditions of the present invention is the conditions in which hybridizing is performed in 6×SSC (0.9M NaCl, 0.09M trisodium citrate) or 6×SSPE (3M NaCl, 0.2M $NAH_2PO_4$, 20 mM EDTA.2Na, pH7.4) at 42° C., and further washing is performed using 0.5×SSC at 42° C., however, the stringent conditions are not limited to such conditions.

The stringent conditions are preferably highly stringent conditions. The highly stringent conditions are not particularly limited, as long as a gene encoding A98R does not hybridize. For example, the highly stringent conditions are conditions in which washing is performed in salt concentrations equivalent to that of 0.1×SSC or 0.1% SDS at 60° C.

Sugar Nucleotide

Examples of usable sugar nucleotides are UDP-N-acetylglucosamine, UDP-glucuronic acid, UDP-N-acetylgalactosamine, UDP-glucose, UDP-galactose, UDP-xylose, GDP-fucose, GDP-mannose, CMP-neuraminic acid, and the like, however, the sugar nucleotide is not limited to these. Among these sugar nucleotides, UDP sugar is preferable, UDP-N-acetylglucosamine and UDP-glucuronic acid are more preferable.

By improving the production levels of such sugar nucleotides, the amounts of UDP-glucuronic acid and UDP-N-acetylglucosamine that are substrates for hyaluronic acid synthase are increased in plant cells or plants. To improve the production levels of such sugar nucleotide, a sugar nucleotide biosynthetic pathway enzyme, that is, a protein with sugar-nucleotide synthase activity is introduced into plant cells or plants.

Furthermore, in the present invention, it is found that simultaneous introduction of a protein with hyaluronic acid synthase activity into plant cells or plants enables increased hyaluronic acid synthesis using the increased UDP-glucuronic acid and UDP-N-acetylglucosamine as substrates, wherein the hyaluronic acid has a polymer structure consisting of repeated units of glucuronic acid and N-acetylglucosamine.

Enzymes Associated with Sugar Nucleotide Biosynthesis Pathway

According to the present invention, plant cells or plants are transformed with DNA encoding a protein with hyaluronic acid synthase activity and DNA encoding a protein with sugar-nucleotide synthase activity under the control of a promoter(s) capable of functioning in plants.

Proteins with sugar-nucleotide synthase activity such as UDP-N-acetylglucosamine, UDP-glucuronic acid, UDP-N-acetylgalactosamine, UDP-glucose, UDP-galactose, UDP-xylose, GDP-fucose, GDP-mannose and CMP-neuraminic acid may be used. Proteins having synthase activity directed to, among these sugar nucleotides, UDP-N-acetylglucosamine, UDP-glucuronic acid, UDP-N-acetylgalactosamine, UDP-glucose, UDP-galactose, UDP-xylose are preferable. Proteins having sugar-nucleotide synthase activity directed to sugars, UDP-N-acetylglucosamine and UDP-glucuronic acid are more preferable.

The protein having sugar-nucleotide synthase activity of the present invention may be an enzyme catalyzing the reactions that are associated with sugar nucleotide biosynthesis pathways. Examples of the enzymes are glutamine:fructose-6-phosphate amidotransferase, UDP-N-acetylglucosamine diphosphorylase, phosphoacetyl glucosamine mutase, glucosamine-6-phosphate N-acetyltransferase, glucosamine-1-phosphate-N-acetyltransferase, phosphoglucomutase, N-acetylglucosamine kinase, hexokinase, N-acetylglucosamine acetylase, UDP-glucose dehydrogenase, UDP-glucose-1-phosphate uridyltransferase, inositol oxygenase, glucuronokinase, glucuronate-1-phosphate uridyl transferase and the like. At least one protein selected from the group consisting of such proteins with sugar-nucleotide synthase activity may be expressed in plant cells or plants.

As a protein with sugar-nucleotide synthase activity, at least glutamine:fructose-6-phosphate amidotransferase may also be selected, and expressed in combination with a protein having other sugar-nucleotide synthase activity in plant cells or plants. Examples of other proteins having sugar-nucleotide synthase activity than glutamine:fructose-6-phosphate amidotransferase are at least one amino-acid protein selected from the group consisting of UDP-N-acetylglucosamine diphosphorylase, phosphoacetyl glucosamine mutase, glucosamine-6-phosphate N-acetyltransferase, glucosamine-1-phosphate N-acetyltransferase, phosphoglucomutase, N-acetylglucosamine kinase, hexokinase, N-acetylglucosamine acetylase, UDP-glucose dehydrogenase, UDP-glucose-1-phosphate uridyltransferase, inositol oxygenase, glucuronokinase, glucuronic acid-1-phosphate uridyl transferase and the like.

To achieve the intended effects of the present invention, at least, glutamine:fructose-6-phosphate amidotransferase is selected as a protein having the sugar-nucleotide synthase activity, thereby a better effect than that of conventional methods is obtained. More preferably, both of glutamine:fructose-6-phosphate amidotransferase (hereinafter occasionally abbreviated as GFAT) and UDP-glucose dehydrogenase (hereinafter occasionally abbreviated as UGD) are selected. The single use of UDP-glucose dehydrogenase also shows more enhanced effects than that of conventional methods.

Glutamine:Fructose-6-Phosphate Amidotransferase

The protein having glutamine:fructose-6-phosphate amidotransferase activity of the present invention is a protein that synthesizes glucosamine-6-phosphate from L-glutamine and fructose-6-phosphate as substrates.

The protein having glutamine:fructose-6-phosphate amidotransferase activity of the present invention is, as long as the protein has the above mentioned nature, not particularly limited. Examples of such proteins are GFAT derived from eukaryotes, prokaryotes, viruses and the like. GFAT derived from eukaryotes such as humans, mice, cornes, *Arabidopsis thaliana*, *Caenorhabditis elegans* and *Saccharomyces cerevisiae*, GFAT derived from prokaryotes such as *Bacillus subtilis* and *Escherichia coli*, and GFAT derived from viruses such as chlorella virus can be used, however, the protein is not limited to these.

The GFAT above can be preferably used, among which the GFAT derived from chlorella virus or *Arabidopsis thaliana* is more preferable. The chlorella virus derived GFAT shown by a protein consisting of the amino acid sequence represented by SEQ ID NO: 6 or 8, and the *Arabidopsis thaliana* derived GFAT shown by a protein consisting of an amino acid sequence represented by SEQ ID NO: 10 are especially preferable.

The protein may also be a protein consisting of the amino acid sequence represented by SEQ ID NO: 6, 8 or 10, or the protein with one or a few amino acids deleted, substituted or added to its amino acid sequence as long as the glutamine:fructose-6-phosphate amidotransferase activity is not lost. For example, the amino acid sequence represented by SEQ ID NO: 6, 8 or 10 may have a deletion of at least one amino acid, preferably 1 to 10 amino acids, and more preferably 1 to 5 amino acids. The amino acid sequence represented by SEQ ID NO: 6, 8 or 10 may have an addition of at least one amino acid, preferably 1 to 10 amino acids, more preferably 1 to 5 amino acids. The amino acid sequence represented by SEQ ID NO: 6, 8 or 10 may have a substitution of at least one amino acid, preferably 1 to 10 amino acids, more preferably 1 to 5 amino acids, and more preferably 1 to 5 amino acids, with other amino acids. However, mutations are not limited to the aforementioned examples. Such mutations include artificial mutations other than naturally occurring mutations. The number of mutated amino acids is, as long as the GFAT activity is not lost, not particularly limited. An example of naturally occurring mutations is the GFAT derived form chlorella virus strain Hirosaki and having a sequence of SEQ ID NO: 5 that departs from known GFAT of chlorella virus strain PBCV-1 and K21 at least by 2% in their amino acid sequences due to mutation. The protein may be a protein having a part of the amino acid sequence represented by SEQ ID NO: 6, 8 or 10, and having glutamine:fructose-6-phosphate amidotransferase activity.

The Glutamine:fructose-6-phosphate amidotransferase activity can be evaluated by adding the enzyme solution to reaction mixture (pH7.0) containing fructose-6-phosphate (15 mM), L-glutamine (15 mM), EDTA (1 mM), DTT (1 mM) and $KH_2PO_4$ (60 mM), and then incubating at 37° C. for a few hours, and subsequently measuring the amount of glucosamine-6-phosphate or glutamic acid produced. Specifically, examples of the methods are the Reissig method (J. Biol. Chem, 1955, 217(2), 959-66), which is a modified version of the Morgan & Elson method for measuring glucosamine-6-phosphate; enzymatic analysis (J Biochem Biophys Methods, 2004, 59(3), 201-8) for measuring glutamic acid using glutamic acid dehydrogenase; and the like.

DNA encoding a protein with glutamine:fructose-6-phosphate amidotransferase activity of the present invention is DNA encoding a protein that has enzyme activity to synthesize glucosamine-6-phosphate from L-glutamine and fructose-6-phosphate as substrates.

DNA encoding a protein with glutamine:fructose-6-phosphate amidotransferase activity of the present invention is, as long as the proteins have the above mentioned properties, not particularly limited. Examples of such GFAT genes are GFAT genes derived from eukaryotes, prokaryotes, viruses and the like. GFAT genes derived from eukaryotes such as humans, mice, corns, *Arabidopsis thaliana*, *Caenorhabditis elegans* and *Saccharomyces cerevisiae*, GFAT genes derived from prokaryotes such as *Bacillus subtilis* and *Escherichia coli*, GFAT genes derived from viruses such as chlorella virus and the like can be used. There are various types of GFAT genes such as GFAT1 and GFAT2, however, the type is not particularly limited.

The above described GFAT genes can be preferably used, among which the GFAT gene derived from Chlorella virus or derived from *Arabidopsis thaliana* is more preferable. The GFAT gene derived from Chlorella virus and consisting of the nucleotide sequence represented by SEQ ID NO: 5 or 7, or the GFAT gene derived from *Arabidopsis thaliana* and consisting of the nucleotide sequence represented by SEQ ID NO: 9 is especially preferable.

The DNA may also be DNA hybridizing with a nucleotide sequence complementary to the nucleotide sequence represented by SEQ ID NO: 5, 7 or 9 under stringent conditions, and encoding a protein with GFAT activity.

The term "stringent conditions" above means conditions in which only a nucleotide sequence encoding a polypeptide with a glutamine:fructose-6-phosphate amidotransferase activity equivalent to that of glutamine:fructose-6-phosphate amidotransferase represented by SEQ ID NO: 5, 7 or 9 forms a hybrid with the particular sequence (i.e., a specific hybrid), whereas a nucleotide sequence encoding a polypeptide with non-equivalent activity does form a hybrid with the particular sequence (i.e., a non-specific hybrid). Persons skilled in the art can easily choose such conditions by changing temperatures for the hybridization reaction and washing, salt concentrations of hybridization reaction solutions and washing solutions, and the like. One example of the stringent conditions of the present invention is conditions in which hybridization is performed using 6×SSC (0.9M NaCl, 0.09M trisodium citrate) or 6×SSPE (3M NaCl, 0.2M $NAH_2PO_4$, 20 mM EDTA.2Na, pH7.4) at 42° C., and subsequently washing is performed using 0.5×SSC at 42° C., however, the stringent conditions are not limited to these.

The stringent conditions are preferably highly stringent conditions. The "highly stringent conditions" are for example, conditions in which washing is performed in salt concentrations equivalent to that of 0.1×SSC and 0.1% SDS at 60° C.

UDP-Glucose Dehydrogenase

The protein having UDP-glucose dehydrogenase activity of the present invention may be a protein that synthesizes UDP-glucuronic acid from UDP-glucose as a substrate.

The protein having UDP-glucose dehydrogenase activity of the present invention is, as long as the protein has the above-mentioned nature, not particularly limited. Examples of the proteins are UGD derived from eukaryotes, prokaryotes, viruses and the like. UGD derived from eukaryotes such as UGD derived from humans, cattle mice, poplars, sugarcanes and *Arabidopsis thaliana* UGD derived from prokaryotes such as *Escherichia coli, Pasteurella multocida* and *Lactobacillus lactis*, and UGD derived from viruses such as chlorella virus can be used, however, the protein of the invention is not limited to these.

The UGD described above can be preferably used, among which UGD derived from chlorella virus or *Arabidopsis thaliana* is more preferable. UGD derived from chlorella virus and shown by a protein consisting of an amino acid sequence represented by SEQ ID NO: 12 or 14, or UGD derived from *Arabidopsis thaliana* shown by a protein consisting of an amino acid sequence represented by SEQ ID NO: 16, 18, 20 or 22 is particularly preferable.

The protein may be a protein consisting of the amino acid sequence represented by SEQ ID NO: 12, 14, 16, 18, 20, or 22, or a protein having a mutation such as a deletion of one or a few amino acids, a substitution, or an addition as long as the UDP-glucose dehydrogenase activity is not lost. For example, the amino acid sequence represented by SEQ ID NO: 12, 14, 16, 18, 20, or 22 may have a deletion of at least one amino acid, preferably 1 to 10 amino acids, and more preferably 1 to 5 amino acids. The amino acid sequence represented by SEQ ID NO: 12, 14, 16, 18, 20, or 22 may have an addition of at least one amino acid, preferably 1 to 10 amino acids, and more preferably 1 to 5 amino acids. The amino acid sequence represented by SEQ ID NO: 12, 14, 16, 18, 20, or 22 may also have a substitution of at least 1 amino acid, preferably 1 to 10 amino acids, and more preferably 1 to 5 amino acids by other amino acids. However, the mutations are not limited to the above. Such mutations also include artificial mutations other than naturally occurring mutations. The number of mutated amino acids is not particularly limited, as long as the UGD activity is not lost. The protein may also be a protein having a part of the amino acid sequence represented by SEQ ID NO: 12, 14, 16, 18, 20, or 22, and having UDP-glucose dehydrogenase.

UDP-glucose dehydrogenase activity is evaluated by adding the enzyme solution to reaction mixture (pH 8.0) containing UDP-glucose (4 mM), NAD+ (1 mM), EDTA (1 mM) and Tris-HCl (20 mM), performing the reaction at 37° C., and subsequently measuring the UDP-glucuronic acid or NADH produced. Specifiacally, NADH can be measured according to Tenhaken and Thulke's report (Plant Physiol. 1996, 112: 1127-34).

The DNA encoding a protein with UDP-glucose dehydrogenase activity of the present invention is DNA encoding a protein that has enzyme activity to synthesize UDP-glucuronic acid from UDP-glucose as a substrate.

The DNA encoding a protein with UDP-glucose dehydrogenase activity of the present invention is, as long as the protein has the above-mentioned nature, not particularly limited. Examples of the DNA are UGD genes derived from eukaryotes, prokaryotes, viruses and the like. UGD genes derived from eukaryotes such as humans, cattle, mice, poplars, sugarcanes and *Arabidopsis thaliana*, UGD genes derived from prokaryotes such as *Escherichia coli*, *Pasteurella multocida* and *Lactobacillus lactis*, and UGD genes derived from viruses such as chlorella virus and the like can be used, however, the UGD genes are not limited to these.

The UGD genes described above can be preferably used, among which UGD gene derived from chlorella virus or *Arabidopsis thaliana* is more preferable, UGD gene derived from chlorella viruses and having a nucleotide sequence represented by SEQ ID NO: 11, or 13 or UGD gene derived from *Arabidopsis thaliana* having a nucleotide sequence represented by SEQ ID NO: 15, 17, 19 or 21 is particularly preferable.

The DNA may be DNA hybridizing with DNA consisting of a nucleotide sequence complementary to the nucleotide sequences represented by SEQ ID NO: 11, 13, 15, 17, 19, or 21 under stringent conditions, and encoding a protein with UDP-glucose dehydrogenase activity.

The "stringent conditions" described above are conditions in which only a nucleotide sequence encoding a polypeptide with the activity equivalent to that of UDP-glucose dehydrogenase represented by SEQ ID NO: 11, 13, 15, 17, 19, or 21 forms a particular hybrid with the particular sequence (i.e., a specific hybrid), whereas a nucleotide sequence encoding a polypeptide with non-equivalent activity does not form a hybrid with the particular sequence (i.e., a non-specific hybrid). Persons skilled in the art can easily choose such conditions by changing the temperatures for hybridization reaction and washing, adjusting the salt concentrations of the hybridization reaction solutions and washing solutions, and the like. One example of stringent conditions is conditions in which hybridization is performed using 6×SSC (0.9M NaCl, 0.09M trisodium citrate) or 6×SSPE (3M NaCl, 0.2M $NAH_2PO_4$, 20 mM EDTA).2Na, pH7.4) at 42° C., and then washing is performed using 0.5×SSC. However, the stringent conditions are not limited to these.

The stringent conditions are preferably highly stringent conditions. Highly stringent conditions are, for example, conditions in which washing is performed in salt concentrations equivalent to that of 0.1×SSC or 0.1% SDS at 60° C.

A Recombinant Expression Vector and Transformation

Transgenic plant cells or transgenic plants capable of producing hyaluronic acid, progenies, or organs or tissues thereof having the same nature thereof can be obtained by transforming hosts using a recombinant expression vector. The recombinant expression vector contains DNA encoding a protein with hyaluronic acid synthase activity and DNA encoding a protein with sugar-nucleotide synthase activity under the control of a promoter(s) capable of functioning in plants.

A protein having hyaluronic acid synthase activity and a protein with sugar-nucleotide synthase activity are expressed in the above transgenic plant cells or the transgenic plants, the progenies, or the organs or the tissues thereof having the same nature thereof.

"An exogenous protein with sugar-nucleotide synthase activity" is, unlike an endogenous protein, a foreign protein having sugar nucleotide synthase activity and being newly introduced into plant cells or plants from outside. An example of a method for "newly introducing such a gene from outside" includes transformation using a recombinant expression vector and the like. "Newly introducing a gene from outside" includes transforming an endogenous gene from outside of the cell using a recombinant expression vector. Since there have been no proteins with hyaluronic acid synthase activity found in plant cells and plants, it is obvious that the protein is exogenous without the description.

The above transgenic plant cells or transgenic plants, the progenies, or the organs or tissues thereof having the same nature thereof enable high-level production of hyaluronic acid. This is demonstrated below.

In the present invention, the hosts mean any whole plants, seeds, plant organs (for example, petals, roots, stems, stem tubers, leaves, floral organs, tuberous roots, seeds, shoot apices and the like), plant tissues (for example, epidermis, phloem, soft tissues, xylem, vascular bundles and the like), or cultured plant cells.

In the present specification, plants mean any multicellular plants including spermatophytes, gymnosperms, pteridophytes, bryophytes, lichenes and the like, and include any whole plants, seeds, plant organs (for example, petals, roots, stems, stem tubers, leaves, floral organs, tuberous roots, seeds, shoot apices and the like), plant tissues (for example, epidermis, phloem, soft tissues, xylem, vascular bundles and the like), or cultured plant cells.

Hyaluronic acid may also be produced thus by culturing the transformants resulting from the transformation, and isolating the produced hyaluronic acid thereby.

Vectors that are generally used for producing transgenic plant cells or transgenic plants can be used as recombinant expression vectors.

Such vectors are not particularly limited as long as the vectors comprise a promoter sequence capable of being transcribed in plant cells and a polyadenylation site required for stabilizing transcripts. For example, vectors such as "pBI121", "pBI221", "pBI101" and "pIG121Hm" can be used.

When cultured plant cells are used as hosts, transformation can be achieved by introducing a recombinant expression vector for producing hyaluronic acid in cultured plant cells by the electroporation method, the *Agrobacterium* binary vector method or the Particle Bombardment method. The vector includes DNA encoding a protein with hyaluronic acid synthase activity and DNA encoding a protein with sugar-nucleotide synthase activity placed under the control of a promoter(s) capable of functioning in plants. The plant cells in which the expression vector has been introduced are, for example, selected on the basis of resistance to antibiotics such as kanamycin and the like. The transformed plant cells can be used for cell culture, tissue culture and organ culture. It is also possible to regenerate plants using a previously known plant tissue culture method.

Examples of plant cells subjected to the transformation include BY-2 cells and T-13 cells derived from tobacco, kurodagosun cells derived from carrots, VR cells and VW cells derived from grapes, PAR cells, PAP cells and PAW cells derived from *Phytolacca americana* L., T87 cells derived from *Arabidopsis thaliana*, Asp-86 cells, A. per cells, A. pas cells and A. plo cells derived from asparagus, Cba-1 cells derived from watermelon, Sly-1 cells derived from tomatoes, 1-Mar cells derived from peppermint, CRA cells and V208 cells derived from Madagascar periwinkle, Spi-WT cells, Spi-I-1 cells and Spi-12F cells derived from spinach, Lcy-1 cells, LcyD6 cells and LcyD7 cells derived from gourds, OS-1 cells derived from *Oryza sativa*, Vma-1 cells derived from *Vinca rosea*, PSB cells, PSW cells and PSG cells derived from sesame, and ZE3 cells derived from *Zinnia elegans*.

When cultured plant cells are used as hosts, transformation is performed by introducing a recombinant expression vector for producing hyaluronic acid into the plant by the *Agrobacterium* binary vector method, the Particle Bombardment method or the electroporation method into protoplasts, where the vector includes DNA encoding a protein with hyaluronic acid synthase activity and DNA encoding a protein with sugar-nucleotide synthase activity under the control of a promoter(s) capable of functioning in plants, and then isolating the tumor tissues, shoots, hair roots and the like resulting from the transformation.

Tumor tissues, shoots, hair roots and the like obtained as described above can be directly used for cell culture, tissue culture or organ culture. These transformants can also be regenerated into plants by previously known plant tissue culture methods, by applying plant hormones in appropriate concentrations and the like.

To regenerate a plant from a cell into which a hyaluronic acid synthase gene has been introduced, such a plant cell may be cultured on a regeneration medium, a hormone-free MS medium or the like. The resultant rooting young plant can be planted in soil and grown. Methods for regeneration differ depending on the type of the plant cell, but it is possible to use a previously known method for plant tissue culture.

For example, the method of Fujimura et al. (Fujimura et al. (1955), Plant Tissue Culture Lett., Vol. 2: p. 74) can be used for *Oryza sativa*, the method of Shillito et al. (Shillito et al. (1989), Bio/Technology, Vol. 7: p. 581, and Gorden-Kamm (1990), Plant Cell, 2, 603) can be used for maize, and the method of Visser et al. (Visser et al. (1989), Theor. Appl. Genet, Vol. 78: p 589) can be used for potatoes. The method of Nagata et al. (Nagata et al. (1971), Planta 99, 12) can be used for tobacco, and the method of Akama et al. (Akama et al. (1992), Plant Cell Rep., Vol. 12: p. 7) can be used for *Arabidopsis thaliana*.

Plants produced by such methods, or the progenies; for example, plants regenerated from seeds, stem tubers, cutting and the like) having the same nature thereof, are also objectives of the present invention.

In order to produce a protein with hyaluronic acid synthase activity and a protein having sugar-nucleotide synthesize activity in plants, and further to produce and accumulate or secrete hyaluronic acid, DNA encoding a protein with hyaluronic acid synthase activity and DNA encoding a protein with sugar-nucleotide synthase activity are preferably placed under the control of a promoter(s) capable of functioning in plants, so that the DNA is specifically expressed in the desired tissues or organs.

For the expression to be controlled as such, a tissue specific- or an organ-specific promoter may be further inserted into a recombinant expression vector.

If a stage-specific promoter is used instead, a target gene can be expressed only during a particular period. Therefore, productivity can be improved only during the particular period. For example, use of a vegetative stage-specific promoter improves productivity only during the vegetative stage.

Examples of organ-specific promoters are root-specific promoters, tuber-promoters tuber-specific promoters, leaf-specific promoters, seed-specific promoters, stem-specific promoters and the like.

Examples of tissue-specific promoters are green tissue-specific promoters and the like.

More specifically, usable promoters include constitutively high expression promoters such as a CaMV35S promoter, which is a promoter of the cauliflower mosaic virus 35S RNA, and the like. Green tissue-specific promoters include, for example, a rbs promoter for a gene encoding the small subunit protein of ribulose-1,5-bisphosphate carboxylase, a CAB promoter for a gene encoding the chlorophyll a/b-binding protein, and a GapA promoter for a gene encoding encoding the A subunit protein of glyceraldehyde-3-phosphate dehydrogenase. Seed-specific promoters include a LOX promoter of the lipoxygenase gene, a Psl promoter of the lectin gene, an AmylA promoter of the amylase gene, and the like. Root-specific promoters include a A6H6H promoter of the hyoscyamine 6b-hydroxylase gene, a PMT promoter of the putrescine N-methyltransferase, and the like. Stem-specific promoters include a Sus4 promoter of the sucrose synthase, a patatin promoter for a gene encoding the glycoprotein, and the like.

It is also conceivable to control the expression of DNA encoding a protein with hyaluronic acid synthase activity and DNA encoding a protein with sugar-nucleotide synthase activity using an inducible promoter. Examples of the induction promoters are described below.

Examples of inducible promoters include a PR1a promoter, which is a promoter of a disease resistance related gene whose expression level is enhanced by injury or an addition of salicylic acid, and an rd29A promoter whose expression level is enhanced by dryness, low temperature, high salt concentration, addition of abscisic acid and the like. Examples of promoters whose expression is induced by compounds used as agricultural chemicals include a GST-27 promoter for a gene encoding a 27 KDa subunit protein of glutathion-S-transferase and is induced by herbicide safeners, a kinase promoter and a PR promoters for genes being induced by benzo(1,2,3)-thiadiazole-7-carbothioic acid S-methyl ester (BTH). In addition, in order to more stably express DNA encoding a protein with hyaluronic acid synthase activity and DNA encoding a protein with sugar-nucleotide synthase activity in plant cells, insulators may be utilized, a signal peptide may be added to localize the a protein with hyaluronic acid synthase activity and a protein with sugar-nucleotide synthase activity in a target organelle, a part of hyaluronic acid synthase may be substituted or deleted, and the like.

The plants subjected to transformation include any plants in which gene transfer is possible.

The plants or the plant bodies of the present invention include monocotyledons and dicotyledons of angiosperms, and gymnosperms. Such plants include optionally useful plants, particularly crop plants, vegetable plants, flower plants and woody plants.

The plants or the plant bodies of the present invention also include pteridophytes and bryophytes.

Examples of plant species usable in the present invention specifically include plants belonging to the families Solanaceae, Gramineae, Cruciferae, Rosaceae, Leguminosae, Cucurbitaceae, Labiatae, Liliaceae, Chenopodiaceae, Umbeliferae, Myrtaceae, Convolvulaceae, and like.

Examples of plants belonging to Solanaceae include the plants belonging to the genus *Nicotiana, Solanum, Datura, Lycopersion* or *Petunia*, and, for example, include tobacco, eggplants, potatoes, tomatoes, chili peppers, petunias and the like.

Examples of plants belonging to Gramineae include the plants belonging to the genus *Oryza, Hordeum, Secale, Saccharum, Echinochloa* or *Zea*, and, for example, include *Oryza sativa*, barley, rye, cockspur, Sorghums, corn, sugarcane and the like.

Examples of plants belonging to Cruciferae include the plants belonging to the genus *Raphanus, Brassica, Arabidopsis, Wasabia* or *Capsella*, and, for example, include daikon radish, rapeseed, *Arabidopsis thaliana*, Japanese horseradish, Shepherd's Purse and the like.

Examples of plants belonging to Rosaceae include the plants belonging to the genus *Orunus, Malus, Pynus, Fragaria* or *Rosa*, and, for example, include Japanese apricots, peaches, apples, pears, strawberry, roses and the like.

Examples of plants belonging to Leguminosae include the plants belonging to the genus *Glycine, Vigna, PHASeolus, Pisum, Vicia, Arachis, Trifolium, Alfalfa* or *Medicag*, and, for example, include soy beans, adzuki beans, butter beans, peas, fava beans, peanuts, clovers, bur clovers and the like.

Examples of plants belonging to Cucurbitaceae include the plants belonging to the genus *Luffa, Cucurbita* or *Cucumis*, and, for example, include gourds, pumpkins, cucumber, melons and the like.

Examples of plants belonging to Labiatae include the plants belonging to the genus *Lavadula, Mentha* or *Perilla*, and, for example, include lavender, mint, Japanese basil and the like.

Examples of plants belonging to Liliaceae include the plants belonging to the genus *Allium, Lilium* or *Tulipa*, and, for example, include Welsh onions, garlic, lilies, tulips and the like.

Examples of plants belonging to Chenopodiaceae include the plants belonging to the genus *Spinacia*, and, for example, include sugar beets, spinach and the like.

Examples of plants belonging to Umbelliferae include the plants belonging to the genus *Angelica, Daucus, Cryptotaenia* or *Apitum*, and, for example, include shishiudos, carrots, hornworts, celeries and the like.

Examples of plants belonging to Convolvulaceae include the plants belonging to the genus *Ipomoea*, and, for example, include sweet potatoes and the like.

The progenies having the same nature as the above transgenic plants, or the organs or tissues thereof are also the subjects of the present invention.

The transgenic plant cells which produce a protein with hyaluronic acid synthase activity and a protein having a sugar-nucleotide synthase activity are included in the present invention. The transgenic plants which produce a protein having hyaluronic acid synthase activity and a protein having sugar-nucleotide synthase activity, the progenies having the same nature thereof, or the organs or tissues thereof, are also included.

Extraction of Hyaluronic Acid

Below is an example of methods for isolating or obtaining hyaluronic acid by co-expressing a protein with hyaluronic acid synthase activity and an exogenous protein having an activity of synthesizing the sugar nucleotide, and extracting hyaluronic acid from the transgenic plant cells or the transgenic plants that have acquired the ability to produce hyaluronic acid, progenies, or organs or tissues thereof having the same nature thereof.

The transgenic plant cells or the transgenic plants are cultured or grown, the hyaluronic acid is produced, and subsequently, the hyaluronic acid is optionally extracted from the transgenic plant cells or the transgenic plants by a known method. The extracts are checked for hyaluronic acid.

For example, the transgenic plants, the progenies having the same nature thereof, the organs or the tissues thereof, or the like can be subsequently dried, grinded and then extracted by an appropriate organic solvent. The extract containing the hyaluronic acid is filtrated, and a filtrate containing hyaluronic acid and no plant cells is obtained. This filtrate is purified by diafiltration to remove low-molecular-weight impurities. It is possible to separate the hyaluronic acid by the diafiltration of the filtrate containing dissolved hyaluronic acid with pure water followed by continuously discarding the filtrate. When hyaluronic acid is used in pharmaceuticals, a step of precipitating nucleic acids from the solution may be further performed. This step can be, for example, performed by adding cation surfactant such as quaternary ammonium compounds of cetylpyridinium chloride.

Hyaluronic acid accumulated in the transformed plant cells may be also purified by known methods for the separation.

Use of Hyaluronic Acid

Hyaluronic acid acquired by the present invention can be usefully utilized for cosmetic and pharmaceutical compositions, or biomaterials. Specifically, hyaluronic acid can be used as a moisturizing composition in cosmetics, a therapeutic agent for arthritis, chronic rheumatism, burns and cuts, or a component in eye drops.

Hyaluronic acid obtained by the production method of the present invention may be used as an active agent to make cosmetic compositions. For example, hyaluronic acid can be applied in liquid forms such as aqueous solutions, oil solutions, emulsions and suspensions, in semi-solid forms such as gels and creams, and in solid forms such as powders, granules, capsules, microcapsules and solids. Hyaluronic acid can be prepared into those forms using known methods, and made in the formulation of lotions, emulsions, gels, creams, ointments, emplastrums, cataplasms, aerosols, suppositories, injections, powders, granules, tablets, pills, syrups, troches and the like. Such formulations can be applied by applying, attaching, spraying, drinking and the like. Particularly among those formulations, lotions, emulsions, creams, ointments, emplastrums, cataplasms, aerosols and the like are suitable for skin applications. For cosmetics, hyaluronic acid can be used for skin care cosmetics such as lotions, serums, emulsions, creams and masks, makeup cosmetics such as makeup base lotions, makeup creams, foundations in emulsions, cream and ointment forms, lipsticks, eye shadows and cheek colors, body care cosmetics such as hand creams, leg creams, body lotions and the like, bath essences, oral care cosmetics and hair care cosmetics. Hyaluronic acid can be produced into such formulations according to the general method for making cosmetics.

EXAMPLES

The following Examples illustrate the present invention in further detail, but are not intended to limit the scope of the invention.

Example 1

Isolation of *Arabidopsis-thaliana*-Derived UGD Gene

A UDP-glucose dehydrogenase (BT006380:AtUGD1, SEQ ID NO: 15) gene has been isolated from *Arabidopsis thaliana* and shown to have activity (Plant J. 2000 21(6):537-46). Further, the NCBI BLAST (www.ncbi.nlm.nih.gov/BLAST/) database shows three types of *Arabidopsis-thaliana*-derived genes that are predicted to encode UGD (AF424576:AtUGD2 (SEQ ID NO: 17), AY056200: AtUGD3 (SEQ ID NO: 19), and AY070758:AtUGD4 (SEQ ID NO: 21)). These four types of UGD genes were cloned to confirm their UGD activity.

RNA was extracted from *Arabidopsis thaliana* according to the RNeasy (QIAGEN) protocol. For a reverse transcription reaction, 2 μg of total RNA was dissolved in 5.5 μL of sterile water, mixed with 1 μL of 10 μM oligo d(T) primer, and thermally denatured at 70° C. for 10 minutes. After rapid cooling, the reverse transcription reaction was performed using a ReverTraAce kit (Toyobo), at 42° C. for 30 minutes and at 99° C. for 5 minutes.

For PCR amplification of the *Arabidopsis-thaliana*-derived UGD genes, PCR primers were designed based on the four nucleotide sequences on the database. Restriction enzyme cleavage sites that are necessary for introduction into the expression vector pMAL-c2 (NewEngland Biolab) were added to the primers. EcoRI or HindIII (SEQ ID NO: 23 or 24) were added to AtUGD1; EcoRI or PstI (SEQ ID NO: 25 or 26) to AtUGD2; EcoRI or PstI (SEQ ID NO: 27 or 28) to AtUGD3; and EcoRI or XbaI (SEQ ID NO: 29 or 30) to AtUGD4. PCR was performed using a KOD-plus-DNA polymerase (Toyobo) and a reaction program of 1 cycle of 94° C. for 2 minutes, 3 cycles of 94° C. for 15 seconds, 45° C. for 30 seconds, and 68° C. for 1 minute, and 30 cycles of 94° C. for 15 seconds, 55° C. for 30 seconds, and 68° C. for 1 minute. One microliter of reverse transcription reaction product was used as template DNA. An agarose gel electrophoresis analysis showed PCR-amplified bands with predicted size. Each PCR-amplified fragment was cleaved with restriction enzymes (AtUGD1: EcoRI and HindIII; AtUGD2 and AtUGD3: EcoRI and PstI; AtUGD4: EcoRI and XbaI), and cloned into pMAL-c2 digested with the same restriction enzymes, using Ligation High (Toyobo). Using the ligation mixture, *Escherichia coli* strain JM109 was transformed by the above-mentioned known method, and the transformants were applied to Luria-Bertani (LB) agar medium (10 g/L bactotryptone, 10 g/L yeast extract, 5 g/L sodium chloride, 15 g/L agar) containing ampicillin (50 μg/mL), and cultured overnight at 37° C. The plasmid was extracted from the grown colonies of transformants using a known method. The nucleotide sequences of the inserted fragments were determined using a DNA sequencer, and it was confirmed that the amplified genes were those represented by SEQ ID NOS: 15, 17, 19, and 21. Thus, the plasmids pMAL-c2/AtUGD1, pMAL-c2/AtUGD2, pMAL-c2/AtUGD3, and pMAL-c2/AtUGD4 were constructed.

The above demonstrates that, in addition to AtUGD1, which has already been reported, three types of UGD genes are expressed in *Arabidopsis thaliana*.

*Escherichia coli* strain JM109 carrying the above expression plasmids were cultured overnight in LB liquid medium containing ampicillin (50 μg/mL) at 37° C. LB medium (30 ml) containing ampicillin (50 μg/mL) and 0.2% glucose was inoculated with 300 μL of the preculture and cultured at 37° C. for 2 hours. The temperature was then lowered to 25° C., isopropyl-β-thiogalactopyranoside (IPTG) at a final concentration of 0.3 mM was added, and expression of the recombinant proteins was induced for 24 hours.

Cells were recovered from 1 mL of the culture medium by centrifugation and disrupted by ultrasonic disintegration to prepare a crude extract. MBP fusion proteins were purified using MagExtractor-MBP-(Toyobo).

FIG. 1 shows the SDS-PAGE analysis of the expressed MBP fusion proteins. A band of the predicted size was observed in all enzyme solutions of the clones.

The UGD activity of the obtained MBP fusion proteins was measured according to the method reported by Tenhaken and Thulke (Plant Physiol. 1996, 112:1127-34). In the method, the increase in NADH caused by UGD reaction is detected as an increase in Abs340. Specifically, 15 μL of the enzyme solution (MBP-UGD fusion protein) was added to a reaction mixture (pH 8.0) containing UDP-glucose (4 mM), NAD+ (1 mM), EDTA (1 mM), and Tris-HCl (20 mM); a reaction was carried out at 37° C.; and the absorbance (Abs340) of the reaction mixture was measured over time. Table 1 shows the enzymatic activity of the MBP fusion proteins.

TABLE 1

|  | U/mg |
| --- | --- |
| AtUGD1 | 2.15 |
| AtUGD2 | 1.32 |
| AtUGD3 | 1.15 |
| AtUGD4 | 0.25 |
| cvUGD-HI | 0.06 |
| cvUGD0KA | 0.14 |

The results demonstrate that all enzyme solutions of AtUGD1, AtUGD2, AtUGD3, and AtUGD4 have UGD activity, indicating that, in *Arabidopsis thaliana*, the AtUGD2, AtUGD3, and AtUGD4 genes, as well as the already reported AtUGD1 gene, all encode UGD.

Example 2

Isolation of Chlorella-Virus-Derived UGD Gene

For isolation of the chlorella-virus-derived UDP-glucose dehydrogenase (cvUGD) gene by PCR, the primers of SEQ ID NOS: 31 and 32 were designed based on the known sequence information of chlorella virus strain PBCV-1. For introduction into the expression vector pMAL-c2, EcoRI and PstI sites were added to the 5'-end and 3'-end primers, respectively. PCR was carried out using a KOD-plus-DNA polymerase and a reaction program of 1 cycle of 94° C. for 2 minutes and 30 cycles of 94° C. for 15 seconds, 60° C. for 30 seconds, and 68° C. for 1 minute. The genomic DNA of chlorella virus strain Hirosaki (CVHI1) and strain Kakunodate (CVKA1) was used as template DNA. An agarose gel electrophoresis analysis showed PCR-amplified bands with predicted size. Each PCR-amplified fragment was cleaved with EcoRI and PstI, and cloned into pMAL-c2 digested with the same restriction enzymes, using Ligation High. Using the ligation mixture, *Escherichia coli* strain JM109 was transformed according to the above-mentioned known method, and the transformants were applied to LB agar medium containing 50 μg/mL ampicillin, and cultured overnight at 37° C. The plasmid was extracted from the grown colonies of the transformants using a known method.

The nucleotide sequences of the inserted fragments were determined using a DNA sequencer, and novel UGD genes derived from strains CVHI1 and CVKA1 were obtained and named "cvUGD-HI gene" and "cvUGD-KA gene". The nucleotide sequences of the cvGFAT-HI and cvUGD-KA genes are shown in SEQ ID NOS: 11 and 13. Thus, the plasmids pMAL-c2/cvUGD-HI and pMAL-c2/cvUGD-KA were constructed.

Figure 2:
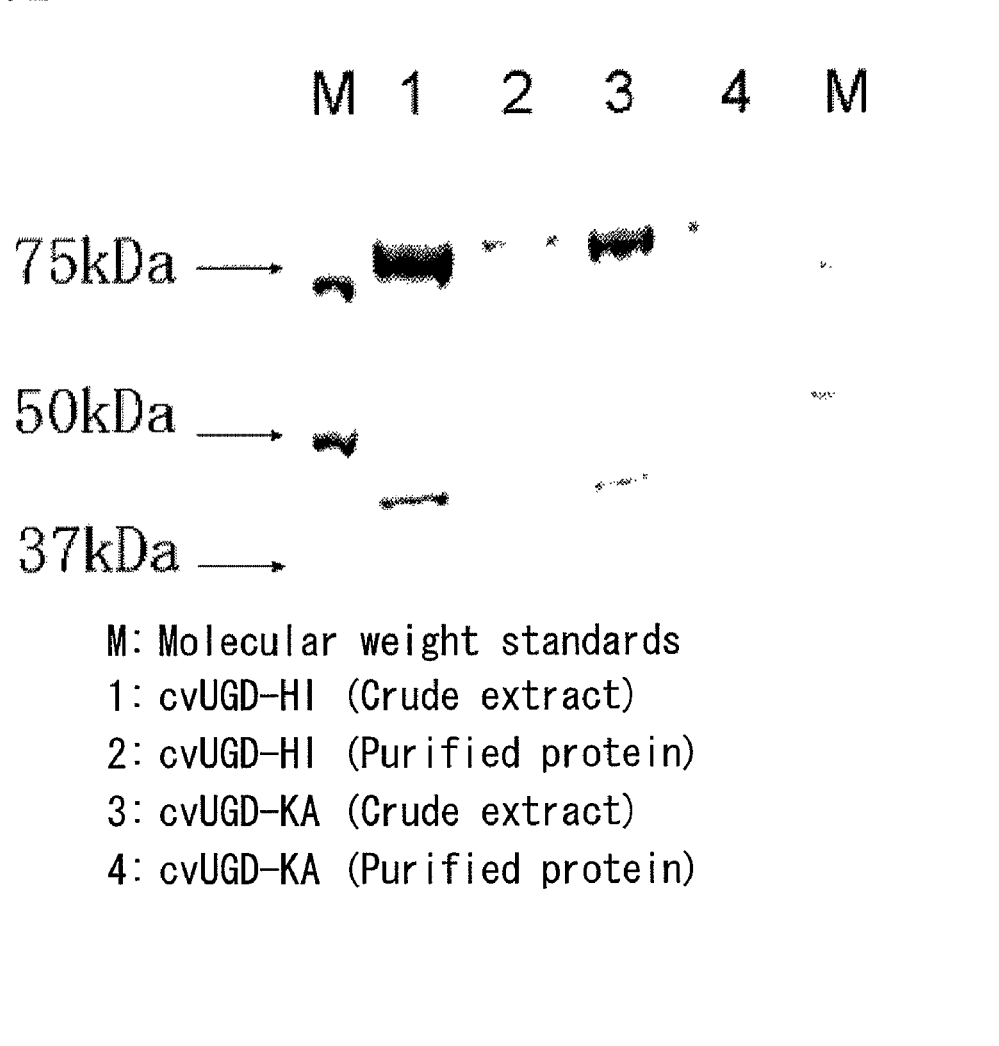
FIG. 2 shows SDS-PAGE analysis of cvUGD before and after purification.

MBP fusion proteins were expressed and purified in the same manner as in Example 1. FIG. 2 shows the SDS-PAGE analysis of the obtained MBP fusion proteins. A band of the predicted size was observed in all enzyme solutions of the clones.

The UGD activities of the expressed MBP fusion proteins were measured in the same manner as in Example 1. Table 1 shows the enzymatic activity of the MBP fusion proteins.

The UGD activity measurement by the above method demonstrated that both cvUGD-HI and cvUGD-KA encode functional enzymes.

Example 3

Isolation of *Arabidopsis-thaliana*-Derived GFAT Gene

As a plant-derived GFAT gene, a corns-derived GFAT gene (Accession No. AY106905) has been reported to be isolated (WO 00/11192), but no GFAT genes have been isolated from other species of plants. The NCBI BLAST (www.ncbi.nlm.nih.gov/BLAST/) database shows an *Arabidopsis-thaliana*-derived GFAT gene (Accession No. NM_113314), which is highly homologous to the known gene. The nucleotide sequence of the *Arabidopsis-thaliana*-derived GFAT gene is shown in SEQ ID NO: 9 in the Sequence Listing.

RNA was extracted from *Arabidopsis thaliana* according to the RNeasy (QIAGEN) protocol. For a reverse transcription reaction, 2 μg of total RNA was dissolved in 5.5 μL of sterile water, mixed with 1 μL of 10 μM oligo d(T) primer, and thermally denatured at 70° C. for 10 minutes. After rapid cooling, the reverse transcription reaction was performed using a ReverTraAce kit (Toyobo), at 42° C. for 30 minutes and at 99° C. for 5 minutes.

For PCR amplification of the *Arabidopsis-thaliana*-derived GFAT gene, the primers of SEQ ID NOS: 33 and 34 were designed based on nucleotide sequences on the database. For introduction into a cell-free expression vector PEU-NII (Toyobo), a SalI site was added to the 3'-end primer. PCR was performed using a KOD-plus-DNA polymerase and a reaction program of 1 cycle of 94° C. for 2 minutes, 3 cycles of 94° C. for 15 seconds, 45° C. for 30 seconds, and 68° C. for 1 minute, and 30 cycles of 94° C. for 15 seconds, 55° C. for 30 seconds, and 68° C. for 1 minute. One microliter of reverse transcription reaction product was used as template DNA. An agarose gel electrophoresis analysis showed PCR-amplified bands with predicted size. The PCR-amplified fragment was cleaved with a restriction enzyme SalI, and cloned into pEU-NII digested with restriction enzymes EcoRV and SalI, using Ligation High. Using the ligation mixture, *Escherichia coli* strain JM109 was transformed according to the above-mentioned known method, and the transformants were applied to LB agar medium containing 50 μg/mL ampicillin, and cultured overnight at 37° C. The plasmid was extracted from the grown colonies of the transformants using a known method. Thus, the plasmid pEU-NII/AtGFAT was constructed.

The nucleotide sequence of the inserted fragment was determined using a DNA sequencer, and it was confirmed that the amplified fragment was the gene represented by SEQ ID NO: 9. The above reveals that the GFAT gene is expressed in *Arabidopsis thaliana*.

Figure 3:
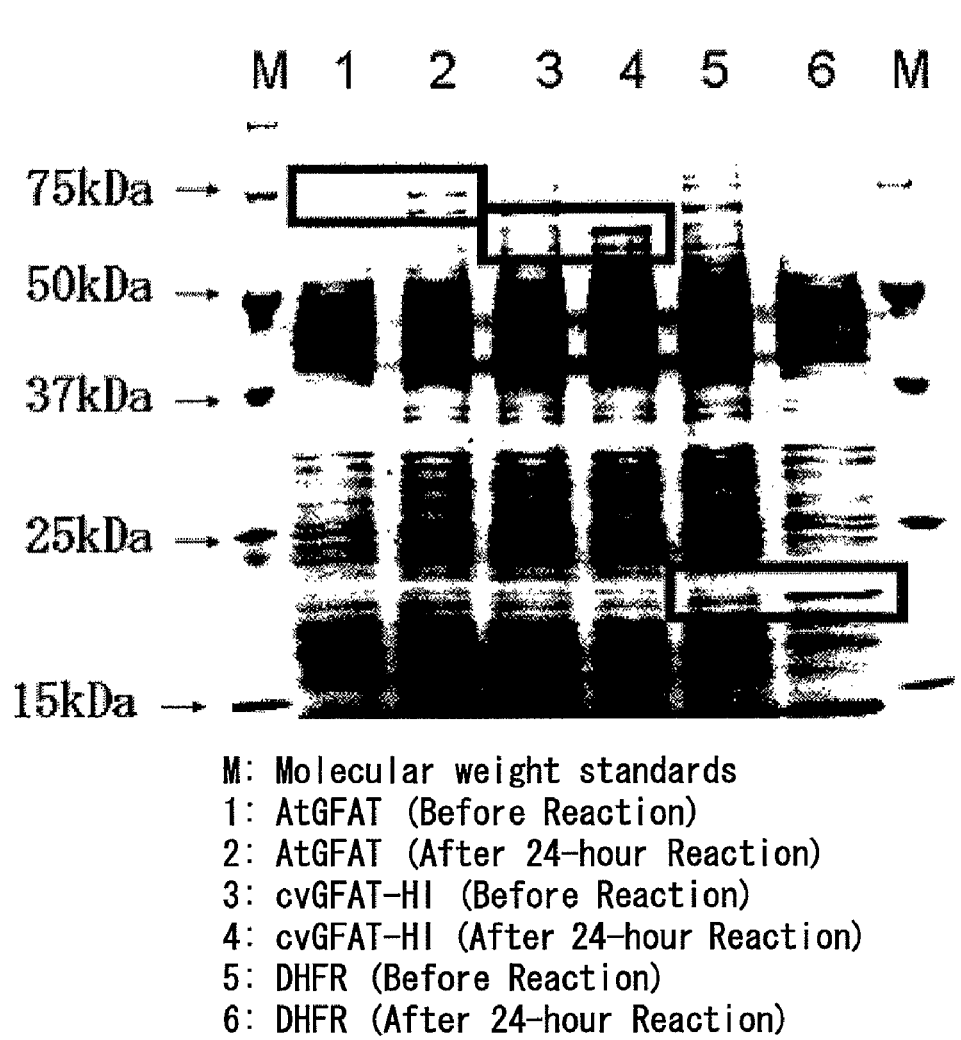
FIG. 3 shows GFAT expressed using PROTEIOS (registered trademark).

Using PROTEIOS (a registered tradmark of Toyobo), the reconmbinant protein of the AtGFAT was expressed. Specifically, a reaction was carried out at 37° C. for 4 hours using 5 μg of the plasmid pEU/AtGFAT as a template and a T7 RNA Polymerase, to synthesize mRNA. Thereafter, 6 μg of mRNA was mixed with wheat germ extract, and a reaction was carried out at 26° C. for 24 hours by the bilayer method. The reaction mixture was suspended in sample buffer (50 mM Tris-HCl (pH6.8), 2% SDS, 10% glycerol, 0.6% β-mercaptoethanol) and boiled for 5 minutes, and then the expressed protein was analyzed by SDS-PAGE. A band of the predicted size (about 75 kDa) was observed, indicating the expression of the AtGFAT protein (FIG. 3).

Figure 4:
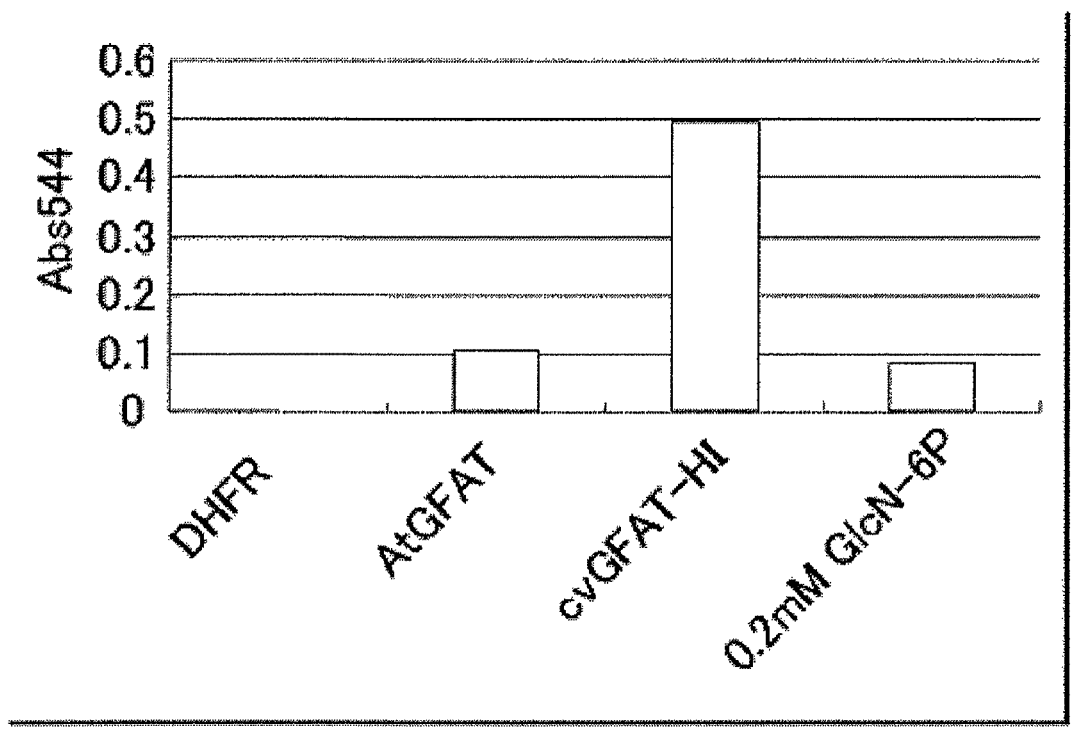
FIG. 4 shows measurement of GFAT activity using the Reissig method.

The protein expression solution was subjected to GFAT reaction. Specifically, 50 μL of the protein expression solution was added to a solution (pH 7.0) containing fructose-6-phosphate (15 mM), L-glutamine (15 mM), EDTA (1 mM), DTT (1 mM), and $KH_2PO_4$ (60 mM), and reacted at 37° C. for 4 hours. Glucosamine-6-phosphate in the reaction mixture was measured using the Reissig method (J. Biol. Chem, 1955, 217 (2), 959-66), which is an improvement of the Morgan & Elson method, to evaluate GFAT activity. FIG. 4 shows the results. Glucosamine-6-phosphate was not detected in pEU-NII/DHFR used as a control, whereas an increase of glucosamine-6-phosphate was observed in pEU-NII/AtGFAT, demonstrating that an active GFAT enzyme was present in the protein expression solution.

The above reveals that the AtGFAT gene encodes a functional enzyme in *Arabidopsis thaliana*.

Example 4

Isolation of Chlorella-Virus-Derived GFAT Gene

PCR primers were prepared to isolate the chlorella-virus-derived glutamine-fructose-6-phosphate amidotransferase gene (cvGFAT) by PCR. Based on already reported nucleotide sequence information of the chlorella virus strain PBCV-1, the primers of SEQ ID NOS: 35 and 36 were designed so as to amplify from 100 bp outside the putative GFAT region PCR was performed using a KOD-plus-DNA polymerase and a reaction program of 1 cycle of 94° C. for 2 minutes and 30 cycles of 94° C. for 15 seconds, 60° C. for 30 seconds, and 68° C. for 1 minute. The genomic DNA of chlorella virus strains Hirosaki (CVHI1) and Kakunodate (CVKA1) was used as template DNA. The PCR-amplified fragments were cloned into a pPCR-Script Amp SK(+) cloning vector (Stratagene). The nucleotide sequences of the inserted fragments were determined using a DNA sequencer, and novel GFAT genes derived from strains cvHI1 and cvKA1 were identified and named "cvGFAT-HI gene" and "cvGFAT-KA gene". The nucleotide sequences of cvGFAT-HI and cvGFAT-KA genes are shown in SEQ ID NOS: 5 and 7.

The open reading frame regions of the cvGFAT-HI and cvGFAT-KA genes represented by SEQ ID NOS: 5 and 7 were cloned into vectors for cell-free protein synthesis to express proteins.

PCR was performed under the above-mentioned conditions using pPCR-Script Amp SK(+) cloning vector containing the cvGFAT-HI gene as a template and the primers represented by SEQ ID NOS: 37 and 38. PCR was performed under the above-mentioned conditions using pPCR-Script Amp SK(+) cloning vector containing the cvGFAT-KA gene as a template and the primers represented by SEQ ID NOS: 37 and 39. For the PCR, a KOD-plus-DNA polymerase, and a reaction cycle of 1 cycle of 94° C. for 2 minutes and 30 cycles of 94° C. for 15 seconds, 60° C. for 30 seconds, and 68° C. for 1 minute, were used. Each PCR-amplified fragment was cleaved with XbaI and cloned into the EcoRV and XbaI sites of the PEU-NII vector. Using the ligation mixture, *Escherichia coli* strain DH5α was transformed according to the above-mentioned known method, and the transformants were applied to LB agar medium containing 50 µg/mL ampicillin, and cultured overnight at 37° C. The plasmid was extracted from the grown colonies of the transformants using a known method. Thus, the plasmids pEU-NII/cvGFAT-HI and pEU-NII/cvGFAT-KA were constructed.

Using pEU-NII/cvGFAT-HI and pEU-NII/cvGFAT-KA and PROTEIOS (registered trademark), proteins were expressed in the same manner as in Example 3. SDS-PAGE analysis of the expressed proteins confirmed bands of the predicted sizes (about 65 kDa), indicating the expression of cvGFAT proteins (FIG. 3).

The protein expression solution was subjected to GFAT reaction in the same manner as in Example 3. FIG. 4 shows the results. Glucosamine-6-phosphate was not detected in pEU/DHFR used as a control, whereas an increase of glucosamine-6-phosphate was observed in pEU/cvGFAT-HI, confirming that an active GFAT enzyme was present in the protein expression solution.

Example 5

Cloning of Chlorella-Virus-Derived HAS Gene into pBI121

For the cloning of a chlorella-virus-derived hyaluronic acid synthetase gene (cvHAS, SEQ ID NO: 1) into the plant transformation vector (hereinafter also referred to as "expression vector") pBI121 (Jefferson et al., 1987, EMBO J, 6, 3901-3907), the primers represented by SEQ ID NOS: 40 and 41 were prepared. PCR was performed using cvHAS-containing plasmid DNA as a template, a KOD-plus-DNA polymerase, and a reaction program of 1 cycle of 94° C. for 2 minutes, 3 cycles of 94° C. for 15 seconds, 45° C. for 30 seconds, and 68° C. for 1 minute, and 30 cycles of 94° C. for 15 seconds, 55° C. for 30 seconds, and 68° C. for 1 minute. PCR-amplified fragment was purified and cleaved with BamHI and DraI. Subsequently, cvHAS was inserted into the expression vector pBI121 as follows: pBI121 was digested with the restriction enzyme SacI, blunted with Blunting High (Toyobo), and digested with BamHI; and then the cvHAS gene digested with a restriction enzyme was cloned. Using the ligation mixture, *Escherichia coli* strain DH5α was transformed according to the above-mentioned known method, and the transformants were applied to LB agar medium containing 50 µg/mL ampicillin, and cultured overnight at 37° C. The plasmid was extracted from the grown colonies of the transfor-mants using a known method. Thus, pBI121/cvHAS (hereinafter sometimes referred to as pBIHA) containing cvHAS was prepared.

Example 6

Cloning of Chlorella-Virus-Derived GFAT Gene into pBI121

PCR was performed using the primers represented by SEQ ID NOS: 42 and 38 and cvGFAT-HI-containing plasmid DNA as a template. For the PCR, KOD-plus- and a reaction program of 1 cycle of 94° C. for 2 minutes, 2 cycles of 94° C. for 15 seconds, 50° C. for 30 seconds, and 68° C. for 1 minute, and 28 cycles of 94° C. for 15 seconds, 60° C. for 30 seconds, and 68° C. for 1 minute, were used. The PCR-amplified fragment was digested with BamHI. Subsequently, cvGFAT-HI was inserted into the expression vector ppBI121 as follows: pBI121 was digested with SacI, blunted with Blunting High, and digested with BamHI, and then the cvGFAT-HI gene digested with the above restriction enzymes was cloned. Using the ligation mixture, *Escherichia coli* strain DH5α was transformed according to the above-mentioned known method, and the transformants were applied to LB agar medium containing 50 µg/mL ampicillin and cultured overnight at 37° C. The plasmid was extracted from the grown colonies of the transformants using a known method. Thus, pBI121/cvGFAT-HI (hereinafter sometimes referred to as pBIGF) containing cvGFAT-HI was prepared.

Example 7

Subcloning of Chlorella-Virus-Derived GFAT Gene and HAS Gene into pBluescript pBIHA was digested with the restriction enzymes PvuII and PstI, in that order, and subcloned into the PstI and SmaI sites of pBluescript to obtain pBluescript/35S-cvHAS-NOS (hereinafter sometimes referred to as pBSHA).

pBIGF was digested with the restriction enzymes PvuII and SphI, in that order. After blunting with Blunting High (Toyobo), pBIGF was subcloned into the EcoRV site of pBluescript to obtain pBluescript/35S-cvGFAT-NOS (hereinafter sometimes referred to as pBSGF).

pBSGF was digested with the restriction enzymes KpnI and NotI, in that order. After blunting with Blunting High (Toyobo), 35S-cvGFAT-NOS was subcloned into pBSHA previously digested with SpeI, blunting, and dephosphorylation, in that order, to obtain pBluescript/cvHAS-cvGFAT (hereinafter sometimes referred to as pBSHG).

Example 8

Cloning of Chlorella-Virus-Derived GFAT Gene and HAS Gene into pBI121 pBSHG was digested with the restriction enzymes KpnI and NotI in that order, and the expression cassette of cvHAS-cvGFAT was cleaved and blunted. Then, cvHAS-cvGFAT was inserted into the expression vector pBI121 as follows: pBI121 was digested with the restriction enzymes SacI and HindIII, and blunted with Blunting High, and then the cvHAS-cvGFAT gene digested with the above restriction enzymes was cloned. Using the ligation mixture, *Escherichia coli* strain DH5α was transformed according to the above-mentioned known method, and the transformants were applied to LB agar medium containing 50 µg/mL ampicillin, and cultured overnight at 37° C. The plasmid was extracted from the grown colonies of the transformants using a known method. Thus, pBI121/cvHAS-cvGFAT (hereinafter sometimes referred to as pBIHG) containing cvHAS-cvGFAT was prepared.

Example 9

Preparation of Electrocompetent Cells

Five milliliters of LB medium was inoculated with a single colony of Agrobacterium LBA4404 (Agrobacterium tumefaciens strain LBA4404), and subjected to shaking culture overnight at 28° C. The culture medium was inoculated into 500 mL of LB medium and subjected to shaking culture at 28° C. until the turbidity at 600 nm became 0.5. The culture medium was harvested by centrifugation (5000 rpm, 10 min, 4° C.); the supernatant was removed; 500 mL of sterile water was added to suspend and wash the cells; centrifugation (5000 rpm, 10 min, 4° C.) was carried out again to harvest the cells; and the supernatant was removed. After performing the above procedure twice, the precipitates were suspended in 20 mL of cooled 10% glycerol solution, the cells were harvested by centrifugation (5000 rpm, 10 min, 4° C.), and the supernatant was removed. The precipitates were suspended in 3 mL of cooled 10% glycerol solution, and 40-μL aliquots of the suspension were placed in 1.5 mL centrifuge tubes, frozen with liquid nitrogen, and stored at −80° C.

Example 10

Introduction of pBIHG into Agrobacterium Strain LBA4404

A suspension obtained by mixing 1 μL of the expression plasmid pBIHG (200 μg/ml) with 40 μL of electrocompetent cells of A. tumefaciens LBA4404 (Invitrogen) was poured into a cuvette (distance between the electrodes: 1 mm) previously cooled on ice, and a pulsed electric field (1.8 kV, 25 μF, 200Ω) was applied. Immediately thereafter, 500 μL of SOC was added, and the resulting mixture was incubated at 28° C. for 3 hours. The incubated cells were then applied to LB plate medium containing kanamycin, and cultured at 25° C. for 3 days to obtain Agrobacterium cells carrying pBIHG.

Example 11

Infection of Tobacco with Agrobacterium tumefacince Strain LBA4404 Containing pBIHG Tobacco (Nicotiana tabacum SR-1) was transformed according to the leaf disc method using Agrobacterium ("Plant Biotechnology II" edited by Yasuyuki Yamada and Yoshimi Okada, Tokyo Kagaku Dojin, 1991). Tobacco leaf discs were immersed for 3 minutes in an Agrobacterium culture medium carrying pBIHG or pBIHA previously cultured overnight at 28° C. in 5 mL of LB medium containing 50 mg/L kanamycin. Excess cells were then removed on filter paper. The leaf discs were placed in a differentiation medium prepared by adding 3% sucrose, B5 vitamin, 1 mg/L benzylaminopurine, 1 mg/L naphthalene acetic acid, and 0.3% gellan gum to MS (Murashige and Skoog) inorganic salt (Murashige and Skoog, 1962, Physiol. Plant., 15, 473) and adjusting the pH to 5.7, and were left to stand in the dark at 28° C. for 2 days. The infected leaf discs were washed three times with sterile water, and excess moisture was removed on filter paper. The leaf discs were then left to stand in the differentiation medium containing kanamycin (100 mg/L) and cefotaxime (250 mg/L) as antibiotics, and callus formation was induced at 25° C. under 16-hour light conditions. Three weeks after starting the induction, morphologically normal shoots were selected, cut out in a form containing stems and leaves, and transferred into a rooting medium (MS inorganic salt, 3% sucrose, B5 vitamin and 0.3% gellan gum, pH 5.7) containing kanamycin (100 mg/L) and cefotaxime (250 mg/L) to induce rooting at 25° C. under 16-hour light conditions. After two weeks, rooted shoots were transferred to a fresh rooting culture medium to obtain lines with growing stems and leaves.

Example 12

Quantitation of Hyaluronic Acid Produced by Transformed Tobacco

Figure 5:
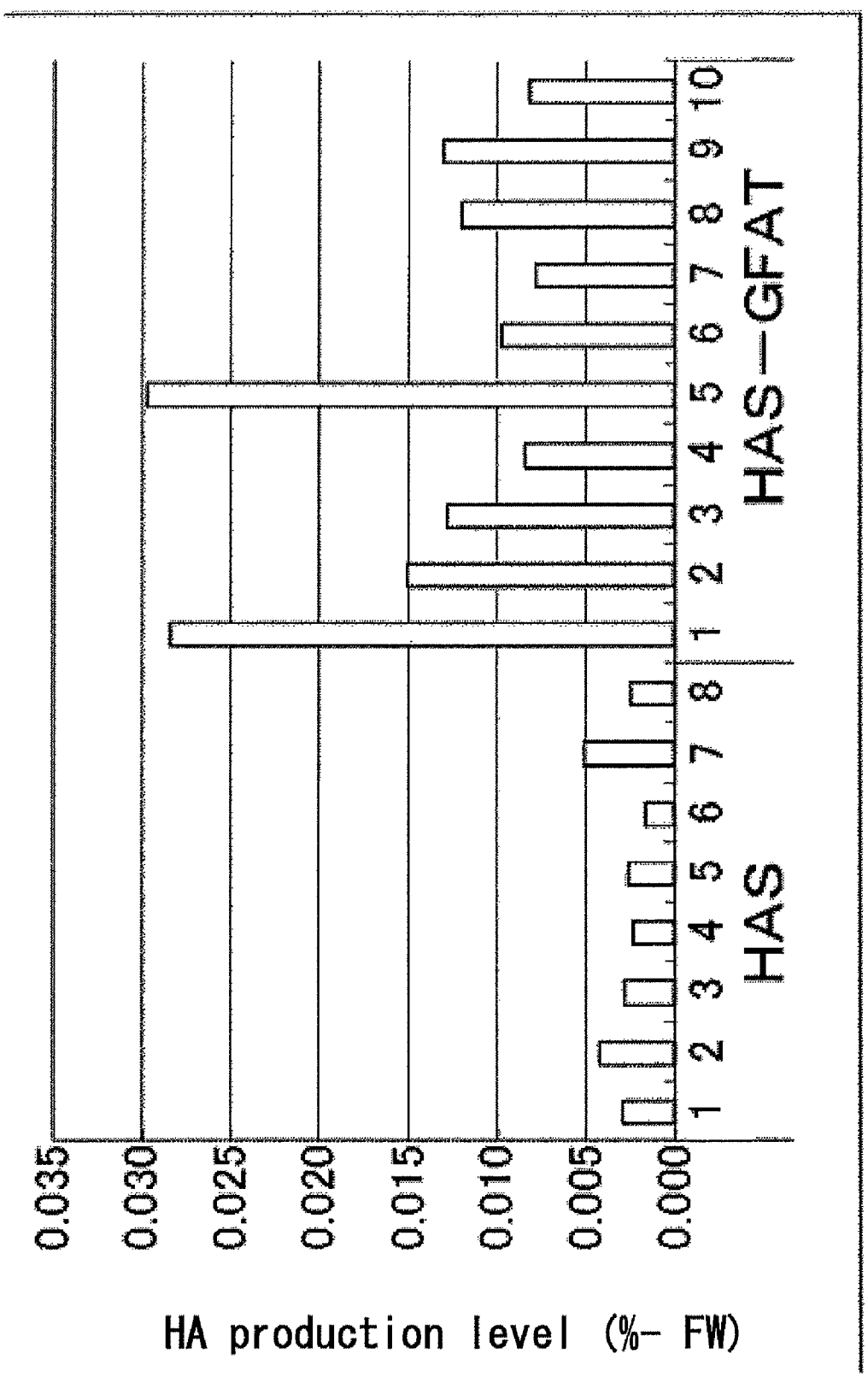
FIG. 5 shows the hyaluronic acid production level of transgenic tobacco plants in which cvHAS-cvGFAT gene and cvHAS gene are introduced respectively.

About 100 mg of transformed tobacco leaves obtained by the infection with Agrobacterium described above was transferred to a 2 mL tube, and suspended in 200 μL of buffer (containing 20 mM Tris-HCl at pH 7.5, 0.2M NaCl, 1 mM EDTA, and 10 mM 2-ME), and 400 mg of stainless steel beads (diameter: 4.8 mm) were added. The tobacco leaves were pulverized by shaking and agitating the tube using Bead Smash (Wakenyaku, BS-12) (4,000 rpm, 2 minutes). The liquid after pulverization was centrifuged (15,000 rpm, 10 minutes), and the supernatant was recovered as a crude extract. The crude extract was diluted with water and used as a measurement sample. The quantitation of hyaluronic acid was performed using a hyaluronic acid plate "Chugai" (Fujirebio, Inc.). FIG. 5 shows the results. The transformed tobacco into which the cvHAS-cvGFAT gene had been introduced had significantly improved hyaluronic acid productivity compared to the transformed tobacco into which the cvHAS gene had been introduced.

Example 13

Cloning of Chlorella-Virus-Derived UGD Gene into pBI121

PCR was performed using the primers represented by SEQ ID NO: 43 and SEQ ID NO: 44 and plasmid DNA containing cvUGD-HI as a template. For the PCR, KOD-plus-, and a reaction program of 1 cycle of 94° C. for 2 minutes, 2 cycles of 94° C. for 15 seconds, 50° C. for 30 seconds, and 68° C. for 1 minute), and 28 cycles of 94° C. for 15 seconds, 60° C. for 30 seconds, and 68° C. for 1 minute, were used. PCR-amplified fragment was digested with BamHI and SacI. Subsequently, cvUGD-HI was inserted into the expression vector pBI121 as follows: pBI121 was digested with SacI and then with BamHI, and the cvUGD-HI gene digested with the above-mentioned restriction enzymes was cloned into pBI121. Using the ligation mixture, Escherichia coli strain DH5α was transformed according to the above-mentioned known method, and the transformant was applied to LB agar medium containing 50 μg/ml ampicillin, and cultured overnight at 37° C. The plasmid was extracted from the grown colonies of the transformants using a known method. Thus, pBIUG containing cvUGD-HI was prepared.

Example 14

Subcloning of Chlorella-Virus-Derived UGD Gene into pBluescript pBIUG was digested with restriction enzymes EcoRI and HindIII, subcloned into the EcoRI and HindIII sites of pBluescript to prepare pBSUG.

pBSUG was digested with SpeI and blunted with Blunting High to destroy the SpeI site. Subsequently, pBSHA was digested with NotI, blunted, and digested with KpnI to cut out 35S-cvHAS-NOS. pBSUG was digested with XhoI, blunted, and digested with KpnI; and 35S-cvHAS-NOS, which had been cut out, was ligated to produce pBSHU. pBSGF was digested with SalI, blunted, and digested with NotI to cut out 35S-cvGFAT-NOS. pBHU was digested with SpeI, blunted, and digested with NotI, and 35S-cvGFAT-NOS, which had been cut out, was legated to produce pBSHUG.

Example 15

Cloning of Chlorella-Virus-Derived UGD Gene, GFAT Gene, and HAS Gene, into pBI121

Using synthetic DNA, modified pBI121 was produced in which a SmaI site had been added downstream of the HindIII site of pBI121, and a KpnI site had been added upstream of the EcoRI site. pBSHUG was digested with NotI, blunted, and digested with KpnI; the linked expression cassettes of HAS, UGD and GFAT were cut out and cloned into the modified pBI121 cleaved with SmaI and KpnI. Using the ligation mixture, *Escherichia coli* strain DH5α was transformed according to the above-mentioned known method, and the transformants were applied to LB agar medium containing 50 µg/ml ampicillin, and cultured overnight at 37° C. The plasmid was extracted from the grown colonies of the transformants using a known method. Thus, pBIHUG containing expression cassettes of HAS, UGD and GFAT were prepared.

Example 16

Figure 6:
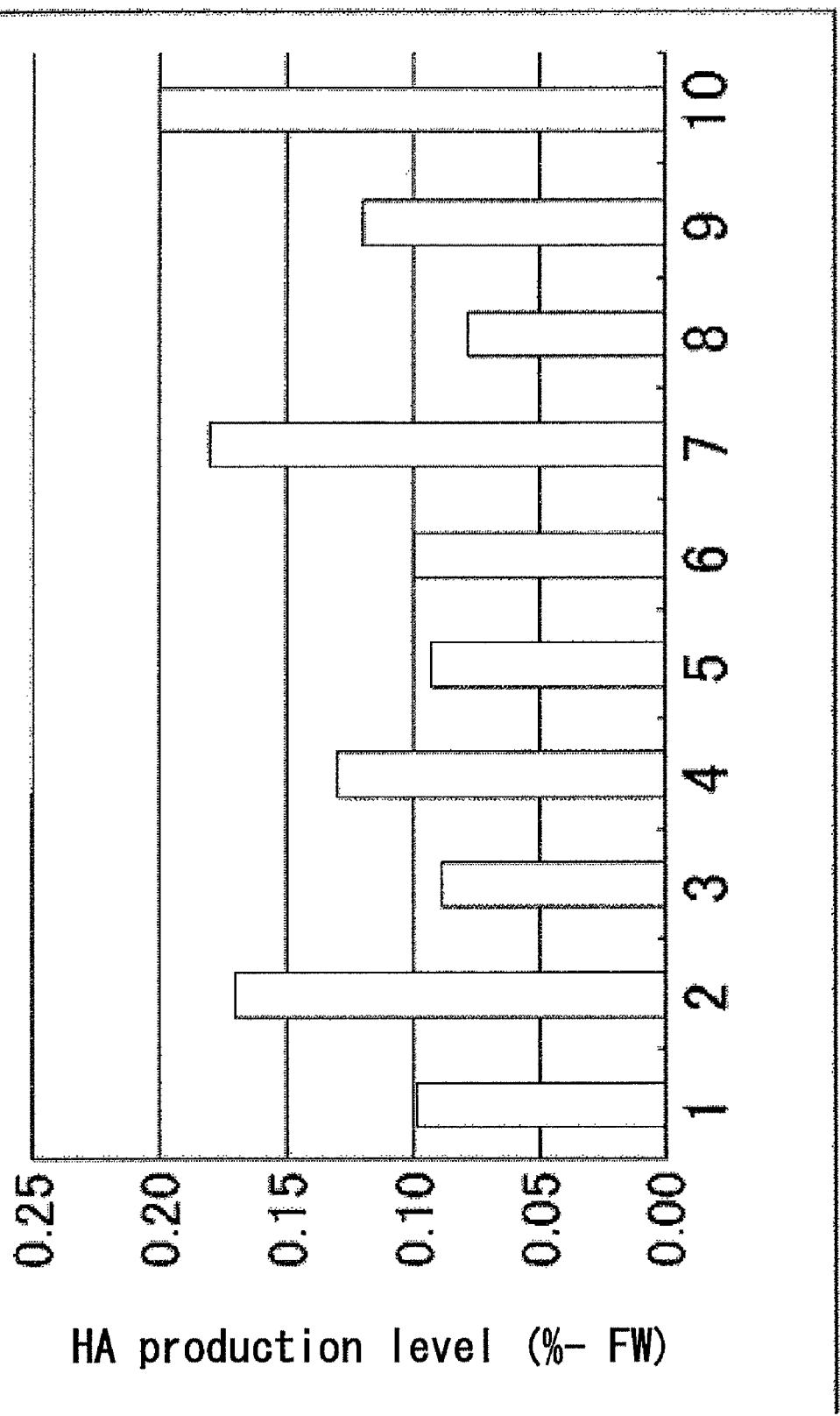
FIG. 6 shows the hyaluronic acid production level of transgenic tobacco plants into which multiple genes have been introduced.

Preparation of Transformed Tobacco into which pBIHUG had been Introduced, and Quantitative Analysis of Hyaluronic Acid Using the expression plasmid pBIHUG and following the procedures shown in Examples 10 and 11, pBIHUG was introduced into *Agrobacterium* strain LBA4404, and tobacco leaf discs were infected with *Agrobacterium* strain LBA4404 containing pBIHUG. As a result, 20 lines of tobacco were obtained in which introduction of HAS, UGD, and GFAT genes had been confirmed. Following the procedure shown in Example 12, crude extracts were prepared and hyaluronic acid was quantitated. FIG. 6 shows the results. The transformed tobacco into which the HAS, UGD and GFAT genes had been introduced showed significantly improved hyaluronic acid productivity compared to the transformed tobacco into which the cvHAS gene had been introduced and the transformed tobacco into which the cvHAS-cvGFAT gene had been introduced.

Example 17

Quantitative Analysis of Hyaluronic Acid Produced by Transformed Tobacco (T1 Generation)

Seeds were collected from the transformed tobacco of Example 12, into which the cvHAS-cvGFAT gene had been introduced, and inoculated into MS differentiation medium containing kanamycin (100 mg/L). A crude extract was obtained from the grown transformed tobacco (T1 generation) in the same manner as in Example 12, and hyaluronic acid was quantitated, demonstrating the production level of hyaluronic acid equivalent to that of T0 generation.

INDUSTRIAL APPLICABILITY

According to the present invention, a hyaluronic acid synthetase gene is expressed in a plant, and in particular, hyaluronic acid is produced in a high yield in a plant. The present invention provides a plant or cultured plant cells that are capable of producing hyaluronic acid in a higher yield than the prior art; a method for producing the plant or cultured plant cells; and an expression vector. Since safe hyaluronic acid produced in a plant can be provided at a low cost, the present invention is expected to greatly contribute to the industry.

The invention claimed is:

1. A method of producing hyaluronic acid, comprising co-expressing a protein with hyaluronic acid synthase activity, an exogenous protein with glutamine:fructose-6-phosphate amidotransferase activity, and an exogenous protein with uridin-5'-diphospho(UDP)-glucose dehydrogenase activity in a plant cell or a plant.

2. A method of producing hyaluronic acid, containing the steps of:
   (1) transforming a plant cell or a plant using a recombinant expression vector, the recombinant expression vector having DNA encoding a protein with hyaluronic acid synthase activity, DNA encoding a protein with glutamine:fructose-6-phosphate amidotransferase activity, and DNA encoding a protein with uridin-5'-diphospho(UDP)-glucose dehydrogenase activity, each said DNA being under control of a plant promoter;
   (2) growing a transformant obtained by the transformation; and
   (3) isolating hyaluronic acid produced by the transformant.

3. The method of producing hyaluronic acid according to claim 2, wherein the promoter is an organ-specific or a tissue-specific promoter.

4. The method of producing hyaluronic acid according to claim 2, wherein the DNA encoding a protein with hyaluronic acid synthase activity is DNA of (a) or (b) below:
   (a) DNA having a nucleotide sequence represented by SEQ ID NO: 1 or 3; or
   (b) DNA complementarily hybridizing to the nucleotide sequence of (a) under highly stringent conditions in which washing is performed in salt concentrations equivalent to that of 0.1×SSC or 0.1% SDS at 60° C.

5. The method of producing hyaluronic acid according to claim 1, wherein the protein with hyaluronic acid synthase activity is a protein of (a) or (b):
   (a) a protein having an amino acid sequence shown by SEQ ID NO: 2 or 4; or
   (b) a protein having the amino acid sequence of (a) with one to ten amino acids deleted, substituted or added.

6. The method of producing hyaluronic acid according to claim 2, wherein DNA encoding a protein with glutamine:fructose-6-phosphate amidotransferase activity and DNA encoding a protein with UDP-glucose dehydrogenase activity are DNA derived from chlorella virus or *Arabidopsis*.

7. The method of producing hyaluronic acid according to claim 2, wherein DNA encoding a protein with glutamine:fructose-6-phosphate amidotransferase activity is DNA of (a) or (b) below:
   (a) DNA having a nucleotide sequence shown by SEQ ID NO: 5, 7 or 9; or
   (b) DNA complementarily hybridizing to the nucleotide sequence of (a) under highly stringent conditions in which washing is performed in salt concentrations equivalent to that of 0.1×SSC or 0.1% SDS at 60° C.

8. The method of producing hyaluronic acid according to claim 1, wherein the protein with glutamine:fructose-6-phosphate amidotransferase activity is a protein of (a) or (b) below:
   (a) a protein having an amino acid sequence shown by SEQ ID NO: 6, 8 or 10; or
   (b) a protein having the amino acid sequence of (a) with one to ten amino acids deleted, substituted or added.

9. The method of producing hyaluronic acid according to claim 2, wherein DNA encoding a protein with UDP-glucose dehydrogenase activity is DNA of (a) or (b) below:
   (a) DNA having a nucleotide sequence shown by SEQ ID NO: 11, 13, 17, 19, or 21; or
   (b) DNA complementarily hybridizing to the nucleotide sequence of (a) under highly stringent conditions in which washing is performed in salt concentrations equivalent to that of 0.1×SSC or 0.1% SDS at 60° C.

10. The method of producing hyaluronic acid according to claim 1, wherein the protein with UDP-glucose dehydrogenase activity is a protein of (a) or (b) below:
    (a) a protein having an amino acid sequence shown by SEQ ID NO: 12, 14, 16, 18, 20 or 22; or
    (b) a protein having the amino acid sequence of (a) with one to ten amino acids deleted, substituted or added.

11. The method of producing hyaluronic acid according to claim 1, wherein the plant is selected from the group consisting of angiosperms, gymnosperms, pteridophytes and bryophytes.

12. The method of producing hyaluronic acid according to claim 3, wherein one or more organs are selected from the group consisting of roots, stems, stem tubers, leave, floral organs, tuberous roots, seeds and shoot apices.

13. The method of producing hyaluronic acid according to claim 3, wherein one or more tissues are selected from the group consisting of epidermis, phloem, soft tissues, xylem and vascular bundles.

14. A transgenic plant cell or a transgenic plant or a progeny, organ or tissue thereof having an ability to produce hyaluronic acid by co-expressing a protein with hyaluronic acid synthase activity, an exogenous protein with glutamine:fructose-6-phosphate amidotransferase activity, and an exogenous protein with uridin-5'-diphospho(UDP)-glucose dehydrogenase activity.

15. A transgenic plant cell or a transgenic plant transformed with a recombinant expression or a progeny, organ or tissue thereof vector containing DNA encoding a protein with hyaluronic acid synthase activity, DNA encoding a protein with glutamine:fructose-6-phosphate amidotransferase activity, and DNA encoding a protein with uridin-5'-diphospho(UDP)-glucose dehydrogenase activity, each said DNA being under control of a plant promoter.

16. The transgenic plant cell or the transgenic plant, the progeny having the same nature thereof, or the organ or the tissue thereof according to claim 15, wherein the promoter is an organ-specific or a tissue-specific promoter.

17. The transgenic plant cell or the transgenic plant, the progeny thereof, or the organ or the tissue thereof according to claim 15, wherein the DNA encoding a protein with hyaluronic acid synthase activity is DNA of (a) or (b) below:
  (a) DNA having a nucleotide sequence shown in SEQ ID NO: 1 or 3; or
  (b) DNA complementarily hybridizing to the DNA having the nucleotide sequence of (a) under highly stringent conditions in which washing is performed in salt concentrations equivalent to that of 0.1×SSC or 0.1% SDS at 60° C.

18. The transgenic plant cell or the transgenic plant according to claim 14, wherein the protein with hyaluronic acid synthase activity is a protein of (a) or (b) below:
  (a) a protein having an amino acid sequence shown by SEQ ID NO: 2 or 4; or
  (b) a protein having the amino acid sequence of (a) with one to ten amino acids deleted, substituted or added.

19. The transgenic plant cell or the transgenic plant, the progeny thereof, or the organ or the tissue thereof according to claim 15, wherein the DNA encoding a protein with glutamine:fructose-6-phosphate amidotransferase activity and the DNA encoding a protein with UDP-glucose dehydrogenase activity are derived from chlorella virus, *Arabidopsis*, or chlorella virus and *Arabidopsis*.

20. The transgenic plant cell or the transgenic plant, the progeny thereof, or the organ or the tissue thereof according to claim 15, wherein the DNA encoding a protein with glutamine:fructose-6-phosphate amidotransferase activity is DNA of (a) or (b) below:
  (a) DNA having a nucleotide sequence shown by SEQ ID NO: 5, 7 or 9; or
  (b) DNA complementarily hybridizing to the nucleotide sequence of (a) under highly stringent conditions in which washing is performed in salt concentrations equivalent to that of 0.1×SSC or 0.1% SDS at 60° C.

21. The transgenic plant cell or the transgenic plant, the progeny thereof, or the organ or the tissue thereof according to claim 14, wherein the protein with glutamine:fructose-6-phosphate amidotransferase activity is a protein of (a) or (b) below:
  (a) a protein having an amino acid sequence shown by SEQ ID NO: 6, 8 or 10; or
  (b) a protein having the amino acid sequence of (a) with one to ten amino acids deleted, substituted or added.

22. The transgenic plant cell or the transgenic plant, the progeny thereof, or the organ or the tissue thereof according to claim 15, wherein DNA encoding a protein with UDP-glucose dehydrogenase activity is DNA of (a) or (b) below:
  (a) DNA having a nucleotide sequence shown by SEQ ID NO: 11, 13, 15, 17, 19, or 21; or
  (b) DNA complementarily hybridizing to the nucleotide sequence of (a) under highly stringent conditions in which washing is performed in salt concentrations equivalent to that of 0.1×SSC or 0.1% SDS at 60° C.

23. The transgenic plant cell or the transgenic plant, the progeny thereof, or the organ or the tissue thereof according to claim 14, wherein the protein with UDP-glucose dehydrogenase activity is a protein of (a) or (b) below:
  (a) a protein having an amino acid sequence shown by SEQ ID NO: 12, 14, 16, 18, 20 or 22; or
  (b) a protein having the amino acid sequence of (a) with one to ten amino acids deleted, substituted or added.

24. The transgenic plant cell or the transgenic plant, the progeny thereof, or the organ or the tissue thereof according to claim 14, wherein the plant is selected from the group consisting of gymnosperms, gymnosperms, pteridophytes and bryophytes.

25. The transgenic plant cell or the transgenic plant, the progeny thereof; or the organ or the tissue thereof according to claim 14, wherein the organ is one or more organs selected from the group consisting of roots, stems, stem tubers, leaves, floral organs, tuberous roots, seeds and shoot apices.

26. The transgenic plant cell or the transgenic plant, the progeny thereof, or the organ or the tissue thereof according to claim 14, wherein the tissue is one or more tissues selected from the group consisting of epidermis, phloem, soft tissues, xylem and vascular bundles.

27. Plant extract obtained from the transgenic plant cell or the transgenic plant, the progeny having the same nature thereof, or the organ or the tissue thereof according to claim 14, wherein the plant extract has the ability to produce hyaluronic acid by co-expressing a protein with hyaluronic acid synthase activity, an exogenous protein with glutamine:fructose-6-phosphate amidotransferase activity, and an exogenous protein with uridin-5'-diphosphate(UDP)-glucose dehydrogenase activity.

28. The plant extract according to claim 27, wherein the plant extract contains hyaluronic acid.

29. A recombinant expression vector comprising DNA encoding a protein with hyaluronic acid synthase activity, DNA encoding a protein with glutamine:fructose-6-phosphate amidotransferase activity, and DNA encoding a protein with uridin-5'-diphospho(UDP)-glucose dehydrogenase activity, each said DNA being under control of a plant promoter.

30. The recombinant expression vector according to claim 29, wherein the promoter is an organ-specific or a tissue-specific promoter.

31. The recombinant expression vector according to claim 29, wherein the DNA encoding a protein with hyaluronic acid synthase activity is DNA of (a) or (b) below:
  (a) DNA having a nucleotide sequence shown in SEQ ID NO: 1 or 3; or
  (b) DNA complementarily hybridizing the nucleotide sequence of (a) under highly stringent conditions in which washing is performed in salt concentrations equivalent to that of 0.1×SSC or 0.1% SDS at 60° C.

32. The recombinant expression vector according to claim 29, wherein the protein with hyaluronic acid synthase activity is a protein of (a) or (b) below:
(a) a protein having an amino acid sequence shown by SEQ ID NO: 2 or 4; or
(b) a protein having the amino acid sequence of (a) with one to ten amino acids deleted, substituted or added.

33. The recombinant expression vector according to claim 29, wherein the DNA encoding a protein with glutamine:fructose-6-phosphate amidotransferase activity and the DNA encoding a protein with UDP-glucose dehydrogenase activity are DNA derived from chlorella virus, *Arabidopsis*, or chlorella virus and *Arabidopsis*.

34. The recombinant expression vector according to claim 29, wherein the DNA encoding a protein with glutamine:fructose-6-phosphate amidotransferase activity is DNA of (a) or (b) below:
(a) DNA having a nucleotide sequence shown by SEQ ID NO: 5, 7 or 9; or
(b) DNA complementarily hybridizing to the nucleotide sequence of (a) under highly stringent conditions in which washing is performed in salt concentrations equivalent to that of 0.1×SSC or 0.1% SDS at 60° C.

35. The recombinant expression vector according to claim 29, wherein the protein with glutamine:fructose-6-phosphate amidotransferase activity is a protein of (a) or (b) below:
(a) a protein having an amino acid sequence shown by SEQ ID NO: 6, 8 or 10; or
(b) a protein having the amino acid sequence of (a) with one to ten amino acids deleted, substituted or added.

36. The recombinant expression vector according to claim 29, wherein the DNA encoding a protein with UDP-glucose dehydrogenase activity is DNA of (a) or (b) below:
(a) DNA having a nucleotide sequence shown by SEQ ID NO: 11, 13, 15, 17, 19, or 21; or
(b) DNA complementarily hybridizing to the nucleotide sequence of (a) under highly stringent conditions in which washing is performed in salt concentrations equivalent to that of 0.1×SSC or 0.1% SDS at 60° C.

37. The recombinant expression vector according to claim 29, wherein the protein UDP-glucose dehydrogenase activity is a protein of (a) or (b) below:
(a) a protein having an amino acid sequence shown by SEQ ID NO: 12, 14, 16, 18, 20 or 22; or
(b) a protein having the amino acid sequence of (a) with one to ten amino acids deleted, substituted or added.

38. A method of generating a transgenic plant cell or the transgenic plant comprising transforming a plant cell or a plant using a vector according to claim 29, wherein the transgenic plant cell or the transgenic plant produces hyaluronic acid.

* * * * *

SEQUENCE LISTING

```
<160> NUMBER OF SEQ ID NOS: 44

<210> SEQ ID NO 1
<211> LENGTH: 1707
<212> TYPE: DNA
<213> ORGANISM: Chlorella virus

<400> SEQUENCE: 1
atgggtaaaa atataatcat aatggtttcg tggtacacca tcataacttc aaatctaatc        60
gcggttggag gagcctctct aatcttggct ccagcaatta ctgggtatat tctacattgg       120
aatattgctc tctcgacaat ctggggagta tcagcttatg gtattttcgt ttttggtttt       180
ttccttgcac aagttttatt ttcagaactg aacaggaaac gtcttcgcaa gtggatttct       240
ctcagaccta agggttggaa tgatgtccgt ttggctgtga tcattgctgg ataccgcgaa       300
gatccctata tgttccaaaa gtgtctcgag tcagtgcgtg actctgacta cggtaacgtt       360
gctcgtctca tttgtgttat tgacggcgat gacgacgctg atatgaagat gtccgatgtt       420
tacaagacga tctacaacga taatatcaag aagcccgagt ttgtcttgtg tgagtcagac       480
gacaaggaag gtgaacgcat cgactctgat ttctctcgcg acatttgtgt tctccagcct       540
```

```
caccgtggca agagggagtg tctctatact ggtttccaac ttgcaaagat ggacccccagt    600 gtcaacgccg tcgttttgat tgacagcgat actgttctcg agaaggatgc tattctggaa    660
gttgtatacc cacttgcatg cgatcctgag atccaagccg tcgcaggtga gtgtaagatt    720
tggaacacag acactctttt gagtcttctc gtcgcttggc ggtactattc tgcgttttgt    780
gtggagagga gtgcccagtc ttttttcagg actgttcagt gcgttggggg cccgctgggt    840
gcctacaaga ttgatatcat taaggagatt aaggacccct ggatttccca gcgctttctt    900
ggtcagaagt gtacttacgg tgacgaccgc cggctaacca acgagatctt gatgcgtggt    960
aaaaaggttg tgttcactcc atttgctgtt ggttggtctg acagtccgac caatgtgttt   1020
cgatacatcg ttcagcagac ccgctggagt aagtcgtggt gccgcgaaat ttggtacacc   1080
ctcttcgccg cgtggaagca cggtttgtct ggaatttggc tggcctttga atgtttgtat   1140
caaattacat acttcttcct cgtgatttac ctctttttctc gcctagccgt tgaggccgac   1200
cctcgctccc agacagccac agtgattgtg agcaccacgg ttgcattgat taagtgtggg   1260 tattttttcat tccgagccaa ggatattcgg gcttttttact ttgtgcttta tacatttgtt   1320 tacttttttct gtatgattcc ggccagggtt actgcaatga tgacgctttg gacattggc    1380 tggggtactc gcggtggaaa cgagaagcct tccgttggca cccgggtcgc tctgtgggca   1440
aagcaatatc tcattgcata tatgtggtgg gccgcggttg ttggcgctgg agtttacagc   1500
atcgtccata actggatgtt cgattggaat tctctttctt atcgtttttgc tttggttggt   1560 atttgttctt acattgtttt tattactatt gtgctggtga tttattttcac cggcaaaatt   1620 acgacttgga atttcacgaa gcttcagaag gagctaatcg aggatcgtgt tctgtacgat   1680
gcatctacca atgctcagtc tgtgtga                                         1707
```

<210> SEQ ID NO 2
<211> LENGTH: 568
<212> TYPE: PRT
<213> ORGANISM: Chlorella virus

<400> SEQUENCE: 2

```
Met Gly Lys Asn Ile Ile Ile Met Val Ser Trp Tyr Thr Ile Ile Thr
1               5                  10                  15

Ser Asn Leu Ile Ala Val Gly Gly Ala Ser Leu Ile Leu Ala Pro Ala
            20                  25                  30

Ile Thr Gly Tyr Ile Leu His Trp Asn Ile Ala Leu Ser Thr Ile Trp
        35                  40                  45

Gly Val Ser Ala Tyr Gly Ile Phe Val Phe Gly Phe Phe Leu Ala Gln
    50                  55                  60

Val Leu Phe Ser Glu Leu Asn Arg Lys Arg Leu Arg Lys Trp Ile Ser
65                  70                  75                  80

Leu Arg Pro Lys Gly Trp Asn Asp Val Arg Leu Ala Val Ile Ile Ala
                85                  90                  95

Gly Tyr Arg Glu Asp Pro Tyr Met Phe Gln Lys Cys Leu Glu Ser Val
            100                 105                 110

Arg Asp Ser Asp Tyr Gly Asn Val Ala Arg Leu Ile Cys Val Ile Asp
        115                 120                 125

Gly Asp Asp Asp Ala Asp Met Lys Met Ser Asp Val Tyr Lys Thr Ile
    130                 135                 140

Tyr Asn Asp Asn Ile Lys Lys Pro Glu Phe Val Leu Cys Glu Ser Asp
145                 150                 155                 160

Asp Lys Glu Gly Glu Arg Ile Asp Ser Asp Phe Ser Arg Asp Ile Cys
```

```
                165                 170                 175
Val Leu Gln Pro His Arg Gly Lys Arg Glu Cys Leu Tyr Thr Gly Phe
            180                 185                 190
Gln Leu Ala Lys Met Asp Pro Ser Val Asn Ala Val Val Leu Ile Asp
            195                 200                 205
Ser Asp Thr Val Leu Glu Lys Asp Ala Ile Leu Glu Val Val Tyr Pro
210                 215                 220
Leu Ala Cys Asp Pro Glu Ile Gln Ala Val Ala Gly Glu Cys Lys Ile
225                 230                 235                 240
Trp Asn Thr Asp Thr Leu Leu Ser Leu Leu Val Ala Trp Arg Tyr Tyr
                245                 250                 255
Ser Ala Phe Cys Val Glu Arg Ser Ala Gln Ser Phe Phe Arg Thr Val
            260                 265                 270
Gln Cys Val Gly Gly Pro Leu Gly Ala Tyr Lys Ile Asp Ile Ile Lys
            275                 280                 285
Glu Ile Lys Asp Pro Trp Ile Ser Gln Arg Phe Leu Gly Gln Lys Cys
            290                 295                 300
Thr Tyr Gly Asp Asp Arg Arg Leu Thr Asn Glu Ile Leu Met Arg Gly
305                 310                 315                 320
Lys Lys Val Val Phe Thr Pro Phe Ala Val Gly Trp Ser Asp Ser Pro
                325                 330                 335
Thr Asn Val Phe Arg Tyr Ile Val Gln Gln Thr Arg Trp Ser Lys Ser
            340                 345                 350
Trp Cys Arg Glu Ile Trp Tyr Thr Leu Phe Ala Ala Trp Lys His Gly
            355                 360                 365
Leu Ser Gly Ile Trp Leu Ala Phe Glu Cys Leu Tyr Gln Ile Thr Tyr
            370                 375                 380
Phe Phe Leu Val Ile Tyr Leu Phe Ser Arg Leu Ala Val Glu Ala Asp
385                 390                 395                 400
Pro Arg Ser Gln Thr Ala Thr Val Ile Val Ser Thr Thr Val Ala Leu
                405                 410                 415
Ile Lys Cys Gly Tyr Phe Ser Phe Arg Ala Lys Asp Ile Arg Ala Phe
            420                 425                 430
Tyr Phe Val Leu Tyr Thr Phe Val Tyr Phe Phe Cys Met Ile Pro Ala
            435                 440                 445
Arg Val Thr Ala Met Met Thr Leu Trp Asp Ile Gly Trp Gly Thr Arg
            450                 455                 460
Gly Gly Asn Glu Lys Pro Ser Val Gly Thr Arg Val Ala Leu Trp Ala
465                 470                 475                 480
Lys Gln Tyr Leu Ile Ala Tyr Met Trp Trp Ala Ala Val Val Gly Ala
                485                 490                 495
Gly Val Tyr Ser Ile Val His Asn Trp Met Phe Asp Trp Asn Ser Leu
            500                 505                 510
Ser Tyr Arg Phe Ala Leu Val Gly Ile Cys Ser Tyr Ile Val Phe Ile
            515                 520                 525
Thr Ile Val Leu Val Ile Tyr Phe Thr Gly Lys Ile Thr Thr Trp Asn
            530                 535                 540
Phe Thr Lys Leu Gln Lys Glu Leu Ile Glu Asp Arg Val Leu Tyr Asp
545                 550                 555                 560
Ala Ser Thr Asn Ala Gln Ser Val
                565

<210> SEQ ID NO 3
<211> LENGTH: 1707
```

<212> TYPE: DNA
<213> ORGANISM: Chlorella virus

<400> SEQUENCE: 3

```
atgggtaaaa atataatcat aatggtttcg tggtacacca tcataacttc aaatctaatc    60
gcggttggag gagcctctct aatcttggct ccagcaatta ctggatatat tctacattgg   120
aatattgctc tctcgacaat ctggggagta tcagcttatg gtattttcgt ttttggtttt   180
ttccttgcac aagttttatt ttcagaactg aacaggaaac gtcttcgcaa atggatttct   240
ctcagaccta agggttggaa tgatgtccgt ttggctgtga tcattgctgg ataccgcgaa   300
gatccctata tgttccaaaa gtgtctcgag tcagtgcgtg actctgacta cggtaacgtt   360
gctcgtctca tttgtgttat tgacggcgat gacgacgctg atatgaagat gtccgatgtt   420
tacaagacga tctacaacga taatatcaag aagcccgagt tgtcttgtg tgagtcagac   480
gacaaggaag gtgaacgcat cgactctgat ttctctcgcg acatttgtgt tctccagcct   540
caccgtggca agagggagtg tctctatact ggtttccaac ttgcaaagat ggaccccagt   600
gtcaacgccg tcgttttgat tgacagcgat actgttctcg agaaggatgc tattctggaa   660
gttgtatacc cacttgcatg cgatcctgag atccaagccg tcgcaggtga gtgtaagatt   720
tggaacacag acactctttt gagtcttctc gtcgcttggc ggtactattc tgcgttttgt   780
gtggagagga gtgcccagtc tttttttcagg actgttcagt gcgttggggg cccgctgggg   840
gcctacaaga ttgatatcat taaggagatt aaggacccct ggatttccca gcgctttctt   900
ggtcagaagt gtacttacgg tgacgaccgc cggctaacca acgagatctt gatgcgtggt   960
aaaaaggttg tgttcactcc atttgctgtt ggttggtctg acagtccgac caatgtgttt  1020
cgatacatcg ttcagcagac ccgctggagt aagtcgtggt gccgcgaaat ttggtacacc  1080
ctctttgccg cgtggaagca cggtttgtct ggaatttggc tggcctttga atgtttgtat  1140
caaattacat acttcttcct cgtgatttac ctcttttctc gcctagccgt tgaagccgac  1200
cctcgctccc agacagccac agtgattgtg agcaccacgg ttgcattgat taagtgtggg  1260
tatttttcat tccgagccaa ggatattcgg gcttttttact ttgtgcttta tacatttgtt  1320
tacttttttct gtatgattcc ggccagggtt actgcaatga tgacgctttg ggacattggc  1380
tggggtactc gcggtggaaa cgagaagcct tccgttggca cccgggtcgc tctgtgggca  1440
aagcaatatc tcattgcata tatgtggtgg gccgcggttg ttggcgctgg agtttacagc  1500
atcgtccata actggatgtt cgattggaat tctctttctt atcgttttgc tttggttggt  1560
atttgttctt acattgtttt tattactatt gtgctggtga tttatttcac cggcaaaatt  1620
acgacttgga atttcacgaa gcttcagaag gagctaatcg aggatcgtgt tctgtacgat  1680
gcatctacca atgctcagtc tgtgtga                                        1707
```

<210> SEQ ID NO 4
<211> LENGTH: 568
<212> TYPE: PRT
<213> ORGANISM: Chlorella virus

<400> SEQUENCE: 4

```
Met Gly Lys Asn Ile Ile Ile Met Val Ser Trp Tyr Thr Ile Ile Thr
  1               5                  10                  15
Ser Asn Leu Ile Ala Val Gly Gly Ala Ser Leu Ile Leu Ala Pro Ala
             20                  25                  30
Ile Thr Gly Tyr Ile Leu His Trp Asn Ile Ala Leu Ser Thr Ile Trp
         35                  40                  45
```

-continued

```
Gly Val Ser Ala Tyr Gly Ile Phe Val Phe Gly Phe Phe Leu Ala Gln
    50                  55                  60

Val Leu Phe Ser Glu Leu Asn Arg Lys Arg Leu Arg Lys Trp Ile Ser
65                  70                  75                  80

Leu Arg Pro Lys Gly Trp Asn Asp Val Arg Leu Ala Val Ile Ile Ala
                85                  90                  95

Gly Tyr Arg Glu Asp Pro Tyr Met Phe Gln Lys Cys Leu Glu Ser Val
            100                 105                 110

Arg Asp Ser Asp Tyr Gly Asn Val Ala Arg Leu Ile Cys Val Ile Asp
        115                 120                 125

Gly Asp Asp Ala Asp Met Lys Met Ser Asp Val Tyr Lys Thr Ile
    130                 135                 140

Tyr Asn Asp Asn Ile Lys Lys Pro Glu Phe Val Leu Cys Glu Ser Asp
145                 150                 155                 160

Asp Lys Glu Gly Glu Arg Ile Asp Ser Asp Phe Ser Arg Asp Ile Cys
                165                 170                 175

Val Leu Gln Pro His Arg Gly Lys Arg Glu Cys Leu Tyr Thr Gly Phe
            180                 185                 190

Gln Leu Ala Lys Met Asp Pro Ser Val Asn Ala Val Leu Ile Asp
        195                 200                 205

Ser Asp Thr Val Leu Glu Lys Asp Ala Ile Leu Glu Val Val Tyr Pro
    210                 215                 220

Leu Ala Cys Asp Pro Glu Ile Gln Ala Val Ala Gly Glu Cys Lys Ile
225                 230                 235                 240

Trp Asn Thr Asp Thr Leu Leu Ser Leu Leu Val Ala Trp Arg Tyr Tyr
                245                 250                 255

Ser Ala Phe Cys Val Glu Arg Ser Ala Gln Ser Phe Phe Arg Thr Val
            260                 265                 270

Gln Cys Val Gly Gly Pro Leu Gly Ala Tyr Lys Ile Asp Ile Ile Lys
        275                 280                 285

Glu Ile Lys Asp Pro Trp Ile Ser Gln Arg Phe Leu Gly Gln Lys Cys
    290                 295                 300

Thr Tyr Gly Asp Asp Arg Arg Leu Thr Asn Glu Ile Leu Met Arg Gly
305                 310                 315                 320

Lys Lys Val Val Phe Thr Pro Phe Ala Val Gly Trp Ser Asp Ser Pro
                325                 330                 335

Thr Asn Val Phe Arg Tyr Ile Val Gln Gln Thr Arg Trp Ser Lys Ser
            340                 345                 350

Trp Cys Arg Glu Ile Trp Tyr Thr Leu Phe Ala Ala Trp Lys His Gly
        355                 360                 365

Leu Ser Gly Ile Trp Leu Ala Phe Glu Cys Leu Tyr Gln Ile Thr Tyr
    370                 375                 380

Phe Phe Leu Val Ile Tyr Leu Phe Ser Arg Leu Ala Val Glu Ala Asp
385                 390                 395                 400

Pro Arg Ser Gln Thr Ala Thr Val Ile Val Ser Thr Val Ala Leu
                405                 410                 415

Ile Lys Cys Gly Tyr Phe Ser Phe Arg Ala Lys Asp Ile Arg Ala Phe
            420                 425                 430

Tyr Phe Val Leu Tyr Thr Phe Val Tyr Phe Cys Met Ile Pro Ala
        435                 440                 445

Arg Val Thr Ala Met Met Thr Leu Trp Asp Ile Gly Trp Gly Thr Arg
    450                 455                 460

Gly Gly Asn Glu Lys Pro Ser Val Gly Thr Arg Val Ala Leu Trp Ala
465                 470                 475                 480
```

-continued

```
Lys Gln Tyr Leu Ile Ala Tyr Met Trp Trp Ala Ala Val Val Gly Ala
            485                 490                 495
Gly Val Tyr Ser Ile Val His Asn Trp Met Phe Asp Trp Asn Ser Leu
            500                 505                 510
Ser Tyr Arg Phe Ala Leu Val Gly Ile Cys Ser Tyr Ile Val Phe Ile
            515                 520                 525
Thr Ile Val Leu Val Ile Tyr Phe Thr Gly Lys Ile Thr Thr Trp Asn
            530                 535                 540
Phe Thr Lys Leu Gln Lys Glu Leu Ile Glu Asp Arg Val Leu Tyr Asp
545                 550                 555                 560
Ala Ser Thr Asn Ala Gln Ser Val
                565

<210> SEQ ID NO 5
<211> LENGTH: 1788
<212> TYPE: DNA
<213> ORGANISM: Chlorella virus

<400> SEQUENCE: 5
atgtgtggca tctttggagc agtgtcaaac aacaactcta tcgaggtgtc aatcaagggt        60
attcagaagc tagaatatcg tgggtatgat tcgtgcggta ttgcgtatac agatgggggt       120
gcgattgagc gtatacggtc ggttgacggt attgacgatc tgcgtaagaa acaatcaca        180 gaatcatcac cagtggccat gctcactcg cggtggagca ccactggaat tccatcagtg       240
gtgaacgcac atcctcatat ttctcgcgga accagtgggg tgagtctcg tatcgcggta       300 gtccacaacg gtatcattga aaactatcag cagatccgaa atatctcat caatctcggt       360 tatacgtttg atagtcaaac ggacacagag gtcattgcac atttgatcga ttctcagtac       420
aatgggaata tcttgcacac cgtccaaatg gctgtcaagc acctgaaggg ctcttatgcc       480
attgcagtta tgtgtcataa agagtctggt aaaatagtcg tggcgaaaca gaagtcaccc       540
ctcgtacttg aatcggctc agatggtgct tactacatcg cttcggacgt gctggcgctg       600
ccgacaaata aagttgttta tatttcagat ggtttctctg cagaactatc tccagggagt       660
atgtccattt acgatcctga tggaaatgaa gtggaatatg aagtagagga cgttgaaatg       720
gaacaaacta gtatgtctct tgataacttt gatcattaca tgattaagga aattaatgag       780
caaccaatca gtatcctaaa cactataaaa aataaagggt tttatgcaga aatattcggc       840
gatttggcgc atgaaatctt ccaaaaaata gacaacatcc tgatactggc ttgtggtaca       900
agttatcacg ccggtcttgt aggaaaacag tggatagaga ccattgcgag aatccccgtg       960
gatgttcaca tcgcgagcga atacgaacct acaattccga gagcgaacac attggtaatc      1020
actatttcac agtcgggtga aactgcggac acgatagcgg ctttgcaacg ggcccaaaac      1080
gccgggatga tttatacatt gtgtatttgc aattcaccaa agagcactct tgttcgcgag      1140
agcgttatga agtacataac gaaatgtggg tctgaggtgt cagtagcatc aacgaaggcg      1200
tttacctcgc aactcgtagt actgtacatg ctggcaaacg tattggcaaa taaaaccgat      1260
gatttgctgg gagacctccc cacaggcaata gaacgggtga tttgtttgac aaatgacgaa      1320
atgaaacact gggcggacga aatctgcaat gcgaaatctg cgatcttcct gggaagagga      1380
ctaaacgcac cagttgcctt tgaggagcg ctgaagctca aagaaatctc ttacattcat      1440
gcagagggct tcctgggagg tgagttgaaa catggccccc tcgcactcct gatgacaaa       1500 attcctgtta tcgtaaccgt agcagatcat gcttatttgg accatatcaa agcaaatatt      1560
gacgaagtgc ttgcgaggaa cgttacggta tacgccatag tagaccagta tgtgaacatc      1620
```
gagccccagg aacgccttcg cgttgtcaag gttccgtttg tatccaaaga atttctccg 1680 ataattcaca ctatcccgat gcaactgctt tcgtattacg tggcaattaa gcttgggaag 1740
aacgttgaca aaccaaggaa tcttgcaaaa tccgtgacca ccttttaa 1788

<210> SEQ ID NO 6
<211> LENGTH: 595
<212> TYPE: PRT
<213> ORGANISM: Chlorella virus

<400> SEQUENCE: 6

Met Cys Gly Ile Phe Gly Ala Val Ser Asn Asn Ser Ile Glu Val
1               5                   10                  15

Ser Ile Lys Gly Ile Gln Lys Leu Glu Tyr Arg Gly Tyr Asp Ser Cys
            20                  25                  30

Gly Ile Ala Tyr Thr Asp Gly Gly Ala Ile Glu Arg Ile Arg Ser Val
        35                  40                  45

Asp Gly Ile Asp Asp Leu Arg Lys Lys Thr Ile Thr Glu Ser Ser Pro
    50                  55                  60

Val Ala Ile Ala His Ser Arg Trp Ser Thr Thr Gly Ile Pro Ser Val
65                  70                  75                  80

Val Asn Ala His Pro His Ile Ser Arg Gly Thr Ser Gly Cys Glu Ser
                85                  90                  95

Arg Ile Ala Val Val His Asn Gly Ile Ile Glu Asn Tyr Gln Gln Ile
            100                 105                 110

Arg Lys Tyr Leu Ile Asn Leu Gly Tyr Thr Phe Asp Ser Gln Thr Asp
            115                 120                 125

Thr Glu Val Ile Ala His Leu Ile Asp Ser Gln Tyr Asn Gly Asn Ile
130                 135                 140

Leu His Thr Val Gln Met Ala Val Lys His Leu Lys Gly Ser Tyr Ala
145                 150                 155                 160

Ile Ala Val Met Cys His Lys Glu Ser Gly Lys Ile Val Val Ala Lys
                165                 170                 175

Gln Lys Ser Pro Leu Val Leu Gly Ile Gly Ser Asp Gly Ala Tyr Tyr
            180                 185                 190

Ile Ala Ser Asp Val Leu Ala Leu Pro Thr Asn Lys Val Val Tyr Ile
        195                 200                 205

Ser Asp Gly Phe Ser Ala Glu Leu Ser Pro Gly Ser Met Ser Ile Tyr
    210                 215                 220

Asp Pro Asp Gly Asn Glu Val Glu Tyr Glu Val Glu Ser Val Glu Met
225                 230                 235                 240

Glu Gln Thr Ser Met Ser Leu Asp Asn Phe Asp His Tyr Met Ile Lys
                245                 250                 255

Glu Ile Asn Glu Gln Pro Ile Ser Ile Leu Asn Thr Ile Lys Asn Lys
            260                 265                 270

Gly Phe Tyr Ala Glu Ile Phe Gly Asp Leu Ala His Glu Ile Phe Gln
        275                 280                 285

Lys Ile Asp Asn Ile Leu Ile Leu Ala Cys Gly Thr Ser Tyr His Ala
    290                 295                 300

Gly Leu Val Gly Lys Gln Trp Ile Glu Thr Ile Ala Arg Ile Pro Val
305                 310                 315                 320

Asp Val His Ile Ala Ser Glu Tyr Glu Pro Thr Ile Pro Arg Ala Asn
                325                 330                 335

Thr Leu Val Ile Thr Ile Ser Gln Ser Gly Glu Thr Ala Asp Thr Ile
            340                 345                 350

```
Ala Ala Leu Gln Arg Ala Gln Asn Ala Gly Met Ile Tyr Thr Leu Cys
        355                 360                 365

Ile Cys Asn Ser Pro Lys Ser Thr Leu Val Arg Glu Ser Val Met Lys
    370                 375                 380

Tyr Ile Thr Lys Cys Gly Ser Glu Val Ser Ala Ser Thr Lys Ala
385                 390                 395                 400

Phe Thr Ser Gln Leu Val Val Leu Tyr Met Leu Ala Asn Val Leu Ala
                405                 410                 415

Asn Lys Thr Asp Asp Leu Leu Gly Asp Leu Pro Gln Ala Ile Glu Arg
            420                 425                 430

Val Ile Cys Leu Thr Asn Asp Glu Met Lys His Trp Ala Asp Glu Ile
            435                 440                 445

Cys Asn Ala Lys Ser Ala Ile Phe Leu Gly Arg Gly Leu Asn Ala Pro
        450                 455                 460

Val Ala Phe Glu Gly Ala Leu Lys Leu Lys Glu Ile Ser Tyr Ile His
465                 470                 475                 480

Ala Glu Gly Phe Leu Gly Gly Glu Leu Lys His Gly Pro Leu Ala Leu
                485                 490                 495

Leu Asp Asp Lys Ile Pro Val Ile Val Thr Val Ala Asp His Ala Tyr
            500                 505                 510

Leu Asp His Ile Lys Ala Asn Ile Asp Glu Val Leu Ala Arg Asn Val
        515                 520                 525

Thr Val Tyr Ala Ile Val Asp Gln Tyr Val Asn Ile Glu Pro Gln Glu
    530                 535                 540

Arg Leu Arg Val Val Lys Val Pro Phe Val Ser Lys Glu Phe Ser Pro
545                 550                 555                 560

Ile Ile His Thr Ile Pro Met Gln Leu Leu Ser Tyr Tyr Val Ala Ile
                565                 570                 575

Lys Leu Gly Lys Asn Val Asp Lys Pro Arg Asn Leu Ala Lys Ser Val
            580                 585                 590

Thr Thr Phe
        595

<210> SEQ ID NO 7
<211> LENGTH: 1788
<212> TYPE: DNA
<213> ORGANISM: Chlorella virus

<400> SEQUENCE: 7
atgtgtggca tctttggagc agtgtcaaac aacaactcta tcgaggtgtc aatcaagggt      60
attcagaagc tagaatatcg tgggtatgat tcgtgcggta ttgcgtatac agatgggggt     120
gcgattgagc gtatacggtc ggttgacggt attgacgatc tgcgtaagaa aacaatcaca     180
gaatcatcac cagtagccat tgctcactcg cggtggagca ccactggaat tccatcagtg     240
gtgaacgcac atcctcatat ttctcgcgga accagtgggt gtgagtctcg tatcgcggta     300
gtccacaacg gtatcattga aaactatcag cagatccgaa aatatctcat caatctcggt     360
tatacgtttg atagtcaaac ggacacagag gtcattgcac atttgatcga ttctcagtac     420
aatgggaata tcttgcacac cgtccaaatg gctgtcaagc acctgaaggg ctcttatgcc     480
attgcagtta tgtgtcataa agagtctggt aaaatagtcg tggcgaaaca gaagtcaccc     540
ctcgtacttg gaatcggctc agatggtgct tactacatcg cttcggacgt gctggcgctg     600
ccgacaaata aagttgttta tatttcgat ggtttctctg cagaactatc tccagggagt     660
atgtccattt acgatcctga tggaaatgaa gtggaatatg aagtagagga cgttgaaatg     720
```

```
gaacaaacta gtatgtctct ctataacttt gatcattaca tgattaagga aattaatgag    780
caaccaatca gtatcctaaa cactataaaa aataaagggt tctatgcaga aatattcggt    840
gatttggcgc atgaaatctt ccaaaaaata gacaacatcc tggtactggc ttgtggtaca    900
agttatcacg ccggtctcgt cgggaaacag tggatagaga ccatcgcgaa atccccgtg    960 aatgttcata tcgcaagtga atacgaaccc accattccta aagcgaacac attggtaatc   1020
actatttcac aatcgggtga aactgcggac acgatagcgg ctttgcaacg agcccaaaac   1080
gccgggatga tttacacact gtgtatttgc aattctccaa agagtactct agttcgcgag   1140
agcattatga agtacatcac taaatgtggt tctgaggtgt cagtagcatc aacgaaggcg   1200
tttacctcgc agctcgtagt actgtatatc ctggcaaacg tattggcaaa taaaaccgac   1260
gatttgctgg gtgagcttcc gcaagcaata gaacgggtga tttgtttgac gagcgatgaa   1320
atgaaacaat gggctgatga atatgcaat gcgaaatctg cgatcttcct ggggagagga   1380
ctgaacgcac cagttgcttt tgagggtgcg ttgaaactca aagagatttc ttacattcat   1440
gcggagggct tcctgggagg tgagttgaaa cacggtcccc tcgcactcct tgatgacaag   1500
attcctgtca tcgtaactgt ggcagatcat gcttatctgg accatatcaa agcaaatatt   1560
gacgaagtgc ttgcgaggaa cgtcacggta tatgccattg ttgaccagta tgtgaacatc   1620
gagccccagg aacgtcttca tatcgtcaag gttccgtttg tgtcaaaaga attttctcca   1680
ataattcaca ctatcccaat gcaactgctt tcgtattacg tggcaattaa gcttggaaag   1740
aatgttgata aaccgaggaa tcttgcgaaa tctgtgacca ccttttaa              1788
```

<210> SEQ ID NO 8
<211> LENGTH: 595
<212> TYPE: PRT
<213> ORGANISM: Chlorella virus

<400> SEQUENCE: 8

```
Met Cys Gly Ile Phe Gly Ala Val Ser Asn Asn Ser Ile Glu Val
1               5                   10                  15

Ser Ile Lys Gly Ile Gln Lys Leu Glu Tyr Arg Gly Tyr Asp Ser Cys
            20                  25                  30

Gly Ile Ala Tyr Thr Asp Gly Gly Ala Ile Glu Arg Ile Arg Ser Val
        35                  40                  45

Asp Gly Ile Asp Asp Leu Arg Lys Lys Thr Ile Thr Glu Ser Ser Pro
    50                  55                  60

Val Ala Ile Ala His Ser Arg Trp Ser Thr Thr Gly Ile Pro Ser Val
65                  70                  75                  80

Val Asn Ala His Pro His Ile Ser Arg Gly Thr Ser Gly Cys Glu Ser
                85                  90                  95

Arg Ile Ala Val Val His Asn Gly Ile Ile Glu Asn Tyr Gln Gln Ile
            100                 105                 110

Arg Lys Tyr Leu Ile Asn Leu Gly Tyr Thr Phe Asp Ser Gln Thr Asp
        115                 120                 125

Thr Glu Val Ile Ala His Leu Ile Asp Ser Gln Tyr Asn Gly Asn Ile
    130                 135                 140

Leu His Thr Val Gln Met Ala Val Lys His Leu Lys Gly Ser Tyr Ala
145                 150                 155                 160

Ile Ala Val Met Cys His Lys Glu Ser Gly Lys Ile Val Val Ala Lys
                165                 170                 175

Gln Lys Ser Pro Leu Val Leu Gly Ile Gly Ser Asp Gly Ala Tyr Tyr
            180                 185                 190
```

```
Ile Ala Ser Asp Val Leu Ala Leu Pro Thr Asn Lys Val Val Tyr Ile
        195                 200                 205

Ser Asp Gly Phe Ser Ala Glu Leu Ser Pro Gly Ser Met Ser Ile Tyr
    210                 215                 220

Asp Pro Asp Gly Asn Glu Val Glu Tyr Glu Val Asp Val Glu Met
225                 230                 235                 240

Glu Gln Thr Ser Met Ser Leu Tyr Asn Phe Asp His Tyr Met Ile Lys
                245                 250                 255

Glu Ile Asn Glu Gln Pro Ile Ser Ile Leu Asn Thr Ile Lys Asn Lys
            260                 265                 270

Gly Phe Tyr Ala Glu Ile Phe Gly Asp Leu Ala His Glu Ile Phe Gln
        275                 280                 285

Lys Ile Asp Asn Ile Leu Val Leu Ala Cys Gly Thr Ser Tyr His Ala
        290                 295                 300

Gly Leu Val Gly Lys Gln Trp Ile Glu Thr Ile Ala Lys Ile Pro Val
305                 310                 315                 320

Asn Val His Ile Ala Ser Glu Tyr Glu Pro Thr Ile Pro Lys Ala Asn
                325                 330                 335

Thr Leu Val Ile Thr Ile Ser Gln Ser Gly Glu Thr Ala Asp Thr Ile
            340                 345                 350

Ala Ala Leu Gln Arg Ala Gln Asn Ala Gly Met Ile Tyr Thr Leu Cys
        355                 360                 365

Ile Cys Asn Ser Pro Lys Ser Thr Leu Val Arg Glu Ser Ile Met Lys
        370                 375                 380

Tyr Ile Thr Lys Cys Gly Ser Glu Val Ser Val Ala Ser Thr Lys Ala
385                 390                 395                 400

Phe Thr Ser Gln Leu Val Val Leu Tyr Ile Leu Ala Asn Val Leu Ala
                405                 410                 415

Asn Lys Thr Asp Asp Leu Leu Gly Glu Leu Pro Gln Ala Ile Glu Arg
            420                 425                 430

Val Ile Cys Leu Thr Ser Asp Glu Met Lys Gln Trp Ala Asp Glu Ile
        435                 440                 445

Cys Asn Ala Lys Ser Ala Ile Phe Leu Gly Arg Gly Leu Asn Ala Pro
        450                 455                 460

Val Ala Phe Glu Gly Ala Leu Lys Leu Lys Glu Ile Ser Tyr Ile His
465                 470                 475                 480

Ala Glu Gly Phe Leu Gly Gly Glu Leu Lys His Gly Pro Leu Ala Leu
                485                 490                 495

Leu Asp Asp Lys Ile Pro Val Ile Val Thr Val Ala Asp His Ala Tyr
            500                 505                 510

Leu Asp His Ile Lys Ala Asn Ile Asp Glu Val Leu Ala Arg Asn Val
        515                 520                 525

Thr Val Tyr Ala Ile Val Asp Gln Tyr Val Asn Ile Glu Pro Gln Glu
    530                 535                 540

Arg Leu His Ile Val Lys Val Pro Phe Val Ser Lys Glu Phe Ser Pro
545                 550                 555                 560

Ile Ile His Thr Ile Pro Met Gln Leu Leu Ser Tyr Tyr Val Ala Ile
                565                 570                 575

Lys Leu Gly Lys Asn Val Asp Lys Pro Arg Asn Leu Ala Lys Ser Val
            580                 585                 590

Thr Thr Phe
    595
```

<210> SEQ ID NO 9
<211> LENGTH: 2034
<212> TYPE: DNA
<213> ORGANISM: Arabidopsis thaliana

<400> SEQUENCE: 9

| | | | | | | |
|---|---|---|---|---|---|---|
| atgtgtggaa | tcttcgcgta | tctgaatttt | cacgcgaaca | agagagacg | atacattctc | 60 |
| gatgttctct | tcaatggtct | tcgtcgtctt | gaatacagag | gctacgattc | tgctggaatc | 120 |
| gccattgata | attcttctcc | ttcttcttct | cctctcgtgt | ttcgtcaagc | aggaaacatt | 180 |
| gaatcacttg | ttaattccgt | taacgaagag | attacgaata | cggatttgaa | tctagacgaa | 240 |
| gttttctact | ttcatgctgg | aattgcacat | acgaggtggg | ctactcatgg | tgagccagct | 300 |
| ccaaggaata | gtcatcctca | atcttctggt | cctggagatg | attttttggt | ggttcataat | 360 |
| ggtgttatca | ctaactatga | ggtattgaaa | gaaacgttag | tgaggcatgg | atttactttt | 420 |
| gaatcggaca | cagatactga | agtaattcct | aagcttgcta | agtttgtttt | tgacaaagct | 480 |
| aatgaagaag | gtggacaaac | tgttacattc | tgtgaagttg | tgtttgaagt | gatgaggcat | 540 |
| cttgaaggag | cttatgctct | tatatttaaa | agctggcatt | atccgaatga | gttaattgcg | 600 |
| tgcaagcttg | gtagtccatt | gcttttaggt | gttaaagagc | tagatcaagg | tgagagcaat | 660 |
| agtcatgttt | tccaagatgc | tcactttcta | tctaagaatg | accatcccaa | ggagtttttc | 720 |
| ctatcaagtg | atccacatgc | tcttgttgag | cacacaaaga | aagttttggt | gattgaagat | 780 |
| ggcgaagttg | tcaatctcaa | ggatggaggt | gtatcaatac | ttaagtttga | aaatgagagg | 840 |
| ggaaggtgta | atggtttatc | gagacctgct | tcagtggaac | gtgccttatc | tgttctagag | 900 |
| atggaggtag | agcaaataag | caagggaaaa | tatgatcatt | acatgcaaaa | ggaaatccac | 960 |
| gagcagccag | aatctttaac | tactacaatg | agaggccgac | ttatacgcgg | tggttcacgt | 1020 |
| aaaacgaaaa | ccgtcctctt | aggtgggctg | aaagatcacc | taaagaccat | aagacgcagc | 1080 |
| cggcgtatag | ttttattgg | atgtgggaca | agttacaatg | ccgctcttgc | atcaagacct | 1140 |
| atccttgaag | aactctctgg | tataccagtc | agtatggaga | ttgctagtga | tctatgggac | 1200 |
| cggcaaggtc | caatatacag | agaagatacc | gcggtgtttg | tgagtcagtc | tggtgaaact | 1260 |
| gcagatacac | tacttgcttt | ggactatgct | cgagaaaacg | gtgcattatg | tgtcggcata | 1320 |
| actaacaccg | ttgggagctc | catagctaga | aaaacacact | gtggtgtcca | tataaacgca | 1380 |
| ggagctgaga | ttggtgtcgc | aagtacaaag | gcatatacaa | gtcagattgt | ggtaatggta | 1440 |
| atgctagctt | tagcaatagg | aagtgacaca | atctccagcc | aaaagagacg | ggaagctata | 1500 |
| atcgatggac | tacttgattt | gccgtataag | gttaaggaag | tactaaagct | agacgatgaa | 1560 |
| atgaaagatc | tcgcgcaact | cttgatagac | gagcagtcac | tgctagtgtt | tggcagagga | 1620 |
| tacaactacg | caacagcttt | agaaggagca | ttaaaagtaa | aagaagtagc | acttatgcac | 1680 |
| agtgaaggaa | tacttgcagg | agaaatgaaa | catggacctt | tagctttggt | tgatgagaat | 1740 |
| ctcccccatag | ctgtgattgc | cactcgtgat | gcttgtttca | gtaaacaaca | atctgtgatt | 1800 |
| cagcaacttc | acgcacgcaa | agggagacta | atagtaatgt | gctcaaaagg | tgatgctgca | 1860 |
| tcggtaagct | cgagtggttc | ttgtcgagct | atcgaagttc | ctcaagttga | agattgttta | 1920 |
| caacctgtta | ttaatatagt | gccattacag | ttgttggctt | atcatctgac | tgttttgaga | 1980 |
| ggtcacaatg | ttgatcaacc | gaggaatctg | gcaaagagtg | tgactactca | atag | 2034 |

<210> SEQ ID NO 10
<211> LENGTH: 677
<212> TYPE: PRT
<213> ORGANISM: Arabidopsis thaliana

```
<400> SEQUENCE: 10

Met Cys Gly Ile Phe Ala Tyr Leu Asn Phe His Ala Asn Lys Glu Arg
1               5                   10                  15

Arg Tyr Ile Leu Asp Val Leu Phe Asn Gly Leu Arg Arg Leu Glu Tyr
            20                  25                  30

Arg Gly Tyr Asp Ser Ala Gly Ile Ala Ile Asp Asn Ser Ser Pro Ser
        35                  40                  45

Ser Ser Pro Leu Val Phe Arg Gln Ala Gly Asn Ile Glu Ser Leu Val
    50                  55                  60

Asn Ser Val Asn Glu Glu Ile Thr Asn Thr Asp Leu Asn Leu Asp Glu
65                  70                  75                  80

Val Phe Tyr Phe His Ala Gly Ile Ala His Thr Arg Trp Ala Thr His
                85                  90                  95

Gly Glu Pro Ala Pro Arg Asn Ser His Pro Gln Ser Ser Gly Pro Gly
            100                 105                 110

Asp Asp Phe Leu Val Val His Asn Gly Val Ile Thr Asn Tyr Glu Val
        115                 120                 125

Leu Lys Glu Thr Leu Val Arg His Gly Phe Thr Phe Glu Ser Asp Thr
130                 135                 140

Asp Thr Glu Val Ile Pro Lys Leu Ala Lys Phe Val Phe Asp Lys Ala
145                 150                 155                 160

Asn Glu Glu Gly Gly Gln Thr Val Thr Phe Cys Glu Val Val Phe Glu
                165                 170                 175

Val Met Arg His Leu Glu Gly Ala Tyr Ala Leu Ile Phe Lys Ser Trp
            180                 185                 190

His Tyr Pro Asn Glu Leu Ile Ala Cys Lys Leu Gly Ser Pro Leu Leu
        195                 200                 205

Leu Gly Val Lys Glu Leu Asp Gln Gly Glu Ser Asn Ser His Val Phe
    210                 215                 220

Gln Asp Ala His Phe Leu Ser Lys Asn Asp His Pro Lys Glu Phe Phe
225                 230                 235                 240

Leu Ser Ser Asp Pro His Ala Leu Val Glu His Thr Lys Lys Val Leu
                245                 250                 255

Val Ile Glu Asp Gly Glu Val Val Asn Leu Lys Asp Gly Gly Val Ser
            260                 265                 270

Ile Leu Lys Phe Glu Asn Glu Arg Gly Arg Cys Asn Gly Leu Ser Arg
        275                 280                 285

Pro Ala Ser Val Glu Arg Ala Leu Ser Val Leu Glu Met Glu Val Glu
    290                 295                 300

Gln Ile Ser Lys Gly Lys Tyr Asp His Tyr Met Gln Lys Glu Ile His
305                 310                 315                 320

Glu Gln Pro Glu Ser Leu Thr Thr Thr Met Arg Gly Arg Leu Ile Arg
                325                 330                 335

Gly Gly Ser Arg Lys Thr Lys Thr Val Leu Leu Gly Leu Lys Asp
            340                 345                 350

His Leu Lys Thr Ile Arg Arg Ser Arg Arg Ile Val Phe Ile Gly Cys
        355                 360                 365

Gly Thr Ser Tyr Asn Ala Ala Leu Ala Ser Arg Pro Ile Leu Glu Glu
    370                 375                 380

Leu Ser Gly Ile Pro Val Ser Met Glu Ile Ala Ser Asp Leu Trp Asp
385                 390                 395                 400

Arg Gln Gly Pro Ile Tyr Arg Glu Asp Thr Ala Val Phe Val Ser Gln
                405                 410                 415
```

Ser Gly Glu Thr Ala Asp Thr Leu Leu Ala Leu Asp Tyr Ala Arg Glu
        420                  425                430

Asn Gly Ala Leu Cys Val Gly Ile Thr Asn Thr Val Gly Ser Ser Ile
        435                  440              445

Ala Arg Lys Thr His Cys Gly Val His Ile Asn Ala Gly Ala Glu Ile
        450                  455              460

Gly Val Ala Ser Thr Lys Ala Tyr Thr Ser Gln Ile Val Val Met Val
465                470              475              480

Met Leu Ala Leu Ala Ile Gly Ser Asp Thr Ile Ser Ser Gln Lys Arg
        485                  490              495

Arg Glu Ala Ile Ile Asp Gly Leu Leu Asp Leu Pro Tyr Lys Val Lys
        500                  505              510

Glu Val Leu Lys Leu Asp Asp Glu Met Lys Asp Leu Ala Gln Leu Leu
        515                  520              525

Ile Asp Glu Gln Ser Leu Leu Val Phe Gly Arg Gly Tyr Asn Tyr Ala
        530                  535              540

Thr Ala Leu Glu Gly Ala Leu Lys Val Lys Glu Val Ala Leu Met His
545                550              555              560

Ser Glu Gly Ile Leu Ala Gly Glu Met Lys His Gly Pro Leu Ala Leu
        565                  570              575

Val Asp Glu Asn Leu Pro Ile Ala Val Ile Ala Thr Arg Asp Ala Cys
        580                  585              590

Phe Ser Lys Gln Gln Ser Val Ile Gln Gln Leu His Ala Arg Lys Gly
        595                  600              605

Arg Leu Ile Val Met Cys Ser Lys Gly Asp Ala Ala Ser Val Ser Ser
        610                  615              620

Ser Gly Ser Cys Arg Ala Ile Glu Val Pro Gln Val Glu Asp Cys Leu
625                630              635              640

Gln Pro Val Ile Asn Ile Val Pro Leu Gln Leu Leu Ala Tyr His Leu
        645                  650              655

Thr Val Leu Arg Gly His Asn Val Asp Gln Pro Arg Asn Leu Ala Lys
        660                  665              670

Ser Val Thr Thr Gln
        675

<210> SEQ ID NO 11
<211> LENGTH: 1170
<212> TYPE: DNA
<213> ORGANISM: Chlorella virus

<400> SEQUENCE: 11

```
atgtcacgaa tcgcagtcgt tggttgtggt tacgtcggaa ccgcttgtgc agtacttctt      60
gctcaaaaaa acgaagtcac cgtgcttgat attagcgaag accgtgttca gctaatcaag     120
aacaagaaga gtccaatcga ggacaaggaa atcgaagagt tctcgaaaac gaaagacctg     180
aacctgaccg cgacgactga caaggttctt gcatacgaaa acgccgaatt tgtcatcatc     240
gcaaccccga ctgactatga cgtggttact aggtatttta acacgaaatc tgtggaaagc     300
gttatcgggg atgtgatcaa aaatacacgg acccagccaa ctattgtgat taaatctacc     360
atccccattg gatttgttga taaggttcgt gagcaattca actacagcaa cattatattc     420
tctccggagt ttctgcgaga aggtagggca ttgtatgata atctctatcc atcgcgtatt     480
atcgtaggag atgattcccc cattgcgctt aagttcgcaa accttctcgt tgaaggttct     540
aaaaccccac ttgcacctgt cctgacgatg gggactcgtg aagccgaggc cgtcaaacta     600
```

-continued

```
ttctctaaca cgtatcttgc gatgcgagtt gcatatttca acgaactaga tacgtttgca    660
ttgtctcatg gtatgagtgc gaaagaaatc attgacggtg tgactctgga gcctcgaatt    720
ggtcagggtt actcaaaccc ttcgttcggt tacggagctt attgcttccc aaaggatacg    780
aagcaacttc tggctaactt tgaggggtg cctcaaaata tcatcggggc aattgtagaa     840
tcaaatgaaa ctcgcaagga agcgattgta agtgaagtag aaaatcgttt tcccacgact    900
gttggtgtgt ataagctcgc tgctaaagcg ggttctgata attttaggag ttctgcaatt    960
gtagacataa tggagcgact tgcaaacagg ggttatcaca ttaagatttt cgaaccaact   1020
gtggaacaat tcgaaaactt tgaagttgat aacaacctga caacatttgc gactgagagc   1080
gatgtaatta tcgcaaacag agttcccgtt gaacatcgca ttctctttgg taaaaaattg   1140
atcacacgtg atgtatatgg cgataactaa                                    1170
```

<210> SEQ ID NO 12
<211> LENGTH: 389
<212> TYPE: PRT
<213> ORGANISM: Chlorella virus

<400> SEQUENCE: 12

```
Met Ser Arg Ile Ala Val Val Gly Cys Gly Tyr Val Gly Thr Ala Cys
1               5                   10                  15

Ala Val Leu Leu Ala Gln Lys Asn Glu Val Thr Val Leu Asp Ile Ser
            20                  25                  30

Glu Asp Arg Val Gln Leu Ile Lys Asn Lys Ser Pro Ile Glu Asp
        35                  40                  45

Lys Glu Ile Glu Glu Phe Leu Glu Thr Lys Asp Leu Asn Leu Thr Ala
    50                  55                  60

Thr Thr Asp Lys Val Leu Ala Tyr Glu Asn Ala Glu Phe Val Ile Ile
65                  70                  75                  80

Ala Thr Pro Thr Asp Tyr Asp Val Val Thr Arg Tyr Phe Asn Thr Lys
                85                  90                  95

Ser Val Glu Ser Val Ile Gly Asp Val Ile Lys Asn Thr Arg Thr Gln
            100                 105                 110

Pro Thr Ile Val Ile Lys Ser Thr Ile Pro Ile Gly Phe Val Asp Lys
        115                 120                 125

Val Arg Glu Gln Phe Asn Tyr Ser Asn Ile Ile Phe Ser Pro Glu Phe
    130                 135                 140

Leu Arg Glu Gly Arg Ala Leu Tyr Asp Asn Leu Tyr Pro Ser Arg Ile
145                 150                 155                 160

Ile Val Gly Asp Asp Ser Pro Ile Ala Leu Lys Phe Ala Asn Leu Leu
                165                 170                 175

Val Glu Gly Ser Lys Thr Pro Leu Ala Pro Val Leu Thr Met Gly Thr
            180                 185                 190

Arg Glu Ala Glu Ala Val Lys Leu Phe Ser Asn Thr Tyr Leu Ala Met
        195                 200                 205

Arg Val Ala Tyr Phe Asn Glu Leu Asp Thr Phe Ala Leu Ser His Gly
    210                 215                 220

Met Ser Ala Lys Glu Ile Ile Asp Gly Val Thr Leu Glu Pro Arg Ile
225                 230                 235                 240

Gly Gln Gly Tyr Ser Asn Pro Ser Phe Gly Tyr Gly Ala Tyr Cys Phe
                245                 250                 255

Pro Lys Asp Thr Lys Gln Leu Leu Ala Asn Phe Glu Gly Val Pro Gln
            260                 265                 270

Asn Ile Ile Gly Ala Ile Val Glu Ser Asn Glu Thr Arg Lys Glu Ala
```

```
                275                 280                 285
Ile Val Ser Glu Val Glu Asn Arg Phe Pro Thr Thr Val Gly Val Tyr
            290                 295                 300
Lys Leu Ala Ala Lys Ala Gly Ser Asp Asn Phe Arg Ser Ser Ala Ile
305                 310                 315                 320
Val Asp Ile Met Glu Arg Leu Ala Asn Arg Gly Tyr His Ile Lys Ile
                325                 330                 335
Phe Glu Pro Thr Val Glu Gln Phe Glu Asn Phe Glu Val Asp Asn Asn
            340                 345                 350
Leu Thr Thr Phe Ala Thr Glu Ser Asp Val Ile Ile Ala Asn Arg Val
                355                 360                 365
Pro Val Glu His Arg Ile Leu Phe Gly Lys Lys Leu Ile Thr Arg Asp
            370                 375                 380
Val Tyr Gly Asp Asn
385

<210> SEQ ID NO 13
<211> LENGTH: 1170
<212> TYPE: DNA
<213> ORGANISM: Chlorella virus

<400> SEQUENCE: 13
atgtcacgaa tcgcagtcgt tggttgtggt tacgtcggaa ccgcttgtgc agtacttctt      60
gctcaaaaaa acgaagtcac cgtgcttgat attagtgaag accgtgttca gctaatcaag     120
aacaagaaga gtccaatcga ggacaaggaa atcgaagagt ttctcgaaac gaaagacctg     180
aacctgaccg cgacgactga caaggttctt gcatacgaaa acgccgaatt tgtcatcatc     240
gcaaccccga ctgactatga cgtggttact aggtatttta acacgaaatc tgtggaaagc     300
gttatcgggg atgtgatcga aaatacacgg acccagccaa ctattgtgat aaatctacc      360 atccccattg gatttgttga taaggttcgt gagcaattca actacagcaa cattatattc     420
tctccggagt ttctgcgcga aggtagggca ttgtatgata atctctatcc atcgcgtatt     480
atcgtaggag atgattcccc cattgcgctt aagttcgcaa accttctcgt tgaaggttct     540
aaaactccgc ttgcccctgt cctgacgatg ggaactcgcg aagccgaggc cgtcaaacta     600
ttctctaaca cgtatcttgc aatgcgagtt gcatacttca acgaactaga tacattcgca     660
atgtctcatg gtatgaatgc gaaagaaatc attgacggtg tgactttgga gcctcgcatt     720
ggtcaggggt actcaaaccc ttcgttcggt tatggagctt attgctttcc gaaggatacg     780
aagcaactgc tggctaattt cgaggggtg cctcaagata taatcggggc aattgtagaa     840
tcaaatgaaa ctcgcaagga agcgattgta agtgaagtag aaaatcgttt tcccacgact     900
gttggtgtgt ataagctcgc tgctaaagcg ggttctgata attttagaag ttctgcaatt     960
gtagacataa tggagcgact tgcaaacagg ggttatcaca ttaagatttt cgaaccaact    1020
gtggaacaat tcgaaaactt tgaagttgat aacaacctga acatttgc gactgatagc     1080 gatgtaatta tcgcaaacag agttcccgtt gaacatcgca ttctctttgg taaaaaattg    1140
atcacacgtg atgtatatgg cgataactaa                                     1170

<210> SEQ ID NO 14
<211> LENGTH: 389
<212> TYPE: PRT
<213> ORGANISM: Chlorella virus

<400> SEQUENCE: 14

Met Ser Arg Ile Ala Val Val Gly Cys Gly Tyr Val Gly Thr Ala Cys
```

```
              1               5                  10                 15
            Ala Val Leu Leu Ala Gln Lys Asn Glu Val Thr Val Leu Asp Ile Ser
                            20                 25                 30

Glu Asp Arg Val Gln Leu Ile Lys Asn Lys Lys Ser Pro Ile Glu Asp
                            35                 40                 45

Lys Glu Ile Glu Glu Phe Leu Glu Thr Lys Asp Leu Asn Leu Thr Ala
             50                 55                 60

Thr Thr Asp Lys Val Leu Ala Tyr Glu Asn Ala Glu Phe Val Ile Ile
             65                 70                 75                 80

Ala Thr Pro Thr Asp Tyr Asp Val Val Thr Arg Tyr Phe Asn Thr Lys
                            85                 90                 95

Ser Val Glu Ser Val Ile Gly Asp Val Ile Glu Asn Thr Arg Thr Gln
                            100                105                110

Pro Thr Ile Val Ile Lys Ser Thr Ile Pro Ile Gly Phe Val Asp Lys
                            115                120                125

Val Arg Glu Gln Phe Asn Tyr Ser Asn Ile Ile Phe Ser Pro Glu Phe
                            130                135                140

Leu Arg Glu Gly Arg Ala Leu Tyr Asp Asn Leu Tyr Pro Ser Arg Ile
            145                150                155                160

Ile Val Gly Asp Asp Ser Pro Ile Ala Leu Lys Phe Ala Asn Leu Leu
                            165                170                175

Val Glu Gly Ser Lys Thr Pro Leu Ala Pro Val Leu Thr Met Gly Thr
                            180                185                190

Arg Glu Ala Glu Ala Val Lys Leu Phe Ser Asn Thr Tyr Leu Ala Met
                            195                200                205

Arg Val Ala Tyr Phe Asn Glu Leu Asp Thr Phe Ala Met Ser His Gly
                            210                215                220

Met Asn Ala Lys Glu Ile Ile Asp Gly Val Thr Leu Glu Pro Arg Ile
            225                230                235                240

Gly Gln Gly Tyr Ser Asn Pro Ser Phe Gly Tyr Gly Ala Tyr Cys Phe
                            245                250                255

Pro Lys Asp Thr Lys Gln Leu Leu Ala Asn Phe Glu Gly Val Pro Gln
                            260                265                270

Asp Ile Ile Gly Ala Ile Val Glu Ser Asn Glu Thr Arg Lys Glu Ala
                            275                280                285

Ile Val Ser Glu Val Glu Asn Arg Phe Pro Thr Thr Val Gly Val Tyr
                            290                295                300

Lys Leu Ala Ala Lys Ala Gly Ser Asp Asn Phe Arg Ser Ser Ala Ile
            305                310                315                320

Val Asp Ile Met Glu Arg Leu Ala Asn Arg Gly Tyr His Ile Lys Ile
                            325                330                335

Phe Glu Pro Thr Val Glu Gln Phe Glu Asn Phe Glu Val Asp Asn Asn
                            340                345                350

Leu Thr Thr Phe Ala Thr Asp Ser Asp Val Ile Ile Ala Asn Arg Val
                            355                360                365

Pro Val Glu His Arg Ile Leu Phe Gly Lys Lys Leu Ile Thr Arg Asp
                            370                375                380

Val Tyr Gly Asp Asn
            385

<210> SEQ ID NO 15
<211> LENGTH: 1443
<212> TYPE: DNA
<213> ORGANISM: Arabidopsis thaliana
```

```
<400> SEQUENCE: 15
atggtgaaga tctgttgtat tggagctgga tatgtaggag gaccaacaat ggcagtgatt    60
gcattgaaat gtccagatat tgaagtggca gttgttgata tctctgttcc tagaatcaac   120
gcttggaaca gtgatcagct tccgatttac gagccaggtc ttgacgatat cgttaagcaa   180
tgcagaggaa agaatctttt cttcagtact gatgtggaga acatgttag agaagctgat    240
attgtctttg tctctgttaa cacaccgact aaaacgactg gtcttggagc tgggaaagct   300
gctgatctca cttattggga gagtgctgct cgtatgatcg cggatgtatc ggtttctgac   360
aagattgttg ttgagaaatc gactgttccg gtgaagacag ctgaagctat tgagaagatt   420
ttgatgcata acagtaaagg aatcaagttt cagattcttt cgaatccgga gtttcttgct   480
gaaggaactg ctatcgctga tcttttttaac cctgaccgtg ttttgatcgg agggcgagaa  540
acacctgaag gattcaaagc tgttcagaca cttaaagagg tttatgctaa ttgggttcct   600
gaaggtcaga tcatcacaac taatctctgg tctgctgagc tttctaagtt agctgcaaat   660
gctttcttgg ctcagaggat ttcatcagtc aatgccatgt ctgcactttg tgaatccact   720
ggtgctgatg ttactcaagt gtcttacgct gttggtactg attcaagaat cggttccaaa   780
ttcttgaacg ctagtgttgg attcggaggt tcttgtttcc agaaggacat tctgaatctc   840
gtctacatct gtcaatgcaa cggacttcca gaagtggcgg aatactggaa acaagtgatc   900
aagatcaacg attaccaaaa gaaccggttc gtgaacagaa tcgtgtcctc tatgttcaac   960
actgtctcca acaagaaggt tgcgattctt ggattcgcat tcaagaagga cactggtgac  1020
acaagggaaa cacctgccat tgatgtgtgt aaaggtctat taggagacaa agcacagatc  1080
agtatctatg atcctcaagt cacagaggaa cagattcaga gagatctctc gatgaaaaag  1140
ttcgactggg accatcctct tcacttgcag ccaatgagtc caaccacagt gaaacaagtg  1200
agtgtgactt gggacgcata tgaagctaca aagacgcac acgcggtttg cgttttgact   1260
gagtgggacg agtttaagtc gttagattac cagaagatct tcgacaacat gcagaaaccg  1320
gcttttatct tcgacggaag aaacattatg aatgttaaca gttaagaga gattggtttc   1380
attgtttact ccattggtaa gccacttgac ccatggctca aggacatgcc tgcctttgtc  1440
taa                                                                1443

<210> SEQ ID NO 16
<211> LENGTH: 480
<212> TYPE: PRT
<213> ORGANISM: Arabidopsis thaliana

<400> SEQUENCE: 16

Met Val Lys Ile Cys Cys Ile Gly Ala Gly Tyr Val Gly Gly Pro Thr
1               5                   10                  15

Met Ala Val Ile Ala Leu Lys Cys Pro Asp Ile Glu Val Ala Val Val
                20                  25                  30

Asp Ile Ser Val Pro Arg Ile Asn Ala Trp Asn Ser Asp Gln Leu Pro
            35                  40                  45

Ile Tyr Glu Pro Gly Leu Asp Asp Ile Val Lys Gln Cys Arg Gly Lys
        50                  55                  60

Asn Leu Phe Phe Ser Thr Asp Val Glu Lys His Val Arg Glu Ala Asp
65                  70                  75                  80

Ile Val Phe Val Ser Val Asn Thr Pro Thr Lys Thr Gly Leu Gly
                85                  90                  95

Ala Gly Lys Ala Ala Asp Leu Thr Tyr Trp Glu Ser Ala Ala Arg Met
            100                 105                 110
```

```
Ile Ala Asp Val Ser Val Ser Asp Lys Ile Val Glu Lys Ser Thr
        115                 120                 125
Val Pro Val Lys Thr Ala Glu Ala Ile Glu Lys Ile Leu Met His Asn
130                 135                 140
Ser Lys Gly Ile Lys Phe Gln Ile Leu Ser Asn Pro Glu Phe Leu Ala
145                 150                 155                 160
Glu Gly Thr Ala Ile Ala Asp Leu Phe Asn Pro Asp Arg Val Leu Ile
                165                 170                 175
Gly Gly Arg Glu Thr Pro Glu Gly Phe Lys Ala Val Gln Thr Leu Lys
                180                 185                 190
Glu Val Tyr Ala Asn Trp Val Pro Glu Gly Gln Ile Thr Thr Asn
            195                 200                 205
Leu Trp Ser Ala Glu Leu Ser Lys Leu Ala Ala Asn Ala Phe Leu Ala
        210                 215                 220
Gln Arg Ile Ser Ser Val Asn Ala Met Ser Ala Leu Cys Glu Ser Thr
225                 230                 235                 240
Gly Ala Asp Val Thr Gln Val Ser Tyr Ala Val Gly Thr Asp Ser Arg
                245                 250                 255
Ile Gly Ser Lys Phe Leu Asn Ala Ser Val Gly Phe Gly Gly Ser Cys
                260                 265                 270
Phe Gln Lys Asp Ile Leu Asn Leu Val Tyr Ile Cys Gln Cys Asn Gly
            275                 280                 285
Leu Pro Glu Val Ala Glu Tyr Trp Lys Gln Val Ile Lys Ile Asn Asp
        290                 295                 300
Tyr Gln Lys Asn Arg Phe Val Asn Arg Ile Val Ser Ser Met Phe Asn
305                 310                 315                 320
Thr Val Ser Asn Lys Lys Val Ala Ile Leu Gly Phe Ala Phe Lys Lys
                325                 330                 335
Asp Thr Gly Asp Thr Arg Glu Thr Pro Ala Ile Asp Val Cys Lys Gly
                340                 345                 350
Leu Leu Gly Asp Lys Ala Gln Ile Ser Ile Tyr Asp Pro Gln Val Thr
            355                 360                 365
Glu Glu Gln Ile Gln Arg Asp Leu Ser Met Lys Lys Phe Asp Trp Asp
        370                 375                 380
His Pro Leu His Leu Gln Pro Met Ser Pro Thr Thr Val Lys Gln Val
385                 390                 395                 400
Ser Val Thr Trp Asp Ala Tyr Glu Ala Thr Lys Asp Ala His Ala Val
                405                 410                 415
Cys Val Leu Thr Glu Trp Asp Glu Phe Lys Ser Leu Asp Tyr Gln Lys
                420                 425                 430
Ile Phe Asp Asn Met Gln Lys Pro Ala Phe Ile Phe Asp Gly Arg Asn
            435                 440                 445
Ile Met Asn Val Asn Lys Leu Arg Glu Ile Gly Phe Ile Val Tyr Ser
        450                 455                 460
Ile Gly Lys Pro Leu Asp Pro Trp Leu Lys Asp Met Pro Ala Phe Val
465                 470                 475                 480

<210> SEQ ID NO 17
<211> LENGTH: 1443
<212> TYPE: DNA
<213> ORGANISM: Arabidopsis thaliana

<400> SEQUENCE: 17
atggtgaaga tatgttgtat tggagctggg tatgttggtg gaccaacaat ggcagtgatt     60
```

```
gcattgaaat gtccagacgt tgaagtagcg gttgttgata tctctgtacc acgtatcaac      120
gcttggaaca gtgacacgct tccgatttac gagcctggtc ttgatgatgt tgtgaagcaa      180
tgccgtggca agaaccttt  ctttagtact gatgttgaga acatgttag  ggaagctgat      240
attgtgtttg tttctgtcaa cacaccgact aagactagag tcttggtgc  tggtaaagct      300
gcggatctta cgtactggga gagcgctgcg cgtatgatcg ctgatgtttc ggtatcggat      360
aagattgtcg ttgagaaatc gactgttccg gttaaaacag ctgaagctat tgagaagatt      420
ttgacacata acagtaaagg gattaagttt cagattcttt cgaatcccga gttttggcg      480
gaaggaaccg cgattaagga cctatttaat ccggaccgtg ttcttatcgg agggcgggaa      540
accccagaag ggtttaaagc ggtgcagact ctcaagaatg tgtatgcaca ctgggttcct      600
gaaggccaaa tcataacaac caatctctgg tctgctgagc tgtccaagct tgcggcaaac      660
gctttcttgg ctcaaaggat ttcatcagtg aatgctatgt cggctctgtg tgaagccaca      720
ggcgcagatg tcacgcaagt gtcttacgcg gttggtacag actcaaggat tggtcccaag      780
ttcttgaact cgagtgttgg attcggtggt tcgtgtttcc agaaggacat tctgaatctt      840
gtctacatct gtgagtgcaa cggactcccg gaagtggcag agtactggaa gcaagtcatc      900
aagatcaatg actaccagaa gagccggttc gtgaaccgtg ttgtttcctc catgttcaac      960
tctgtatcaa acaagaagat tgcggttctc ggtttcgcat tcaagaaaga caccggtgac    1020
acaagggaga ctccagccat cgatgtgtgc aagggtcttt tagaagacaa agcaaggcta    1080
agcatttacg acccacaagt gactgaggat cagatccaga gggatttatc catgaacaag    1140
ttcgactggg accatcctct acatttgcag ccaatgagcc aacaacagt  gaaacaagtg    1200
accgttactt gggacgcata cgaagcaact aaggacgctc acggtatctg catcatgacc    1260
gagtgggatg agttcaagaa ccttgatttc agaagatct  ttgacaacat gcagaaacca    1320
gctttcgtgt tcgatggaag aaacattatg aatctgcaaa agctaaggga gattggtttc    1380
attgtttact ccattggtaa gcctctcgac gactggctca aggacatgcc tgccgttgcc    1440
taa                                                                  1443
```

<210> SEQ ID NO 18
<211> LENGTH: 480
<212> TYPE: PRT
<213> ORGANISM: Arabidopsis thaliana

<400> SEQUENCE: 18

```
Met Val Lys Ile Cys Cys Ile Gly Ala Gly Tyr Val Gly Gly Pro Thr
1               5                   10                  15

Met Ala Val Ile Ala Leu Lys Cys Pro Asp Val Glu Val Ala Val Val
            20                  25                  30

Asp Ile Ser Val Pro Arg Ile Asn Ala Trp Asn Ser Asp Thr Leu Pro
        35                  40                  45

Ile Tyr Glu Pro Gly Leu Asp Asp Val Val Lys Gln Cys Arg Gly Lys
    50                  55                  60

Asn Leu Phe Phe Ser Thr Asp Val Glu Lys His Val Arg Glu Ala Asp
65                  70                  75                  80

Ile Val Phe Val Ser Val Asn Thr Pro Thr Lys Thr Arg Gly Leu Gly
                85                  90                  95

Ala Gly Lys Ala Ala Asp Leu Thr Tyr Trp Glu Ser Ala Ala Arg Met
            100                 105                 110

Ile Ala Asp Val Ser Val Ser Asp Lys Ile Val Val Glu Lys Ser Thr
        115                 120                 125
```

Val Pro Val Lys Thr Ala Glu Ala Ile Glu Lys Ile Leu Thr His Asn
130                 135                 140

Ser Lys Gly Ile Lys Phe Gln Ile Leu Ser Asn Pro Glu Phe Leu Ala
145                 150                 155                 160

Glu Gly Thr Ala Ile Lys Asp Leu Phe Asn Pro Asp Arg Val Leu Ile
            165                 170                 175

Gly Gly Arg Glu Thr Pro Glu Gly Phe Lys Ala Val Gln Thr Leu Lys
            180                 185                 190

Asn Val Tyr Ala His Trp Val Pro Glu Gly Gln Ile Ile Thr Thr Asn
        195                 200                 205

Leu Trp Ser Ala Glu Leu Ser Lys Leu Ala Ala Asn Ala Phe Leu Ala
210                 215                 220

Gln Arg Ile Ser Ser Val Asn Ala Met Ser Ala Leu Cys Glu Ala Thr
225                 230                 235                 240

Gly Ala Asp Val Thr Gln Val Ser Tyr Ala Val Gly Thr Asp Ser Arg
            245                 250                 255

Ile Gly Pro Lys Phe Leu Asn Ser Ser Val Gly Phe Gly Gly Ser Cys
            260                 265                 270

Phe Gln Lys Asp Ile Leu Asn Leu Val Tyr Ile Cys Glu Cys Asn Gly
        275                 280                 285

Leu Pro Glu Val Ala Glu Tyr Trp Lys Gln Val Ile Lys Ile Asn Asp
290                 295                 300

Tyr Gln Lys Ser Arg Phe Val Asn Arg Val Val Ser Ser Met Phe Asn
305                 310                 315                 320

Ser Val Ser Asn Lys Lys Ile Ala Val Leu Gly Phe Ala Phe Lys Lys
            325                 330                 335

Asp Thr Gly Asp Thr Arg Glu Thr Pro Ala Ile Asp Val Cys Lys Gly
            340                 345                 350

Leu Leu Glu Asp Lys Ala Arg Leu Ser Ile Tyr Asp Pro Gln Val Thr
        355                 360                 365

Glu Asp Gln Ile Gln Arg Asp Leu Ser Met Asn Lys Phe Asp Trp Asp
370                 375                 380

His Pro Leu His Leu Gln Pro Met Ser Pro Thr Thr Lys Gln Val
385                 390                 395                 400

Thr Val Thr Trp Asp Ala Tyr Glu Ala Thr Lys Asp Ala His Gly Ile
            405                 410                 415

Cys Ile Met Thr Glu Trp Asp Glu Phe Lys Asn Leu Asp Phe Gln Lys
            420                 425                 430

Ile Phe Asp Asn Met Gln Lys Pro Ala Phe Val Phe Asp Gly Arg Asn
        435                 440                 445

Ile Met Asn Leu Gln Lys Leu Arg Glu Ile Gly Phe Ile Val Tyr Ser
450                 455                 460

Ile Gly Lys Pro Leu Asp Asp Trp Leu Lys Asp Met Pro Ala Val Ala
465                 470                 475                 480

<210> SEQ ID NO 19
<211> LENGTH: 1443
<212> TYPE: DNA
<213> ORGANISM: Arabidopsis thaliana

<400> SEQUENCE: 19
atggtgaaga tttgctgcat tggagctgga tatgttggtg gtccaaccat ggctgtcatt    60
gctctaaagt gtccatctgt tgaagtagct gttgttgata tctctgtgcc aaggatcaat   120
gcctggaaca gtgatcagtt accgatctat gagcctggtc ttgatgatgt cgttaagcag   180

```
tgccgtggaa agaatctctt cttcagcacc gatgttgaga acatgtgag agaggctgac    240 attgttttg tgtctgtcaa cacccctact aagacccgtg gtcttggagc tggcaaagct    300
gcggatttga cttactggga gagcgctgct cgtatgattg ccgatgtttc ggtttccgac    360
aagattgttg ttgagaaatc aactgttcct gtcaaaaccg cagaggcaat tgagaagatt    420
cttacacaca acagcaaagg aatcaaattc agattctgt caaaccctga gttccttgct    480
gaaggaaccg ctattgaaga cctttcatg cctgaccgtg tcctcatcgg tggtcgtgaa    540
acaactgaag ctttgcagc cgtcaaagcc ttgaaagaca tttatgccca atgggtccct    600
gaagagagaa tcctcaccac caatctatgg tctgccgagc tttccaagct gcagctaat    660 gccttcctag cccagagaat ctcatcagtc aatgcaatgt ccgctctctg tgaggcaact    720
ggcgccaatg tctcagaggt ctcttatgct gtgggcaaag actctcgtat tggtcccaag    780
ttcttgaact ctagtgttgg gttcggagga tcttgtttcc agaaagatat tctcaactta    840
gtctacatct gcgaatgcaa cggcttaccc gaagttgctg agtactgaa acaagtcatc    900 aagatcaacg actaccagaa accctgatt gttaaccgca ttgtctcttc aatgttaac    960 acagtctcca caaaaagat tgcggttctc ggcttcgctt tcaagaaaga cactggagac   1020
actagagaga ctccagccat tgatgtctgc aaaggtctgt taggtgacaa ggctcgtctc   1080
agcatctacg acccacaagt cactgaagag cagatccaaa gagacttaac catgaacaaa   1140
ttcgactggg accaccccact tcatctccag cccatgagcc ccaccactgt gaagcaagtc   1200
tcagtcgctt gggacgcata cactgcaacc aaagacgccc acggtatctg catttaacc   1260 gagtgggacg agttcaagaa acttgatttc cagcggatct ttgagaatat gcagaaaccg   1320
gcttttgttt ttgacggtag aaacgtggtc gacgctgata aactcaggga gattgggttt   1380
attgtttact ccattggtaa gccattggac cagtggctca aggacatgcc tgctcttgcc   1440
taa                                                                 1443
```

<210> SEQ ID NO 20
<211> LENGTH: 480
<212> TYPE: PRT
<213> ORGANISM: Arabidopsis thaliana

<400> SEQUENCE: 20

Met Val Lys Ile Cys Cys Ile Gly Ala Gly Tyr Val Gly Gly Pro Thr
1               5                   10                  15

Met Ala Val Ile Ala Leu Lys Cys Pro Ser Val Glu Val Ala Val Val
                20                  25                  30

Asp Ile Ser Val Pro Arg Ile Asn Ala Trp Asn Ser Asp Gln Leu Pro
        35                  40                  45

Ile Tyr Glu Pro Gly Leu Asp Asp Val Val Lys Gln Cys Arg Gly Lys
    50                  55                  60

Asn Leu Phe Phe Ser Thr Asp Val Glu Lys His Val Arg Glu Ala Asp
65                  70                  75                  80

Ile Val Phe Val Ser Val Asn Thr Pro Thr Lys Thr Arg Gly Leu Gly
                85                  90                  95

Ala Gly Lys Ala Ala Asp Leu Thr Tyr Trp Glu Ser Ala Ala Arg Met
                100                 105                 110

Ile Ala Asp Val Ser Val Ser Asp Lys Ile Val Glu Lys Ser Thr
            115                 120                 125

Val Pro Val Lys Thr Ala Glu Ala Ile Glu Lys Ile Leu Thr His Asn
    130                 135                 140

Ser Lys Gly Ile Lys Phe Gln Ile Leu Ser Asn Pro Glu Phe Leu Ala

```
                145                 150                 155                 160
Glu Gly Thr Ala Ile Glu Asp Leu Phe Met Pro Asp Arg Val Leu Ile
            165                 170                 175
Gly Gly Arg Glu Thr Thr Glu Gly Phe Ala Ala Val Lys Ala Leu Lys
            180                 185                 190
Asp Ile Tyr Ala Gln Trp Val Pro Glu Glu Arg Ile Leu Thr Thr Asn
            195                 200                 205
Leu Trp Ser Ala Glu Leu Ser Lys Leu Ala Ala Asn Ala Phe Leu Ala
            210                 215                 220
Gln Arg Ile Ser Ser Val Asn Ala Met Ser Ala Leu Cys Glu Ala Thr
225                 230                 235                 240
Gly Ala Asn Val Ser Glu Val Ser Tyr Ala Val Gly Lys Asp Ser Arg
            245                 250                 255
Ile Gly Pro Lys Phe Leu Asn Ser Ser Val Gly Phe Gly Gly Ser Cys
            260                 265                 270
Phe Gln Lys Asp Ile Leu Asn Leu Val Tyr Ile Cys Glu Cys Asn Gly
            275                 280                 285
Leu Pro Glu Val Ala Glu Tyr Trp Lys Gln Val Ile Lys Ile Asn Asp
            290                 295                 300
Tyr Gln Lys Thr Arg Phe Val Asn Arg Ile Val Ser Ser Met Phe Asn
305                 310                 315                 320
Thr Val Ser Asn Lys Lys Ile Ala Val Leu Gly Phe Ala Phe Lys Lys
            325                 330                 335
Asp Thr Gly Asp Thr Arg Glu Thr Pro Ala Ile Asp Val Cys Lys Gly
            340                 345                 350
Leu Leu Gly Asp Lys Ala Arg Leu Ser Ile Tyr Asp Pro Gln Val Thr
            355                 360                 365
Glu Glu Gln Ile Gln Arg Asp Leu Thr Met Asn Lys Phe Asp Trp Asp
            370                 375                 380
His Pro Leu His Leu Gln Pro Met Ser Pro Thr Thr Val Lys Gln Val
385                 390                 395                 400
Ser Val Ala Trp Asp Ala Tyr Thr Ala Thr Lys Asp Ala His Gly Ile
            405                 410                 415
Cys Ile Leu Thr Glu Trp Asp Glu Phe Lys Lys Leu Asp Phe Gln Arg
            420                 425                 430
Ile Phe Glu Asn Met Gln Lys Pro Ala Phe Val Phe Asp Gly Arg Asn
            435                 440                 445
Val Val Asp Ala Asp Lys Leu Arg Glu Ile Gly Phe Ile Val Tyr Ser
            450                 455                 460
Ile Gly Lys Pro Leu Asp Gln Trp Leu Lys Asp Met Pro Ala Leu Ala
465                 470                 475                 480

<210> SEQ ID NO 21
<211> LENGTH: 1446
<212> TYPE: DNA
<213> ORGANISM: Arabidopsis thaliana

<400> SEQUENCE: 21
atggtgaaga tatgctgcat aggagctggt tatgtgggtg gtccaaccat ggcggtgatg      60
gctcttaagt gtcctgagat tgaagtagtc gttgtggata tctctgaacc aaggatcaat     120
gcttggaaca gtgataggct tcctatttac gagccgggat tggaagatgt ggtgaaacaa     180
tgcagaggga aaaacctctt ctttagcaca gacgtggaga acatgtgtat tgagagtgat     240
attgtatttg tctcagttaa cactccaacc aaaacacaag gtcttggtgc tggcaaagct     300
```

```
gctgatctta cttactggga gagtgctgct cggatgatcg ctgatgtctc caaatctagc    360
aaaatcgttg ttgagaaatc cacggttcct gtgaggacag cagaggctat tgaaaagata    420
ctgacacata acagcaaagg catagagttt cagattctct ctaaccctga atttcttgct    480
gagggtactg caattaagga tctttataac ccagaccgtg tgttgattgg tggtagggat    540
actgcagcag ggcaaaaggc tattaaagct ttaagagatg tttatgctca ttgggttcca    600
gtggaacaaa tcatttgcac gaacctgtgg tccgctgagc tctctaagct tgcagcaaat    660
gcattcttag ctcagaggat atcatctgtc aatgccatgt cagctctatg tgaggcaact    720
ggcgctgatg ttacacaagt tgcgcatgcc gtgggtacag atactagaat tggtccaaag    780
ttcttgaatg ctagtgttgg ttttggtgga tcatgtttcc aaaaggacat cctaaatctt    840
atctatattt gtgaatgcaa cggcttgccc gaagcagcta attactggaa acaagtcgta    900
aaggtgaacg actatcagaa aatacggttt gcaaaccggg ttgtttcttc aatgtttaac    960
acagtctcgg gcaagaaaat cgcgatcctc ggttttgcct tcaagaagga cacaggtgac   1020
acgagagaga ctccagcgat tgatgtttgt aacagattag ttgcagacaa ggccaagctg   1080
agcatatacg acccacaagt tcttgaagaa cagatcagaa gagatctttc catggctagg   1140
tttgactggg accaccctgt tcctcttcag cagattaaag ctgaaggtat ctcagagcaa   1200
gtgaatgtcg tctcagatgc ttacgaggca actaaagatg cgcacggcct atgtgtctta   1260
accgaatggg atgagtttaa atccttggac ttcaagaaaa tctttgacaa tatgcagaaa   1320
ccagcttttg tgttcgatgg taggaatgtt gttgatgcag tgaagctgcg tgagatcggt   1380
ttcatcgtct actccattgg taaaccgctt gattcatggc tcaaggatat gcctgctgtg   1440
gcatga                                                              1446
```

<210> SEQ ID NO 22
<211> LENGTH: 481
<212> TYPE: PRT
<213> ORGANISM: Arabidopsis thaliana

<400> SEQUENCE: 22

```
Met Val Lys Ile Cys Cys Ile Gly Ala Gly Tyr Val Gly Gly Pro Thr
1               5                   10                  15

Met Ala Val Met Ala Leu Lys Cys Pro Glu Ile Glu Val Val Val Val
                20                  25                  30

Asp Ile Ser Glu Pro Arg Ile Asn Ala Trp Asn Ser Asp Arg Leu Pro
            35                  40                  45

Ile Tyr Glu Pro Gly Leu Glu Asp Val Val Lys Gln Cys Arg Gly Lys
        50                  55                  60

Asn Leu Phe Phe Ser Thr Asp Val Glu Lys His Val Phe Glu Ser Asp
65                  70                  75                  80

Ile Val Phe Val Ser Val Asn Thr Pro Thr Lys Thr Gln Gly Leu Gly
                85                  90                  95

Ala Gly Lys Ala Ala Asp Leu Thr Tyr Trp Glu Ser Ala Ala Arg Met
                100                 105                 110

Ile Ala Asp Val Ser Lys Ser Ser Lys Ile Val Val Glu Lys Ser Thr
            115                 120                 125

Val Pro Val Arg Thr Ala Glu Ala Ile Glu Lys Ile Leu Thr His Asn
        130                 135                 140

Ser Lys Gly Ile Glu Phe Gln Ile Leu Ser Asn Pro Glu Phe Leu Ala
145                 150                 155                 160

Glu Gly Thr Ala Ile Lys Asp Leu Tyr Asn Pro Asp Arg Val Leu Ile
                165                 170                 175
```

Gly Gly Arg Asp Thr Ala Ala Gly Gln Lys Ala Ile Lys Ala Leu Arg
            180                 185                 190

Asp Val Tyr Ala His Trp Val Pro Val Glu Gln Ile Ile Cys Thr Asn
        195                 200                 205

Leu Trp Ser Ala Glu Leu Ser Lys Leu Ala Ala Asn Ala Phe Leu Ala
    210                 215                 220

Gln Arg Ile Ser Ser Val Asn Ala Met Ser Ala Leu Cys Glu Ala Thr
225                 230                 235                 240

Gly Ala Asp Val Thr Gln Val Ala His Ala Val Gly Thr Asp Thr Arg
                245                 250                 255

Ile Gly Pro Lys Phe Leu Asn Ala Ser Val Gly Phe Gly Gly Ser Cys
            260                 265                 270

Phe Gln Lys Asp Ile Leu Asn Leu Ile Tyr Ile Cys Glu Cys Asn Gly
        275                 280                 285

Leu Pro Glu Ala Ala Asn Tyr Trp Lys Gln Val Val Lys Val Asn Asp
    290                 295                 300

Tyr Gln Lys Ile Arg Phe Ala Asn Arg Val Val Ser Ser Met Phe Asn
305                 310                 315                 320

Thr Val Ser Gly Lys Lys Ile Ala Ile Leu Gly Phe Ala Phe Lys Lys
                325                 330                 335

Asp Thr Gly Asp Thr Arg Glu Thr Pro Ala Ile Asp Val Cys Asn Arg
            340                 345                 350

Leu Val Ala Asp Lys Ala Lys Leu Ser Ile Tyr Asp Pro Gln Val Leu
        355                 360                 365

Glu Glu Gln Ile Arg Arg Asp Leu Ser Met Ala Arg Phe Asp Trp Asp
    370                 375                 380

His Pro Val Pro Leu Gln Gln Ile Lys Ala Glu Gly Ile Ser Glu Gln
385                 390                 395                 400

Val Asn Val Val Ser Asp Ala Tyr Glu Ala Thr Lys Asp Ala His Gly
                405                 410                 415

Leu Cys Val Leu Thr Glu Trp Asp Glu Phe Lys Ser Leu Asp Phe Lys
            420                 425                 430

Lys Ile Phe Asp Asn Met Gln Lys Pro Ala Phe Val Phe Asp Gly Arg
        435                 440                 445

Asn Val Val Asp Ala Val Lys Leu Arg Glu Ile Gly Phe Ile Val Tyr
    450                 455                 460

Ser Ile Gly Lys Pro Leu Asp Ser Trp Leu Lys Asp Met Pro Ala Val
465                 470                 475                 480

Ala

<210> SEQ ID NO 23
<211> LENGTH: 32
<212> TYPE: DNA
<213> ORGANISM: Artificial Sequence
<220> FEATURE:
<223> OTHER INFORMATION: The sequence of designed polynucleotide
      described in Example 1

<400> SEQUENCE: 23
gggaattcgt gaagatctgt tgtattggag ct                                32

<210> SEQ ID NO 24
<211> LENGTH: 33
<212> TYPE: DNA
<213> ORGANISM: Artificial Sequence
<220> FEATURE:
<223> OTHER INFORMATION: The sequence of designed polynucleotide

```
                             described in Example 1

<400> SEQUENCE: 24
cagaagcttt tagacaaagg caggcatgtc ctt                                    33

<210> SEQ ID NO 25
<211> LENGTH: 30
<212> TYPE: DNA
<213> ORGANISM: Artificial Sequence
<220> FEATURE:
<223> OTHER INFORMATION: The sequence of designed polynucleotide
      described in Example 1

<400> SEQUENCE: 25
ggaattcgtg aagatatgtt gtattggagc                                        30

<210> SEQ ID NO 26
<211> LENGTH: 31
<212> TYPE: DNA
<213> ORGANISM: Artificial Sequence
<220> FEATURE:
<223> OTHER INFORMATION: The sequence of designed polynucleotide
      described in Example 1

<400> SEQUENCE: 26
aactgcagtt aggcaacggc aggcatgtcc t                                      31

<210> SEQ ID NO 27
<211> LENGTH: 30
<212> TYPE: DNA
<213> ORGANISM: Artificial Sequence
<220> FEATURE:
<223> OTHER INFORMATION: The sequence of designed polynucleotide
      described in Example 1

<400> SEQUENCE: 27
ggaattcgtg aagatttgct gcattggagc                                        30

<210> SEQ ID NO 28
<211> LENGTH: 31
<212> TYPE: DNA
<213> ORGANISM: Artificial Sequence
<220> FEATURE:
<223> OTHER INFORMATION: The sequence of designed polynucleotide
      described in Example 1

<400> SEQUENCE: 28
aactgcagtt aggcaagagc aggcatgtcc t                                      31

<210> SEQ ID NO 29
<211> LENGTH: 30
<212> TYPE: DNA
<213> ORGANISM: Artificial Sequence
<220> FEATURE:
<223> OTHER INFORMATION: The sequence of designed polynucleotide
      described in Example 1

<400> SEQUENCE: 29
ggaattcgtg aagatatgct gcataggagc                                        30

<210> SEQ ID NO 30
<211> LENGTH: 31
<212> TYPE: DNA
<213> ORGANISM: Artificial Sequence
<220> FEATURE:
<223> OTHER INFORMATION: The sequence of designed polynucleotide
      described in Example 1
```

-continued

```
<400> SEQUENCE: 30
gatctagatc atgccacagc aggcatatcc t                                31

<210> SEQ ID NO 31
<211> LENGTH: 30
<212> TYPE: DNA
<213> ORGANISM: Artificial Sequence
<220> FEATURE:
<223> OTHER INFORMATION: The sequence of designed polynucleotide
      described in Example 2

<400> SEQUENCE: 31
ggaattctca cgaatcgcag tcgttggttg                                  30

<210> SEQ ID NO 32
<211> LENGTH: 32
<212> TYPE: DNA
<213> ORGANISM: Artificial Sequence
<220> FEATURE:
<223> OTHER INFORMATION: The sequence of designed polynucleotide
      described in Example 2

<400> SEQUENCE: 32
gactgcagtt agttatcgcc atatacatca cg                               32

<210> SEQ ID NO 33
<211> LENGTH: 40
<212> TYPE: DNA
<213> ORGANISM: Artificial Sequence
<220> FEATURE:
<223> OTHER INFORMATION: The sequence of designed polynucleotide
      described in Example 3

<400> SEQUENCE: 33
gagagtcgac ctattgagta gtcacactct ttgccagatt                       40

<210> SEQ ID NO 34
<211> LENGTH: 35
<212> TYPE: DNA
<213> ORGANISM: Artificial Sequence
<220> FEATURE:
<223> OTHER INFORMATION: The sequence of designed polynucleotide
      described in Example 3

<400> SEQUENCE: 34
atgtgtggaa tcttcgcgta tctgaatttt cacgc                            35

<210> SEQ ID NO 35
<211> LENGTH: 29
<212> TYPE: DNA
<213> ORGANISM: Artificial Sequence
<220> FEATURE:
<223> OTHER INFORMATION: The sequence of designed polynucleotide
      described in Example 4

<400> SEQUENCE: 35
tctgtacgat gcaactacca atgctcagt                                   29

<210> SEQ ID NO 36
<211> LENGTH: 30
<212> TYPE: DNA
<213> ORGANISM: Artificial Sequence
<220> FEATURE:
<223> OTHER INFORMATION: The sequence of designed polynucleotide
      described in Example 4

<400> SEQUENCE: 36
```

```
tatcttacct gggtcaaatg acgaacataa                               30
```

<210> SEQ ID NO 37
<211> LENGTH: 33
<212> TYPE: DNA
<213> ORGANISM: Artificial Sequence
<220> FEATURE:
<223> OTHER INFORMATION: The sequence of designed polynucleotide
      described in Example 4

<400> SEQUENCE: 37

```
atgtgtggca tctttggagc actgtcaaac aac                           33
```

<210> SEQ ID NO 38
<211> LENGTH: 39
<212> TYPE: DNA
<213> ORGANISM: Artificial Sequence
<220> FEATURE:
<223> OTHER INFORMATION: The sequence of designed polynucleotide
      described in Example 4

<400> SEQUENCE: 38

```
aactgcagtt aaaaggtggt cacggatttt gcaagattc                     39
```

<210> SEQ ID NO 39
<211> LENGTH: 39
<212> TYPE: DNA
<213> ORGANISM: Artificial Sequence
<220> FEATURE:
<223> OTHER INFORMATION: The sequence of designed polynucleotide
      described in Example 1

<400> SEQUENCE: 39

```
aactgcagtt aaaaggtggt cacagatttc gcaagattc                     39
```

<210> SEQ ID NO 40
<211> LENGTH: 30
<212> TYPE: DNA
<213> ORGANISM: Artificial Sequence
<220> FEATURE:
<223> OTHER INFORMATION: The sequence of designed polynucleotide
      described in Example 5

<400> SEQUENCE: 40

```
ccggatccat gggtaaaaat ataatcataa                               30
```

<210> SEQ ID NO 41
<211> LENGTH: 30
<212> TYPE: DNA
<213> ORGANISM: Artificial Sequence
<220> FEATURE:
<223> OTHER INFORMATION: The sequence of designed polynucleotide
      described in Example 5

<400> SEQUENCE: 41

```
tatatttaaa tcacacagac tgagcattgg                               30
```

<210> SEQ ID NO 42
<211> LENGTH: 30
<212> TYPE: DNA
<213> ORGANISM: Artificial Sequence
<220> FEATURE:
<223> OTHER INFORMATION: The sequence of designed polynucleotide
      described in Example 6

<400> SEQUENCE: 42

```
aaggatccga tgtgtggcat ctttggagca                               30
```

```
<210> SEQ ID NO 43
<211> LENGTH: 33
<212> TYPE: DNA
<213> ORGANISM: Artificial Sequence
<220> FEATURE:
<223> OTHER INFORMATION: The sequence of designed polynucleotide
      described in Example 13

<400> SEQUENCE: 43
aaggatccat gtcacgaatc gcagtcgttg gtt                              33

<210> SEQ ID NO 44
<211> LENGTH: 35
<212> TYPE: DNA
<213> ORGANISM: Artificial Sequence
<220> FEATURE:
<223> OTHER INFORMATION: The sequence of designed polynucleotide
      described in Example 13

<400> SEQUENCE: 44
ccgagctctt agttatcgcc atatacatca cgtgt                            35
```